(12) United States Patent
Rodrigues

(10) Patent No.: US 11,208,408 B2
(45) Date of Patent: Dec. 28, 2021

(54) METHOD OF CONTROLLING SCALE IN AQUEOUS SYSTEMS

(71) Applicant: NOURYON CHEMICALS INTERNATIONAL B.V., Arnhem (NL)

(72) Inventor: Klin Aloysius Rodrigues, Signal Mountain, TN (US)

(73) Assignee: Nouryon Chemicals International B.V., Arnhem (NL)

( * ) Notice: Subject to any disclaimer, the term of this patent is extended or adjusted under 35 U.S.C. 154(b) by 0 days.

(21) Appl. No.: 17/240,076

(22) Filed: Apr. 26, 2021

(65) Prior Publication Data
US 2021/0253461 A1 Aug. 19, 2021

Related U.S. Application Data

(63) Continuation-in-part of application No. 17/258,896, filed as application No. PCT/US2020/034709 on May 27, 2020.
(Continued)

(30) Foreign Application Priority Data

Aug. 30, 2019 (EP) ..................................... 19194577

(51) Int. Cl.
*C07D 471/06* (2006.01)
*C02F 1/56* (2006.01)
(Continued)

(52) U.S. Cl.
CPC .............. *C07D 471/06* (2013.01); *C02F 1/56* (2013.01); *C02F 5/12* (2013.01); *C08F 2/44* (2013.01);
(Continued)

(58) Field of Classification Search
None
See application file for complete search history.

(56) References Cited

U.S. PATENT DOCUMENTS 3,798,224 A 3/1974 Hotta et al.
5,171,450 A 12/1992 Hoots
(Continued)

FOREIGN PATENT DOCUMENTS

CN 1939945 A 4/2007
CN 105924449 A 9/2016
(Continued)

OTHER PUBLICATIONS

Panah et al. (Iranian Polymer Journal, 2010, 19, 491-500). (Year: 2010).*
(Continued)

*Primary Examiner* — Clare M Perrin
(74) *Attorney, Agent, or Firm* — Norris McLaughlin, P.A.

(57) ABSTRACT

A method of inhibiting scale in an industrial water system includes the steps of dosing the industrial water system with a water treatment polymer comprising at least 10 mol % of carboxylic acid monomer and a quaternized naphthalimide fluorescent monomer as disclosed herein, and then monitoring the fluorescence of the water system. The polymers are also useful for flocculation and coagulation in wastewater treatment.

25 Claims, 7 Drawing Sheets

Related U.S. Application Data

(60) Provisional application No. 62/853,624, filed on May 28, 2019.

(51) Int. Cl.
*C02F 5/12* (2006.01)
*C08F 2/44* (2006.01)
*C08K 5/00* (2006.01)
*C09K 11/06* (2006.01)
*G01N 21/64* (2006.01)
*C02F 103/02* (2006.01)
*C08F 2/10* (2006.01)

(52) U.S. Cl.
CPC ............ *C08K 5/0041* (2013.01); *C09K 11/06* (2013.01); *G01N 21/643* (2013.01); *C02F 2103/02* (2013.01); *C02F 2209/003* (2013.01); *C02F 2303/22* (2013.01); *C09K 2211/1029* (2013.01)

(56) References Cited

U.S. PATENT DOCUMENTS

| | | | |
|---|---|---|---|
| 5,635,575 | A | 6/1997 | Kira et al. |
| 5,986,030 | A | 11/1999 | Murray et al. |
| 6,143,766 | A | 11/2000 | Kaltenbronn et al. |
| 6,280,635 | B1 | 8/2001 | Moriarty et al. |
| 6,645,428 | B1 * | 11/2003 | Morris .................... C02F 5/12 252/301.35 |
| 7,875,720 | B2 | 1/2011 | Morris et al. |
| 9,624,423 | B2 | 4/2017 | Wegner et al. |
| 2004/0013524 | A1 | 7/2004 | Morris et al. |
| 2007/0125987 | A1 * | 6/2007 | Hills .................... C11D 3/3784 252/408.1 |
| 2011/0028371 | A1 | 2/2011 | Rodrigues et al. |
| 2013/0281329 | A1 | 10/2013 | De Wolf et al. |
| 2016/0002525 | A1 | 1/2016 | Wagner et al. |

FOREIGN PATENT DOCUMENTS

| | | |
|---|---|---|
| CN | 109 824 593 A | 5/2019 |
| EP | 0 872 497 A2 | 10/1998 |
| EP | 0 872 497 A3 | 10/1998 |
| RU | 2640339 C2 | 12/2017 |
| WO | 2001/081654 A1 | 11/2001 |
| WO | 2007/074461 A1 | 7/2007 |
| WO | 2013/126816 A1 | 8/2013 |

OTHER PUBLICATIONS

Alexander M. Breul et al: "Fluorescent monomers as building blocks for dye labeled polymers: synthesis and application in energy conversion, biolabeling and sensors", Chemical Society Reviews, vol. 42, No. 12, Jan. 1, 2013 (Jan. 1, 2013), p. 5366.

Cazin et al: "Recent Advances in Functional Polymers Containing Coumarin Chromophores", Polymers, vol. 13, No. 1, Dec. 25, 2020 (Dec. 25, 2020), p. 56.

Merbouh N. et al: "Rapid Chemo-Enzymatic Synthesis of Peracetylated GlcNAc[beta]3Gal[beta]-Aglycones", Journal of Carbohydrate Chemistry, vol. 30, No. 4-6, May 1, 2011 (May 1, 2011), pp. 373-390.

McQuade D T et al: "Signal Amplification of a "Turn-On" Sensor: Harvesting the Light Captured By a Conjugated Polymer", Journal of the American Chemical Society, American Chemical Society, vol. 122, Mar. 11, 2000 (Mar. 11, 2000), p. 12389.

Oliveira H.P.M et al: "Synthesis, structure, electronic and vibrational spectra of 9-(Diethylamino)-benzo(a) phenoxazin-7-ium-5-N-methacrylamide", Spectrochimica Acta Part A: Molecular and Biomolecular Spectroscopy, vol. 58, No. 14, Dec. 1, 2002 (Dec. 1, 2002), pp. 3103-3111.

Feng et al.: "Aggregation-induced emission and solid fluorescence of fluorescein derivatives", Chemical Communications, vol. 56, No. 16, Jan. 1, 2020 (Jan. 1, 2020), pp. 2511-2513.

Shixiong et al: "Science in China (Series B)", vol. 41, No. 5, Oct. 1, 1998 (Oct. 1, 1998), pp. 549-555.

Panah et al., "Synthesis and Characterization of New Fluorescent Polymerizable Dyes Based on Naphthalimide"; Iranian Polymer Journal, 19 (7), 2010, pp. 491-500.

* cited by examiner

METHOD OF CONTROLLING SCALE IN AQUEOUS SYSTEMS

PRIORITY CLAIM

This application is a continuation-in-part of U.S. Non-Provisional application Ser. No. 17/258,896, filed Jan. 8, 2021, now pending, which is a 371 of International Patent Application No. PCT/US2020/034709, filed May 27, 2020, which, in turn, claims priority of European Patent Application No. 19194577.3, filed Aug. 30, 2019, and U.S. Provisional Application Ser. No. 62/853,624, filed May 28, 2019, the entire contents of which are hereby incorporated by herein by reference.

FIELD OF THE DISCLOSURE

This application relates to a method of controlling scale in industrial water systems by treatment with a fluorescent water treatment polymer containing a quaternized naphthalimide monomer. More particularly, this application relates to a method of controlling scale in industrial water systems by treatment with a fluorescent water treatment polymer containing a quaternized naphthalimide monomer for use in the treatment of scale, wherein the polymer has a detectable fluorescent signal. In other embodiments, the application relates to the use of the polymers disclosed for flocculation and coagulation in wastewater treatment, and in cleaning applications.

BACKGROUND

There are many industrial water systems, including, but not limited to, cooling water systems and boiler water systems. Such industrial water systems are subject to corrosion and the formation of scale.

Polymers are widely used in the water treatment industry to minimize scale formation. These scales are carbonate, phosphate, sulfate, oxalate, silica and silicates and others. A wide array of water treatment formulations will also contain phosphate to minimize corrosion. Many states now have regulations limiting the amount of phosphates that can be used in water treatment systems or otherwise be potentially released to the environment. Even in states where the use of phosphate is allowed, it is considered desirable to minimize the amount of phosphate released to the environment. Therefore, the use of higher pH water systems that are lower in phosphates to minimize corrosion issues is becoming more common. But such higher pH water systems lead to increased carbonate scaling. Therefore, there is a need for water treatment polymers for use in industrial water systems with better carbonate scale control properties.

It is known that certain types of water-soluble treatment polymers are effective for preventing formation of scale and suppressing the occurrence of corrosion in industrial water systems. These water-soluble treatment polymers are known to persons of ordinary skill in the art of industrial water systems and are widely used in scale inhibition products. Such water-soluble treatment polymers generally exhibit activity against scale when added to water in an amount in the range of from about 1 to about 100 ppm.

The efficacy of water-soluble treatment polymers in inhibiting scale and suppressing corrosion depends in part on the concentration of the water-soluble treatment polymer in the water system. Water-soluble treatment polymers added to an industrial water system can be consumed by many causes, leading to changes in concentration of the water-soluble treatment polymer. Therefore, it is important for the optimum operation of an industrial water system to be able to accurately determine the concentration of water-soluble treatment polymers in the water.

It is known that the concentration of water-soluble treatment polymers used as components of scale and corrosion inhibitors in industrial water systems can be monitored if the polymer is tagged with a fluorescent monomer. The amount of fluorescent monomer incorporated into the water-soluble polymer must be enough so that the fluorescence of the water-soluble polymer can be adequately measured, however, it must not be so much as to adversely impact the performance of the water-soluble polymer as a treatment agent. Because the concentration of the tagged water-soluble treatment polymer can be determined using a fluorimeter, it is also possible to measure consumption of the water-soluble treatment polymer directly. It is important to be able to measure consumption directly because consumption of a water-soluble treatment polymer usually indicates that a non-desired event, such as scaling, is occurring. Thus by being able to measure consumption of the water-soluble treatment polymer, there can be achieved an in-line, real time in situ measurement of scaling activity in the industrial water system. Such in-line, real time measurement systems are disclosed, for example, in U.S. Pat. Nos. 5,171,450 and 6,280,635, which are incorporated herein by reference.

In wastewater treatment, polymers are typically used for flocculation and coagulation. These polymers that typically high molecular weight polymers which are typically produced by polymerizing cationic or nonionic monomers.

Naphthalimide and certain naphthalimide derivatives are known fluorescent compounds that can be converted to polymerizable fluorescent monomers for use in such systems. Naphthalimide has the structural formula:

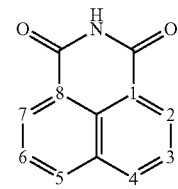

wherein the benzene carbon atoms for purposes of illustrating the present disclosure. The present disclosure uses "ortho" to refer alternatively to the 2- or 7-positions; "meta" to refer alternatively to the 3- or 6-positions; and "para" to refer alternatively to the "4" or "5" positions.

U.S. Pat. No. 6,645,428 discloses fluorescent monomers that can be used to prepare tagged treatment polymers for phosphate scaling. The process disclosed in U.S. Pat. No. 6,645,428 leads to monomers that contain a relatively large fraction of starting non-quaternized amine (see below Structure (III) and Structure (VI)). It has been found that, as a result, polymers made from these monomers contain a considerable amount of the same non-quaternized amine since these moieties do not have a double bond that can be polymerized. The presence of these non-quaternized amine moieties in the polymer will lead to the fluorescent signal becoming unreliable as remainders of these non-quaternized amines also will give a fluorescent signal in unexpectedly the same wavelength region, while they will not have any role in scale prevention and reduction. Chlorine is often use as a biocide in water treatment systems. It is essential to maintain the fluorescent signal in the presence of chlorine.

While not being bound by theory, chlorine negatively impacts the fluorescent signal of the polymers made from monomers of U.S. Pat. No. 6,645,428. This leads to a greater than 10% drop in signal which leads to an inaccurate measurement of the polymer.

U.S. Pat. No. 6,645,428 also describes incorporation of the fluorescent monomers in the tagged treatment polymers to the extent of 37%-99%. The results appear random and the reference does not teach how to optimize the incorporation percentage or even that it should be optimized. It has been found that the presence of unincorporated fluorescent monomer in the treatment polymer is problematic. The presence of significant percentages of unincorporated fluorescent monomer in the treatment polymer renders the fluorescent signal emanating therefrom unreliable.

CN1939945 discloses a process to prepare a fluorescent polymer by reacting 4-methoxy-N-(2-N',N'-dimethylaminoethyl) naphthalimide allyl salt with both maleic anhydride and sodium hypophosphite. This process however suffers from the problem that the reaction towards the polymer has a very poor yield and the product contains a lot of unreacted, maleic acid monomers resulting in a product that has precipitate and cannot be used in practical applications.

CN10648641 discloses an amine group-containing naphthalimide monomer that is polymerized with acrylic acid, itaconic acid, and sodium hypophosphite therewith providing polymers that contain both amine groups and ester groups. Such polymers have as a disadvantage that the amine groups interfere with other chemicals that are often added to water treatment formulations and that ester groups are unstable and may easily be hydrolyzed both during the storage of the water treatment formulations which are typically at high pH and at the temperature and pH conditions as often used during water treatment operations.

CN109824593 discloses water-soluble quaternary ammonium fluorescent monomers, polymers and their use in scale reduction and water-treatment processes. This reference only exemplifies monomers with hydrolysable ester groups.

US 2016/002525 discloses fluorescent monomers containing a 1,8-naphthalimide unit and quaternary-amine vinyl or allyl groups and their incorporation into polymers containing, inter alia, sulfonic acid groups.

Copolymers of acrylic and maleic acids with phosphino groups are conventionally used as carbonate scale control agents in water treatment applications. We have found, however, that even a small amount of quaternized naphthalimide fluorescent monomer included in the polymerization mixture can significantly hinder the polymerization of the maleic acid monomer into the polymer.

It thus would be desirable to provide a method of controlling scale in industrial water systems by treatment with a fluorescent water treatment polymer for use in the treatment of scale and that has a detectable and reliable fluorescent signal under typical industrial water treatment conditions, and that does not have the disadvantages of the prior art. In addition, it is highly desirable to have monomers and polymers made from these monomers that do not have the disadvantages of the prior art.

SUMMARY OF THE DISCLOSURE

To achieve the foregoing objects, a method of controlling scale in industrial water systems comprises the steps of:
(a) dosing the water system with a water treatment polymer composition that is formed from a polymerization mixture comprising:

(i) at least one water-soluble carboxylic acid monomer, or salt or anhydride thereof, present in an amount of 10-99.999 mol % based on 100 mol % of the polymer; and
(ii) at least one quaternized naphthalimide fluorescent monomer comprising either (a) Structure (I) comprising less than 8 mol %, based on 100 mol % of Structure (I), of Structure (III) or (b) Structure (II) comprising less than 8 mol %, based on 100 mol % of Structure (II), of Structure (VI), wherein:

Structure (I) is:

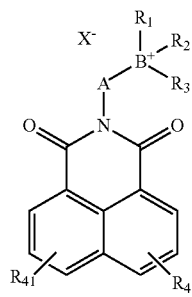

wherein $R_4$ and $R_{41}$ are independently selected from H, hydroxy, alkoxy, aryloxy, arylalkoxy, alkylaryloxy, (meth)allyloxy, vinylbenzyloxy, heteroaryl, —$NO_2$, $C_1$-$C_4$alk-O—$(CHR_5CH_2O—)_n$, —$CO_2H$ or a salt thereof, —$SO_3H$ or a salt thereof, —$PO_3H_2$ or a salt thereof, -alkylene-$CO_2H$ or a salt thereof, -alkylene-$SO_3H$ or a salt thereof, and -alkylene-$PO_3H_2$ or a salt thereof;

n=1-10;

$R_1$ and $R_2$ are independently $C_1$-$C_4$alkyl, preferably $C_1$-$C_2$alkyl, more preferably $C_1$alkyl;

$R_3$ is selected from (meth)allyl, (meth)acryl, 2-hydroxy-3-(meth)allyloxypropyl, 1-hydroxy-3-(meth)allyloxypropyl, vinylbenzyl, 3-(meth)acrylamidopropyl, and 2-(meth)acryloyloxy ethyl, or alkyl;

$R_5$ is selected from H and $C_1$-$C_4$alkyl;

A is selected from the group consisting of alkyl, alkoxyalkyl, alkylamidoalkyl, arylalkyl or nonexistent; with the proviso that when A is nonexistent, B is nitrogen and B is bonded directly to the imide nitrogen;

B is sulfur or nitrogen with the proviso that when B is sulfur only one of $R_1$ or $R_2$ is present; and X is an anionic counter ion preferably selected from chloride, bromide, hydroxide, methosulphate, sulfate, sulfonate, carbon/late, phosphate, and phosphonate;

Structure (II) is:

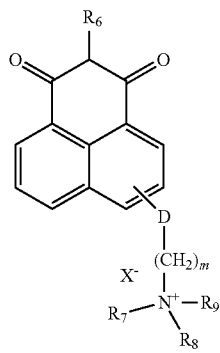

wherein
m=1-10;
$R_7$ and $R_8$ and $R_9$ are each independently an alkyl and may be the same or different;
$R_6$ is selected from the group consisting of vinyl, alkenyl, and (meth)allyl;
D is oxygen or nonexistent, with the proviso that when D is nonexistent, $(CH_2)_m$ is bonded directly to a carbon on the ring; and
X is an anionic counter ion, preferably selected from chloride, bromide, hydroxide, methosulphate, sulfate, sulfonate, carbon/late, phosphate, and phosphonate;
Structure (III) is:

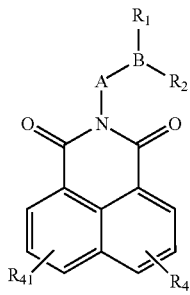

wherein A, B, $R_1$, $R_2$, $R_4$, and $R_{41}$ are as defined above; and
Structure (VI) is:

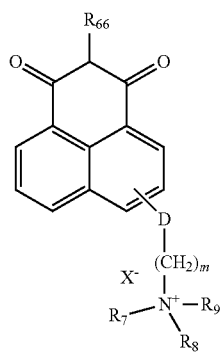

(VI)

wherein D, m, $R_7$-$R_9$, and $X^-$ are as defined above and $R_{66}$ is H or alkyl;
said quaternized naphthalimide fluorescent monomer being present in said water treatment polymer in an amount of 0.001-5 mol % based on 100 mol % of the water treatment polymer; and
said quaternized napthalimide fluorescent monomer being incorporated into said water treatment polymer to an extent equal to or greater than 90%; and
(b) monitoring the fluorescent signal emitted from said industrial water system.

(Unless otherwise indicated, all percentages of a composition, for example, a solid or a solution, are mole percentages based on the total composition.)

The following monomers are new and are claimed per se, i.e., without requiring any particular degree of purity with respect to Structure (III): Monomers of Structure (I):

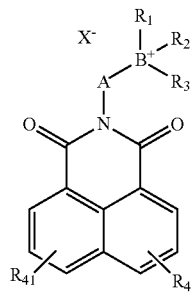

wherein
$R_4$ and $R_{41}$ are independently selected from H, hydroxy, and $C_1$-$C_4$alk-O—$(CHR_5CH_2O)_n$ with the proviso $R_4$ and $R_{41}$ are not both H; or $R_4$ and $R_{41}$ are both alkoxy;
n=1-10;
$R_1$ and $R_2$ are independently $C_1$-$C_4$alkyl, preferably $C_1$-$C_2$alkyl, more preferably $C_1$alkyl;
$R_3$ is selected from (meth)allyl, (meth)acryl, 2-hydroxy-3-(meth)allyloxypropyl, 1-hydroxy-3-(meth)allyloxypropyl, 2-(hydroxy)-3-(ethoxy)-propyl, 3-(allyloxy)-2-(3-(allyloxy)-2-hydroxypropoxy)-propyl, vinylbenzyl, 3-(meth)acrylamidopropyl, and 2-(meth)acryloyloxy ethyl;
$R_5$ is selected from H and $C_1$-$C_4$alkyl;
A is selected from the group consisting of alkyl, alkoxyalkyl, alkylamidoalkyl, arylalkyl or nonexistent; with the proviso that when A is nonexistent, B is nitrogen and B is bonded directly to the imide nitrogen;
B is sulfur or nitrogen with the proviso that when B is sulfur only one of $R_1$ or $R_2$ is present; and
X is an anionic counter ion preferably selected from chloride, bromide, hydroxide, methosulphate, sulfate, sulfonate, carboxylate, phosphate, and phosphonate.

The disclosure relates in another embodiment to a process for preparing the water treatment polymer comprising the following steps:
(a) polymerizing a polymerization mixture comprising:
(i) at least one water-soluble carboxylic acid monomer, or salt or anhydride thereof, present in an amount of 10-99.999 mol % based on 100 mol % of the polymer;
(ii) at least one quaternized naphthalimide fluorescent monomer of either (a) Structure (I) comprising less than 8 mol %, based on 100 mol % of Structure (I), of Structure (III) or (b) Structure (II) comprising less than 8 mol %, based on 100 mol % of Structure (II), of Structure (VI); and (b) ensuring the fluorescent monomer is incorporated into the water treatment polymer to an extent equal to or greater than 90%.

The disclosure relates in yet another embodiment to method of coagulation or flocculation in a water treatment system, the method comprising the steps of:
(a) dosing the water system with the disclosed water treatment polymers; and
(b) monitoring the fluorescent signal emitted from the water treatment system.

BRIEF DESCRIPTION OF THE DRAWINGS

The disclosure will now be described in greater detail with reference to the drawings, wherein.

DETAILED DESCRIPTION

Figure 1:
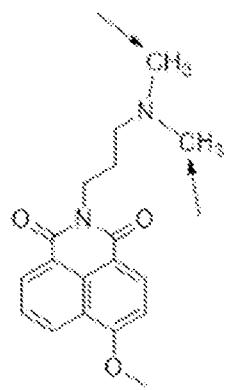
FIG. 1 depicts the chemical structure of N-(3-dimethylaminopropyl)-4-methoxy-1,8-naphthalimide.

Disclosed herein is a method of controlling scale in a water system, the method comprising dosing to the system a fluorescent water treatment polymer made from a polymerization mixture comprising (i) one or more water-soluble carboxylic acid monomers or their salts or anhydrides (ii) one or more quaternized naphthalimide fluorescent monomers as disclosed herein, and optionally further comprising any one or more of (iii) phosphorous-containing moieties selected from the group consisting of phosphino group donating moieties and phosphonate group donating moieties, (iv) sulfonic acid monomers, and (v) nonionic monomers. These scales are carbonate, phosphate, sulfate, oxalate, silica and silicates and others.

As used herein, the term "dosing" of the water system with the water treatment polymer composition means that the water treatment polymer is added over a period of time to the water system, as opposed to a single addition of an entire water treatment polymer composition content to be added. As used herein, the term "dosing" of the water treatment polymer composition into the water system encompasses addition of the water treatment polymer composition to the water system as a continuous stream, addition of the water treatment polymer composition into the water system as several intermittent shots, and combinations thereof.

In one embodiment, for a water system having a Langelier Saturation Index (LSI) of 2, carbonate inhibition of at least 80% is achieved when the water treatment polymer is dosed to a water system at no greater than 100 ppm, more preferably carbonate inhibition of at least 80% is achieved when the water treatment polymer is dosed to a water system at no greater than 50 ppm, and most preferably carbonate inhibition of at least 90% is achieved when the water treatment polymer is dosed to a water system at no greater than 20 ppm. In one embodiment, the polymer gives at least 80% inhibition of carbonate scale at 100, 50, 20, 15 ppm polymer at LSI of 2. The water treatment polymers disclosed herein also will be effective in water treatment systems having LSI values less than or greater than 2.

(i) Carboxylic Acid Monomers

For purposes of this disclosure, water-soluble carboxylic acid monomers include but are not limited to one or more of acrylic acid, methacrylic acid, maleic acid, itaconic acid, citraconic acid, mesaconic acid, glutaconic acid, aconitic acid, ethacrylic acid, alpha-chloro-acrylic acid, alpha-cyano acrylic acid, alpha-chloro-methacrylic acid, alpha-cyano methacrylic acid, beta methyl-acrylic acid (crotonic acid), beta-acryloxy propionic acid, sorbic acid, alpha-chloro sorbic acid, angelic acid, tiglic acid, p-chloro cinnamic acid, and mixtures thereof, and their salts and anhydrides. In one embodiment the carboxylic acid monomers can include mono-alkylesters of dicarboxylic acids including maleic acid and fumaric acid, such as monomethyl maleate and monoethyl maleate. The preferred water-soluble carboxylic acid monomers are acrylic acid, maleic acid, itaconic acid and methacrylic acid with acrylic acid being the most preferred.

The carboxylic acid monomer may be added to the polymerization reaction mixture in the form of the acid, the anhydride, or a salt, as is commonly known in the water treatment polymer arts.

As used herein with respect to water-soluble carboxylic acid monomers, water-soluble means that the monomer has a water solubility as the acid of greater than 6 gram per 100 mls of water at 25° C., preferably greater than 10 grams per 100 mls of water at 25° C., and most preferably greater than 15 grams per 100 mls of water at 25° C.

The carboxylic acid monomers will be present in the polymerization mixture in the range of 10-99.999 mol %. The carboxylic acid monomers can be present as at least 10 mol %, as at least 15 mol %, as at least 20 mol %, as at least 25 mol %, as at least 30 mol %, as at least 35 mol %, as at least 40 mol %, as at least 45 mol %, as at least 50 mol %, as at least 55 mol %, as at least 60 mol %, or at least 65 mol %, or at least 70 mol %, or at least 75 mol %, or at least 80 mol %, or at least 85 mol %, or at least 90 mol % of the polymerization reaction mixture. The carboxylic acid monomers can be present as up to 99.999 mol %, or up to 99 mol %, or up to 98 mol %, or up to 95 mol %, of the polymerization reaction mixture. In each case, the mol % is based on a total of 100 mol % of the polymer.

If, however, the polymer contains a phosphino moiety and at least part of the carboxylic acid monomer is maleic acid or a salt or anhydride thereof, then the maleic acid or salt or anhydride thereof is not greater than 70 mol % of the polymerization reaction mixture.

(ii) Fluorescent Monomers:

The quaternized naphthalimide fluorescent monomers used in the water treatment polymers herein preferably are selected from one or more quaternized naphthalimide monomer derivatives of the illustrated Structure (I) and Structure (II):

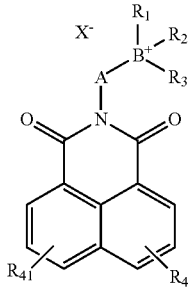

Structure (I)

wherein $R_4$ and $R_{41}$ are independently selected from H, hydroxy, alkoxy, aryloxy, arylalkoxy, alkylaryloxy, (meth)allyloxy, vinylbenzyloxy, heteroaryl, —$NO_2$, $C_1$-$C_4$alk-O—(CHR$_5$CH$_2$O—)$_n$, —$CO_2H$ or a salt thereof, —$SO_3H$ or a salt thereof, —$PO_3H_2$ or a salt thereof, -alkylene-$CO_2H$ or a salt thereof, -alkylene-$SO_3H$ or a salt thereof, and -alkylene-$PO_3H_2$ or a salt thereof;

n=1-10;

$R_1$ and $R_2$ are independently $C_1$-$C_4$alkyl, preferably $C_1$-$C_2$alkyl, more preferably $C_1$alkyl;

$R_3$ is selected from (meth)allyl, (meth)acryl, 2-hydroxy-3-(meth)allyloxypropyl, 1-hydroxy-3-(meth)allyloxypropyl, vinylbenzyl, 3-(meth)acrylamidopropyl, and 2-(meth)acryloyloxy ethyl, or alkyl;

$R_5$ is selected from H and $C_1$-$C_4$alkyl;

A is selected from the group consisting of alkyl, alkoxyalkyl, alkylamidoalkyl, arylalkyl or nonexistent; with the proviso that when A is nonexistent, B is nitrogen and B is bonded directly to the imide nitrogen;

B is sulfur or nitrogen with the proviso that when B is sulfur only one of $R_1$ or $R_2$ is present; and X is an anionic counter ion preferably selected from chloride, bromide, hydroxide, methosulphate, sulfate, sulfonate, carboxylate, phosphate, and phosphonate;

with the proviso that if $R_3$ is (meth)allyl, (meth)acryl, 2-hydroxy-3-(meth)allyloxypropyl, 1-hydroxy-3-(meth)allyloxypropyl, vinylbenzyl, 3-(meth)acrylamidopropyl, 2-(meth) acryloyloxy ethyl, then $R_4$ is not (meth)allyloxy or vinylbenzyloxy; and if $R_4$ is (meth)allyloxy or vinylbenzyloxy then $R_3$ is alkyl; or

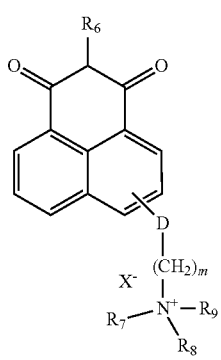

Structure (II)

wherein m=1-10;

$R_7$ and $R_8$ and $R_9$ are each independently an alkyl and may be the same or different;

$R_6$ is selected from the group consisting of vinyl, alkenyl, and (meth)allyl;

D is oxygen or nonexistent, with the proviso that when D is nonexistent, $(CH_2)_m$ is bonded directly to a carbon on the ring; and X is an anionic counter ion, preferably selected from chloride, bromide, hydroxide, methosulphate, sulfate, sulfonate, carboxylate, phosphate, and phosphonate.

It should be noted that in the Structure (I), $R_4$ and $R_{41}$ may have different positions on the aromatic ring, namely para, ortho or meta. In addition, $R_4$ and $R_{41}$ may occupy the same ring. For example, $R_4$ could be at position 4 and $R_{41}$ could be at position 5, i.e., both are para substituents but located on different benzene rings; or $R_4$ could be at position 4 and $R_{41}$ at position 3, i.e., $R_4$ is para substituted and $R_{41}$ is meta substituted but both are located on the same benzene ring.

As used herein, unless otherwise indicated, "alkyl" groups, whether alone or a part of other groups, for example, "alkoxy" or "alkylene," have any suitable carbon atom range, but preferably have 1-10 carbon atoms, most preferably 1-6 carbon atoms, and are optionally substituted by suitable substituents.

As used herein, unless otherwise indicated, "aryl" groups, whether alone or a part of other groups, for example, "aryloxy" or "arylalkoxy," have any suitable carbon atom range, but preferably have 6-14 carbon atoms, most preferably 6 or 10 carbon atoms, i.e., phenyl or naphthyl, and are optionally substituted by suitable substituents.

As used herein, unless otherwise indicated, "heteroaryl" groups, whether alone or a part of other groups, have any suitable combination of heteroatoms and carbon atoms, but preferably have 3-10 ring carbon atoms and 1-3 ring heteroatoms independently selected from the group consisting of N, O, and S atoms, most preferably 3-5 ring carbon atoms and 1-2 ring heteroatoms independently selected from the group consisting of N, O, and S atoms, and are optionally substituted by suitable substituents.

As used herein, unless otherwise indicated, "suitable substituents" include, but are not limited to, halogen, such as F, Cl, Br or I; $NO_2$; CN; haloalkyl, typically $CF_3$; OH; amino; SH; —CHO; —$CO_2H$; oxo (=O); —C(=O)amino; NRC(=O)R; aliphatic, typically alkyl, particularly methyl; heteroaliphatic; —OR, typically methoxy; —SR; —S(=O)R; —$SO_2R$; aryl; or heteroaryl; where each R independently is aliphatic, typically alkyl, aryl, or heteroaliphatic. In certain aspects the optional substituents may themselves be further substituted with one or more unsubstituted substituents selected from the above list. Exemplary optional substituents include, but are not limited to: —OH, oxo (=O), —Cl, —F, Br, $C_{1-4}$alkyl, phenyl, benzyl, —$NH_2$, —NH($C_{1-4}$alkyl), —N($C_{1-4}$alkyl)$_2$, —$NO_2$, —S($C_{1-4}$alkyl), —$SO_2$($C_{1-4}$alkyl), —$CO_2$($C_{1-4}$alkyl), and —O($C_{1-4}$alkyl).

Preferably $R_4$ and $R_{41}$ are independently selected from H, alkoxy, hydroxy, and $C_1$-$C_4$alk-O—(CHR$_5$CH$_2$O—)$_m$. More preferably at least one of $R_1$ and $R_{41}$ are independently alkoxy, which can be selected from methoxy, ethoxy, propyloxy, isopropyloxy, n-butoxy, isobutoxy, and tert-butoxy.

Preferably $R_3$ is selected from 2-hydroxy-3-(meth)allyloxypropyl, 1-hydroxy-3-(meth)allyloxypropyl, and (meth)allyl, with 2-hydroxy-3-(meth)allyloxypropyl being more preferred.

In another preferred embodiment, the fluorescent monomer has the Structure (I)

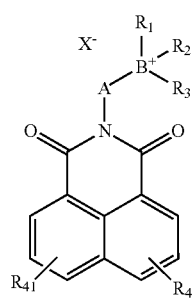

wherein $R_4$ and $R_{41}$ are independently selected from H, hydroxy, alkoxy, and $C_1$-$C_4$alk-O—(CHR$_5$CH$_2$O—)$_n$ with the proviso that $R_4$ and $R_{41}$ are not H;

n=1-10;

$R_1$ and $R_2$ are independently $C_1$-$C_4$alkyl, preferably $C_1$-$C_2$alkyl, more preferably $C_1$alkyl;

$R_3$ is selected from (meth)allyl, (meth)acryl, 2-hydroxy-3-(meth)allyloxypropyl, 1-hydroxy-3-(meth)allyloxypropyl, vinylbenzyl, 3-(meth)acrylamidopropyl, and 2-(meth)acryloyloxy ethyl;

$R_5$ is selected from H and $C_1$-$C_4$alkyl;

A is selected from the group consisting of alkyl, alkoxyalkyl, alkylamidoalkyl, arylalkyl or nonexistent; with the proviso that when A is nonexistent, B is nitrogen and B is bonded directly to the imide nitrogen;

B is sulfur or nitrogen with the proviso that when B is sulfur only one of $R_1$ or $R_2$ is present; and X is an anionic counter ion preferably selected from chloride, bromide, hydroxide, and methosulphate.

In yet another preferred embodiment of the disclosure, in the process a mixture of naphthalimide fluorescent monomers is used in which monomers are present in which both $R_4$ and $R_{41}$ are a substituent other than H, even more preferably such monomers are present in an amount of between 0.1 mole and 50 mol %. In yet another preferred embodiment of the disclosure, in the process a mixture of naphthalimide fluorescent monomers is used in which monomers are present in which both $R_4$ and $R_{41}$ are a substituent other than H, even more preferably such monomers are present in an amount of at least 0.25 mol %, at least 0.5 mol %, at least 0.75 mol %. In yet another preferred embodiment of the disclosure, in the process a mixture of naphthalimide fluorescent monomers is used in which monomers are present in which both $R_4$ and $R_{41}$ are a substituent other than H, even more preferably such monomers are present in an amount of less than 25 mol %, less than 10 mol %, less than 5 mol %. The monomers where $R_4$ and $R_{41}$ are a substituent other than H especially when $R_4$ and $R_{41}$ are both alkoxy have a stronger signal (5-50 times) then when either $R_4$ and $R_{41}$ is H and the other is substituted with an alkoxy group. Therefore, the mixture of monomers where $R_4$ and $R_{41}$ are independently H or a substituent and where $R_4$ and $R_{41}$ are a substituent has a stronger signal then a monomer where $R_4$ and $R_{41}$ are independently H or a substituent especially when the substituent is an alkoxy group.

The quaternized naphthalimide fluorescent monomers of Structures (I) and (II) preferably are substantially free of substituents that are primary, secondary or tertiary amines or esters. This feature has two significant advantages. First, water treatment formulations are typically in the high pH range to solubilize azoles that are used as corrosion inhibitors. Ester substituents present in these high pH formulations can hydrolyze, cleaving the naphthalimide group of the monomer away from the polymer. This free naphthalimide in the water system will emit a fluorescent signal that is not part of the polymer, leading to an inaccurate determination of the amount of polymer in the system. Second, chlorine or hypochlorite is typically used as an oxidizing biocide along with a water treatment polymer in water treatment systems. The primary, secondary or tertiary amines if present would form chloro amines which may change the signal strength or optimum emission wavelength of these fluorescent monomers, further leading to an inaccurate determination of the amount of polymer in the system.

As used herein, the term "substantially free of amine groups" or "substantially free of ester groups" means the non-quaternized fluorescent naphthalimide derivative monomer (or other non-fluorescent monomer) has less than 10 mol %, less than 5 mol %, less than 1 mol % or is free of, respectively, primary, secondary or tertiary amine groups, or ester groups. The mol % is in each case based on 100 mol % of the fluorescent (or non-fluorescent monomer).

The quaternized naphthalimide fluorescent monomers of Structures (I) and (II) are prepared as monomer compositions which are added to a polymerization reaction mixture to make the water treatment polymers, as disclosed in the Examples herein.

When a quaternized naphthalimide fluorescent monomer of Structure (I) is used, preferably the monomer composition is substantially free of non-monomerized naphthalimide compounds of Structure (III):

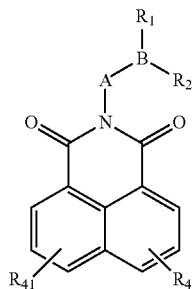

wherein $R_4$ and $R_{41}$ are independently selected from H, hydroxy, alkoxy, aryloxy, arylalkoxy, alkylaryloxy, (meth)allyloxy, vinylbenzyloxy, heteroaryl, —NO$_2$, $C_1$-$C_4$alk-O—(CHR$_5$CH$_2$O—)$_n$, —CO$_2$H or a salt thereof, —SO$_3$H or a salt thereof, —PO$_3$H$_2$ or a salt thereof, -alkylene-CO$_2$H or a salt thereof, -alkylene-SO$_3$H or a salt thereof, and -alkylene-PO$_3$H$_2$ or a salt thereof;

n=1-10;

$R_1$ and $R_2$ are independently $C_1$-$C_4$alkyl, preferably $C_1$-$C_2$alkyl, more preferably $C_1$alkyl;

$R_5$ is selected from H and $C_1$-$C_4$alkyl;

A is selected from the group consisting of alkyl, alkoxyalkyl, alkylamidoalkyl, arylalkyl or nonexistent; with the proviso that when A is nonexistent, B is nitrogen and B is bonded directly to the imide nitrogen; and B is sulfur or nitrogen with the proviso that when B is sulfur only one of $R_1$ or $R_2$ is present.

The monomer of Structure (I) being substantially free of the compound of Structure (III) means that the monomer of Structure (I) has preferably less than 8 mol %, preferably less than 7 mol %, more preferably less than 6 mol %, more preferably less than 5 mol %, more preferably less than 3 mol %, more preferably less than 2 mol %, and most preferably less than 1.5 mol % or is even completely free of the non-monomer compound of Structure (III) relative to the total molar amount of Structure (I), as an impurity when measured by NMR as detailed in Monomer Example 3.

This non-monomer compound of Structure (III) cannot be polymerized but will still emit a fluorescent signal. Surprisingly, the fluorescent signal of the compound of Structure (III) is almost as strong as that of the fluorescent signal from the monomer incorporated into the polymer, as exemplified in Examples 16, 18 and 22. Even more surprising, the excitation and emission wavelengths for the monomer of Structure (I) are almost identical to those of the non-monomer of Structure (III), also as exemplified in Examples 18 and 22. Therefore, the in-line fluorescent measurement would not be able to tell the difference between the monomer of Structure (I) present in the polymer and the non-monomer of Structure (III) present as an impurity in the water treatment polymer solution, resulting in a false signal. Therefore, it is important to minimize or eliminate the impurities of Structure (III). In one embodiment of the disclosure, the polymerizable double bond is introduced to the quaternized naphthalimide precursor by reacting a non-quaternized naphthalimide precursor with a monomer containing the polymerizable double bond. The quantities of impurities of Structure (III) can be eliminated or minimized by using a significant molar excess of the monomer containing the polymerizable double bond in this reaction step. This is illustrated in Step 3 of Monomer Example 3 where the allyl glycidyl ether monomer containing the polymerizable double bond is added in excess. The monomer containing the polymerizable double bond can be added to the monomer synthesis reaction mixture as at least 50% molar excess, or at least 60%, or at least 70%, or at least 80%, or at least 90%, or at least 100% molar excess in the monomer synthesis reaction mixture. However, it is within the scope of the disclosure that other methods can be used to minimize the impurities of Structure (III).

Likewise, when a quaternized naphthalimide fluorescent monomer of Structure (II) is used, preferably the monomer composition is substantially free of the quaternized naphthalimide fluorescent monomer of Structure (VI):

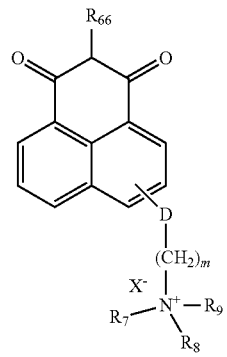

wherein
m=1-10;
$R_7$ and $R_8$ and $R_9$ are each independently an alkyl and may be the same or different;
$R_6$ is selected from the group consisting of vinyl, alkenyl, and (meth)allyl;

D is oxygen or nonexistent, with the proviso that when D is nonexistent, $(CH_2)_m$ is bonded directly to a carbon on the ring;

X is an anionic counter ion, preferably selected from chloride, bromide, hydroxide, methosulphate, sulfate, sulfonate, carboxylate, phosphate, and phosphonate; and $R_{66}$ is H or alkyl.

Substantially free of the compound of Structure (VI) means that the monomer composition comprising the monomer of Structure (II) has preferably less than 8 mol %, has preferably less than 7 mol %, has preferably less than 6 mol %, more preferably less than 5 mol %, more preferably less than 3 mol %, more preferably less than 2 mol %, and most preferably has less than 1.5 mol % or is even completely free of the non-monomer compound of Structure (VI) relative to the total amount of naphthalimide compounds in the composition. This non-monomer compound of Structure (VI) cannot be polymerized but will still emit a fluorescent signal. Structure (II) is typically prepared by using allyl amine. This allyl amine can have impurities such as ammonia or alkyl amine, which leads to the impurities of (VI). By using a pure allyl amine the impurities of (VI) can be minimized. Therefore, the purity of allyl amine is preferably 95%, more preferably 98% and most preferably 99%.

Unless otherwise indicated, that a first substance is "substantially free" of a second substance, as used herein, means, as discussed above, that the first substance has preferably less than 8 mol %, has preferably less than 7 mol %, has preferably less than 6 mol %, more preferably less than 5 mol %, more preferably less than 3 mol %, more preferably less than 2 mol %, and most preferably has less than 1.5 mol % or is even completely free of the second substance relative to a 100% of the moles of the first substance.

In a preferred embodiment, the polymer comprises the monomer of Structure (I) wherein $R_4$ is hydroxy or is alkoxy selected from methoxy, ethoxy, n-propyloxy, isopropyloxy, n-butoxy, isobutoxy, and tert-butoxy; $R_{41}$ is H, and the polymer composition is substantially free of the compound of Structure (III). In an especially preferred subgenus of this embodiment, $R_3$ is selected from methallyl, (meth)acryl, 2-hydroxy-3-(meth)allyloxypropyl, 1-hydroxy-3-(meth)allyloxypropyl, 2-(hydroxy)-3-(ethoxy)-propyl, 3-(allyloxy)-2-(3-(allyloxy)-2-hydroxypropoxy)-propyl, vinylbenzyl, 3-(meth)acrylamidopropyl, and 2-(meth)acryloyloxy ethyl.

In a preferred embodiment, if the polymer contains a quaternized naphthalimide fluorescent monomer of Structure (I) and $R_4$ is alkoxy, alkoxyamine, alkyl, aryl, alkaryl, or $C_1$-$C_4$alk-O—$(CHR_5CH_2O—)_n$, and $R_{41}$ is H, the polymer is substantially free of halogenated derivatives of quaternized naphthalimide fluorescent monomers of Structure (IV)

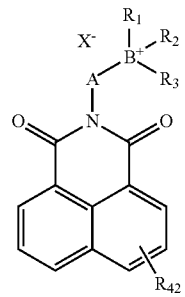

Structure (IV)

wherein A, B, X, $R_1$, $R_2$, and $R_3$ are defined as above and $R_{42}$ is halogen selected from chloro, bromo and iodo.

In another embodiment, the composition comprising the quaternized naphthalimide fluorescent monomer of Structure (II) which is added to the polymerization reaction mixture to make the water treatment polymer is substantially free of the halogenated impurities of Structure (V) especially when D is oxygen in Structure (II)

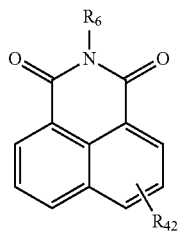

Structure (V)

where $R_6$ is defined above and $R_{42}$ is halogen selected from chloro, bromo and iodo.

Surprisingly if the monomer of Structure (I) is prepared from a precursor of the same structural formula but wherein $R_4$ or $R_{41}$ is halogen or the monomer of Structure (II) is prepared from a precursor of the same structural formula but wherein $R_{42}$ is halogen, these precursors if allowed to persist in the water treatment polymer are capable of suppressing the fluorescence signal of the inhibiting water treatment polymers and moving the emission and absorption to lower wavelengths, as illustrated in Example 17 herein. The halogen derivative is an intermediate in the synthesis of the derivatives of Structure (I) that contain for example, alkoxy groups and will be present as an impurity. In the method of controlling scale in a water system, the fluorescence is monitored at the maximum of absorption and emission of the quaternized fluorescent monomer of Structure (I) or Structure (II). If the quaternized naphthalimide monomer contains a halogen monomer as an impurity, some polymer chains will have the quaternized naphthalimide monomer and others the halogen derivative. Most importantly, since there would be signals coming from the polymer, significant amounts of halogen derivative impurity gives a lower signal at the wavelength at which the emitted signal is measured, and therefore inaccurate determination of the amount of polymer in the water system being treated. Also, since the signals are shifted to lower wavelengths, the fluorescent signal of the halogen derivative impurity may interfere with the signals of the azole components of the water treatment formulation which are routinely used as copper corrosion inhibitors. Therefore, these halogen impurities need to be minimized or eliminated. This is accomplished by monitoring the progress of the monomer synthesis reaction and continuing the reaction until the amount of halogen impurity is reduced to the desired level.

Substantially free of halogenated impurities of Structure (IV) or Structure (V) means that the monomer composition of Structure (I) or (II), respectively used to synthesize the polymer has preferably less than 10%, more preferably less than 5%, and most preferably has less than 2% or is even completely free of Structure (IV) or (V), as an impurity when measured by area percent using liquid chromatography.

A preferred fluorescent monomer is N-(3-dimethylaminopropyl)-4-methoxy-1,8-naphthalilmide, methallyl chloride quaternary salt.

Another preferred fluorescent monomer is N-(3-dimethylaminopropyl)-4-methoxy-1,8-naphthalimide, 1 or 2-hydroxy propyl quaternary salt.

Another preferred fluorescent monomer is N-(3-dimethylaminopropyl)-4-hydroxy-1,8-naphthalimide, 1 or 2-hydroxy propyl quaternary salt.

An especially preferred fluorescent monomer is (a) N-(3-dimethylaminopropyl)-4-methoxy-1,8-naphthalimide, 1 or 2-hydroxy-3-(meth)allyloxypropyl quaternary salt comprising less than 8 mol % of (b) N-(3-dimethylaminopropyl)-4-methoxy-1,8-naphthalimide, based on 100 mol % of (a).

The fluorescent monomers which are quaternized naphthalimide derivatives are present at less than 10 mol % of the polymer, preferably less than 5 mol % of the polymer, more preferably less than 2 mol % and most preferably less than 1 mol % of the polymer. The quaternized naphthalimide fluorescent monomers are present as at least 0.001 mol % of the polymer, preferably at least 0.005 mol % of the polymer, preferably at least 0.01 mol % and most preferably at least 0.05 mol % of the polymer.

A preferred monomer is a mixture of (a) monomer of Structure (I) wherein $R_3$ is 2-hydroxy-3-(meth)allyloxypropyl, (b) monomer of Structure (I) wherein $R_3$ is 1-hydroxy-3-(meth)allyloxypropyl, and a compound of:

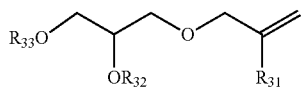

wherein $R_{31}$, $R_{32}$, and $R_{33}$ are independently H or alkyl;
in a molar ratio of (a):(b):(c) of 20:20:1 to 1:1:2.

(iii) Phosphorous-Containing Moieties

Optional phosphorus-containing moieties that can be incorporated into the polymer may be derived from any one or more of polymerizable phosphonate-containing monomers, phosphinic acid, phosphinate groups, phosphonic acid or phosphonate groups.

Polymerizable phosphonate monomers include without limitation vinyl phosphonic acid and vinyl diphosphonic acid, isopropenyl phosphonic acid, isopropenylphosphonic anhydride, (meth) allylphosphonic acid, ethylidene diphosphonic acid, vinylbenzylphosphonic acid, 2-(meth)-acrylamido-2-methylpropyl phosphonic acid, 3-(meth)acrylamido-2-hydroxypropylphosphonic acid, 2-methacrylamidoethylphosphonic acid, benzyl phosphonic acid esters and 3-(meth)allyloxy-2-hydroxypropylphosphonic acid.

Phosphinic acid or phosphinate groups may be incorporated in the polymer as phosphino groups by including in the polymerization mixture molecules having the structure

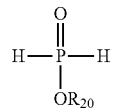

where $R_{20}$ is H, $C_1$-$C_4$alkyl, phenyl, alkali metal or an equivalent of an alkaline earth metal atom, an ammonium ion or an amine residue. These moieties which can incorporate phosphinic or phosphinate groups into the polymer include but are not limited to hypophosphorous acid and its salts, such as sodium hypophosphite.

Phosphonic acid or phosphonate groups may be incorporated in the polymer by including in the polymerization mixture molecules having the structure

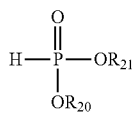

where $R_{20}$ or $R_{21}$ are independently H, $C_1$-$C_4$ alkyl, phenyl, alkali metal or an equivalent of an alkaline earth metal atom, an ammonium ion or an amine residue. These moieties include but are not limited to orthophosphorous acid and its salts and derivatives such as dimethyl phosphite, diethyl phosphite and diphenyl phosphite.

The one or more phosphorous moieties may be present in the water treatment polymer in the range of no greater than 20 mol %; in another aspect no greater than 10 mol %, in still another aspect no greater than 5 mol %, in still another aspect no greater than 3 mol %, and may not be present.

Copolymers of maleic acid and phosphino groups have superior carbonate inhibiting performance compared to the maleic homopolymers that do not have phosphino groups. Similarly, copolymers of maleic acid with acrylic acid and phosphino groups also provide good carbonate inhibition, with polymers having maleic contents in the range 50-99 mol % having better performance. Surprisingly, we have found that in either maleic acid/phosphino polymerization mixtures or maleic acid/acrylic acid/phosphino polymerization mixtures in which the maleic acid component is greater than 70 mol % of the polymerization mixture, the presence of quaternized naphthalimide fluorescent monomers of Structure (I) or Structure (II) will suppress the polymerization of maleic acid. This leads to large amounts of unreacted maleic acid which cannot be separated from the polymerization reaction product, rendering the resulting polymer solutions unusable. Therefore, if the polymerization reaction includes a phosphino group and at least part of the carboxylic acid monomer is maleic acid, then the maleic acid will be present as not greater than 70 mol % of the polymerization reaction mixture.

(iv) Sulfonic Acid Monomers

Optional water-soluble sulfonic acid monomers include but are not limited to one or more of 2-acrylamido-2-methyl propane sulfonic acid ('AMPS'), vinyl sulfonic acid, sodium (meth)allyl sulfonate, sulfonated styrene, (meth)allyloxybenzene sulfonic acid, sodium 1-(meth) allyloxy 2 hydroxy propyl sulfonate, ethoxylated allyl alcohol sulfonic acid, and combinations thereof, and their salts. In an embodiment, the sulfonic acid group can be incorporated in the polymer after polymerization. Examples of this type of sulfonic acid groups are sulfomethylacrylamide and sulfoethylacrylamide. For example, when the polymer contains acrylamide, the acrylamide moiety can react with formaldehyde and methanol to form sulfomethylacylamide.

In one embodiment, the amount of sulfonic acid monomer is less than 90 mol % of the polymer, more preferably less than 60 mol % of the polymer, more preferably less than 25 mol % of the polymer and most preferably less than 15 mol % of the polymer and may not be present.

In a preferred embodiment, if the polymer contains sulfonic acid groups, and the polymer is to be used for carbonate inhibition, then the polymer should contain a dicarboxylic acid, phosphorus moiety, or nonionic group to give superior carbonate inhibition.

(v) Nonionic Monomers

For purposes of this disclosure, a nonionic monomer is defined as a monomer that is not capable of developing a charge in water at any pH range. Nonionic monomers include water-soluble non-ionic monomers and low water solubility non-ionic monomers. The low water solubility non-ionic monomers are preferred.

In a preferred embodiment, the nonionic monomers are preferably substantially free of amine groups.

As used herein with respect to water-soluble non-ionic monomers, water-soluble means that the monomer has a water solubility of greater than 6 grams per 100 mls of water at 25° C.

Examples of water-soluble non-ionic monomers include (meth)acrylamide, N,N dimethylacrylamide, acrylonitrile, hydroxy alkyl (meth)acrylates such as hydroxyethyl (meth) acrylate and hydroxypropyl (meth)acrylate, vinyl alcohol typically derived from the hydrolysis of already polymerized vinyl acetate groups, 1-vinyl-2-pyrrolidone, vinyl lactam, allyl glycidyl ether, (meth)allyl alcohol, (meth)allyl alcohol ethoxylates, alkoxy polyalkylene glycols, especially, methoxy polyethylene glycol, and others.

In one embodiment, the nonionic monomer is a low water solubility nonionic monomer which is defined as a nonionic monomer that has a water solubility of less than 6 g per 100 mls at 25° C., preferably less than 3 g per 100 mls at 25° C.

Examples of a low water solubility nonionic monomer include but are not limited to $C_1$-$C_{18}$ alkyl esters, $C_2$-$C_{18}$ alkyl-substituted (meth)acrylamides, aromatic monomers, alpha-olefins, $C_1$-$C_6$ alkyl diesters of maleic acid and itaconic acid, vinyl acetate, glycidyl methacrylate, (meth) acrylonitrile and others. $C_1$-$C_{18}$ alkyl esters of (meth)acrylic acid include but are not limited to methyl methacrylate, methyl acrylate, ethyl acrylate, n-butyl acrylate, n-butyl methacrylate, t-butyl acrylate and t-butyl methacrylate, 2-ethyl hexyl (meth)acrylates, lauryl (meth)acrylate, stearyl (meth)acrylate and others. $C_2$-$C_{18}$ alkyl-substituted (meth) acrylamides include but are not limited to such as N, N-diethyl acrylamide, t-butyl acrylamide, and t-octyl acrylamide, and others. Aromatic monomers include but are not limited to styrene, alpha methylstyrene, benzyl (meth)acrylate and others. Alpha-olefins include, propene, 1-butene, diisobutylene, 1 hexene and others. The preferred nonionic low water solubility nonionic monomers are styrene, methyl (meth)acrylate, di isobutylene, vinyl acetate and t-butyl acrylamide. The more preferred nonionic low water solubility nonionic monomers are styrene, di isobutylene, and t-butyl acrylamide.

In one embodiment, the amount of water-soluble nonionic monomer is less than 90 mol % of the polymer, more preferably less than 60 mol % of the polymer, more preferably less than 25 mol % of the polymer and most preferably less than 15 mol % of the polymer and may not be present.

In one embodiment, the amount of low water solubility nonionic monomer is no greater than 90 mol % of the polymer, more preferably less than 60 mol % of the polymer, more preferably less than 25 mol % of the polymer and most preferably less than 15 mol % of the polymer and may not be present.

In a preferred embodiment, the polymer comprises a carboxylic acid monomer, the fluorescent monomers of this disclosure and a low water solubility nonionic monomer.

Polymerization

As indicated above, the water treatment polymer is prepared by a process comprising the following steps:
(a) polymerizing a polymerization mixture comprising:
   (i) at least one water-soluble carboxylic acid monomer, or salt or anhydride thereof, present in an amount of 10-99.999 mol % based on 100 mol % of the polymer;
   (ii) at least one quaternized naphthalimide fluorescent monomer of either (a) Structure (I) comprising less than 8 mol %, based on 100 mol % of Structure (I), of Structure (III) or (b) Structure (II) comprising less than 8 mol %, based on 100 mol % of Structure (II), of Structure (VI); and
(b) ensuring the fluorescent monomer is incorporated into the water treatment polymer to an extent equal to or greater than 90%.

In a preferred embodiment, the the fluorescent monomer is incorporated into the water treatment polymer to an extent of at least 90%, more preferably, at least 95%, more preferably at least 97%, more preferably at least 98%, more preferably at least 99% and most preferably is undetectable.

In another preferred embodiment, the fluorescent monomer has Structure (I) and has less than 3 mol %, or less than 2 mol %, in each case based on 100 mol % of Structure (I), of Structure (III); and the fluorescent monomer is incorporated into the water treatment polymer to an extent of at least 97%, or at least 98%, or at least 99%. In an especially preferred embodiment, the fluorescent monomer has Structure (I) and has less than 2 mol %, based on 100 mol % of Structure (I), of Structure (III); and the fluorescent monomer is incorporated into the water treatment polymer to an extent of at least 98%.

In another preferred embodiment, the fluorescent monomer has Structure (II) and has less than 3 mol %, or less than 2 mol %, in each case based on 100 mol % of Structure (II), of Structure (VI); and the fluorescent monomer is incorporated into the water treatment polymer to an extent of at least 97%, or at least 98%, or at least 99%. In an especially preferred embodiment, the fluorescent monomer has Structure (II) and has less than 2 mol %, based on 100 mol % of Structure (II), of Structure (VI); and the fluorescent monomer is incorporated into the water treatment polymer to an extent of at least 98%.

In another preferred embodiment, the fluorescent monomer is N-(3-dimethylaminopropyl)-4-methoxy-1,8-naphthalilmide, methallyl chloride quaternary salt; and the fluorescent monomer is incorporated into the water treatment polymer to an extent of at least 98%.

In another preferred embodiment, the fluorescent monomer is N-(3-dimethylaminopropyl)-4-methoxy-1,8-naphthalimide, 1 or 2-hydroxy propyl quaternary salt; and the fluorescent monomer is incorporated into the water treatment polymer to an extent of at least 98%.

In yet another preferred embodiment, the fluorescent monomer is N-(3-dimethylaminopropyl)-4-hydroxy-1,8-naphthalimide, 1 or 2-hydroxy propyl quaternary salt; and the fluorescent monomer is incorporated into the water treatment polymer to an extent of at least 98%.

In yet another especially preferred embodiment, the fluorescent monomer is (a) N-(3-dimethylaminopropyl)-4-methoxy-1,8-naphthalimide, 1 or 2-hydroxy-3-(meth)allyloxypropyl quaternary salt comprising less than 3 mol % of (b) N-(3-dimethylaminopropyl)-4-methoxy-1,8-naphthalimide, based on 100 mol % of (a); and the fluorescent monomer is incorporated into the water treatment polymer to an extent of at least 98%.

In one embodiment, the polymerization mixture additionally comprises:
   (iii) at least one phosphorous moiety present in an amount of 0-20 mol % based on 100 mol % of the water treatment polymer;
   (iv) at least one sulfonic acid monomer present in an amount of 0-40 mol % based on 100 mol % of the water treatment polymer; and
   (v) at least one non-ionic monomer present in an amount of 0-20 mol % based on 100 mol % of the water treatment polymer.

The polymerization of the fluorescent water treatment polymer is carried out in an appropriate solvent under standard polymerization conditions in the presence of an initiator, as is known in the art. In one aspect the reaction solvent can be water or a mixture of water and an alcohol such as isopropanol. The resulting polymer solution can be neutralized to a desired pH with an appropriate base. The neutralization can occur before, during or after polymerization or a combination thereof.

The polymer compositions are preferably prepared from a polymerization mixture in an aqueous medium in the presence of any initiator or initiating system capable of liberating free radicals under the reaction conditions employed. The free radical initiators are present in an amount ranging from about 0.01% to about 3% by weight based on total monomer weight. In an embodiment, the initiating system is soluble in water to at least 0.1 weight percent at 25° C. Suitable initiators include, but are not limited to, peroxides, azo initiators as well as redox systems, such as erythorbic acid, and metal ion based initiating systems. Initiators may also include both inorganic and organic peroxides, such as hydrogen peroxide, benzoyl peroxide, acetyl peroxide, and lauryl peroxide; organic hydroperoxides, such as cumene hydroperoxide and t-butyl hydroperoxide. In an embodiment, the inorganic peroxides, such as sodium persulfate, potassium persulfate and ammonium persulfate, are preferred. In another embodiment, the initiators comprise metal ion based initiating systems including Fe and hydrogen peroxide, as well as Fe in combination with other peroxides. Organic peracids such as peracetic acid can be used. Peroxides and peracids can optionally be activated with reducing agents, such as sodium bisulfite, sodium formaldehyde, or ascorbic acid, transition metals, hydrazine, and the like. A preferred system is persulfate alone such as sodium or ammonium persulfate or a redox system with iron and persulfate with hydrogen peroxide. Azo initiators, especially water-soluble azo initiators, may also be used. Water-soluble azo initiators include, but are not limited to, 2,2'-Azobis[2-(2-imidazolin-2-yl)propane]dihydrochloride, 2,2'-Azobis[2-(2-imidazolin-2-yl)propane]disulfate dihydrate, 2,2'-Azobis(2-methylpropionamidine)dihydrochloride, 2,2'-Azobis[N-(2-carboxyethyl)-2-methylpropionamidine]hydrate, 2,2'-Azobis{2-[1-(2-hydroxyethyl)-2-imidazolin-2-yl]propane}dihydrochloride, 2,2'-Azobis[2-(2-imidazolin-2-yl)propane], 2,2'-Azobis(1-imino-1-pyrrolidino-2-ethylpropane)dihydrochloride, 2,2'-Azobis{2-methyl-N-[1,1-bis(hydroxymethyl)-2-hydroxyethl]propionamide}, 2,2'-Azobis[2-methyl-N-(2-hydroxyethyl)propionamide] and others.

In a preferred embodiment, the the fluorescent monomer is incorporated into the water treatment polymer to an extent that the unreacted fluorescent monomer is as low as possible or undetectable. It is important to measure the amount of unreacted fluorescent monomer at the end of every polymerization reaction. It is important to take samples during the reaction and measure the unreacted fluorescent monomer over the reaction to ensure as even an incorporation of the fluorescent monomer as possible as well as ensuring minimum amount of unreacted fluorescent monomer. If the unreacted fluorescent monomer is higher than desired, it can be minimized in a number of ways. The feed rate of the fluorescent monomer relative to the other monomers needs to be adjusted to get even incorporation of the fluorescent monomer as well as make sure that the residual fluorescent monomer is minimized. If the fluorescent monomer concentration is increasing during the reaction, it means that the other monomers are preferably reacting with themselves. In that case shorten the fluorescent monomer feed time and/or lengthen the feed time of the other monomers. This gives the fluorescent monomer a better chance of reacting with the other (presumably more reactive) monomers. If however, the fluorescent monomer is being used up too quickly, the opposite needs to be done. In that case lengthen the fluorescent monomer feed time and/or shorten the feed time of the other monomers. This gives the fluorescent monomer a better chance of reacting with the other (presumably more less reactive) monomers.

One skilled in the art will realize that monomers such as acrylic acid or 2-acrylamido-2-methyl propane sulfonic acid are reactive and may leave unreacted fluorescent monomer especially if it has allylic groups. In this case, a part of the fluorescent monomer may be added to the charge and the other part fed by itself or with the other monomers or the monomers feed adjusted as detailed above.

In most cases, it is not preferred to have all of the fluorescent monomer in the initial charge. However, if both the fluorescent monomer as well as the other monomer are unreactive, then they both may go into the charge. Such is the case when the fluorescent monomer is allylic and the other monomer is unreactive such as maleic acid or allylic such as (meth)allyl sulfonate and others.

The initiator feed needs to be as long as the total monomer feed or may exceed the monomer feed by 15-30 minutes as explained in Polymer Example 29. Other ways to minimize the unreacted fluorescent monomer include but are not limited to increasing the temperature, increasing the concentration of the initiator relative to the total amount of monomer, or changing the type of initiator. In addition, the finding the optimum pH to react the fluorescent monomer may help. Adding a cosolvent such as an alcohol like an isopropyl alcohol will help especially if the unreacted fluorescent monomer contains an aromatic group ($R_3$ is vinyl benzyl in Structure (I)) attached to the double bond.

The molecular weight of the polymers may be controlled by various compounds used in the art including, for example, chain transfer agents such as mercaptans, ferric and cupric salts, bisulfites, and lower secondary alcohols, preferably isopropanol. The preferred weight average molecular weight is less than 50000, preferably less than 30000 and most preferably less than 20000. The preferred weight average molecular weight is greater than 1000, more preferably greater than 2000 and most preferably greater than 3000.

Neutralization

One skilled in the art will recognize that the carboxylic acid monomers are typically partially or completely neutralized before or during polymerization to increase reactivity of the monomers and improve their incorporation into the polymer. The polymers may be supplied as the acid or partially neutralized. This allows the water treatment formulator to formulate these polymers in low pH acidic formulations and high pH alkaline formulations.

Suitable neutralization agents include but are not limited to alkali or alkaline earth metal hydroxides, ammonia or amines. Neutralization agents can be sodium, potassium or ammonium hydroxides or mixtures thereof. Suitable amine neutralizing agents include but are not limited to ethanol amine, diethanolamine, triethanolamine and others.

While ammonia or amines can be utilized, in one embodiment the polymer is substantially free of ammonium or amine salts. Substantially free of ammonium or amine salts means that the acid groups in the polymer are neutralized with less than 10 mole percent ammonia or amine neutralizing agents, preferably less than 5 mole percent ammonia or amine neutralizing agents, more preferably less than 2 mole percent ammonia or amine neutralizing agents, and most preferably none at all. In another embodiment, ammonium or amine containing initiators, such as ammonium persulfate, or chain transfer systems are not utilized. Surprisingly, it has been found that the presence of ammonium or amine salts has a reduces the hypochlorite bleach stability of the polymer. The polymer is stable to hypochlorite bleach. In one embodiment, the polymer maintains hypochlorite bleach at pH 9 where more than half of the initial free chlorine is maintained after 1 hour at pH 9 at 25° C. in the presence of 10 ppm of active polymer.

Corrosion Inhibitors

Water treatment formulations may contain other ingredients such as corrosion inhibitors. These corrosion inhibitors can inhibit corrosion of copper, steel, aluminum, or other metals that may be present in the water treatment system. Azoles are typically used in these water treatment formulations as copper corrosion inhibitors. The benzotriazole is typically formulated in acidic formulations. The tolyl triazole is formulated in alkaline formulations. If a corrosion inhibitor is used, the formulator will choose a pH range suitable for the selected corrosion inhibitor, to achieve the desired solubility of these azoles, in the selected pH ranges. One skilled in the art will recognize that other azoles or non azole-containing copper corrosion inhibitors may be used in combination with these polymers. In addition, corrosion inhibitors that inhibit corrosion of other metals also can be used.

Tracers

One skilled in the art will recognize that the fluorescent water treatment polymers of the disclosed method can be used in formulations containing inert tracers. These tracers include but are not limited to, 2-naphthalene sulfonic acid, rhodamine, Fluorescein and 1,3,6,8-Pyrenetetrasulfonic acid, tetrasodium salt (PTSA). This allows for complete monitoring of the system as described in U.S. Pat. Nos. 5,171,450 and 6,280,635.

Water Treatment Formulations and Methods of Use

In accordance with the method herein, the polymer compositions may be dosed directly to the aqueous systems or may be formulated into various water treatment compositions which may then be dosed to the aqueous systems.

The fluorescent emissions of the dosed water system are then monitored. Such monitoring can be accomplished using known techniques as disclosed, for example, in U.S. Pat. Nos. 5,171,450, 5,986,030, and 6,280,635. Fluorescent monitoring such as in-line monitoring allows the user to monitor the amount of water treatment polymer used to mitigate scale in the aqueous system. This is especially useful in stressed systems where calcium and/or magnesium carbonate scaling is problematic.

A stressed system, as used herein means a system having a Langelier Saturation Index of at least 2.0. The Langelier Saturation Index or LSI is a common method used to predict the potential for calcium and/or magnesium carbonate precipitation in water. This index is based on the difference between the actual pH of the water in question and the saturation pH of calcium and/or magnesium carbonate, at the current conditions of the water (actual pH-saturation pH=LSI factor). As a result, an LSI factor of zero indicates that the water is at equilibrium. LSI factors greater than zero indicate that the water is supersaturated and will precipitate calcium and/or magnesium carbonate without some form of treatment. The greater the LSI, the greater the driving force for precipitation and scaling. Many factors can contribute to increasing LSI. Increasing pH values has a direct effect on increasing LSI. Increasing calcium and/or magnesium and alkalinity concentrations, increasing temperatures, and increasing conductivity all indirectly increase LSI factors by lowering the saturation pH of the water in question. LSI factors of greater than 2.0 are generally considered stressful conditions in the field, with factors from 2.5 to 3.0 considered extremely high stress. Minimizing the amount of orthophosphate requires the use of higher pH to minimize corrosion which leads to more highly stressed systems. Therefore, it is advantageous to have a low orthophosphate or no orthophosphate treatment system. For purposes of this disclosure, a low orthophosphate system means less than 10 ppm orthophosphate, more preferably less than 8 ppm orthophosphate and most preferably less than 6 ppm orthophosphate. A no orthophosphate system means that the orthophosphate is less than 1 ppm or preferably 0 ppm. Note that the orthophosphate that may be present in the water system as referred to above is distinct from the optional phosphino group moieties, phosphono group moieties and pendant phosphonate group moieties of component (iii) of the water-soluble fluorescent water treatment polymers of the disclosure.

The water treatment polymers as disclosed herein are effective in both non-stressed water systems and in stressed water systems having an LSI value of 2 or greater. In one aspect, use of the fluorescent water treatment polymers disclosed will achieve carbonate inhibition of at least 80% when the fluorescent water treatment polymer is dosed to a system having an LSI of 2 at an initial treatment rate of no greater than 100 ppm, in one embodiment at an initial treatment rate of no greater than 50 ppm, in one embodiment at an initial treatment rate of no greater than 25 ppm, in one embodiment at an initial treatment rate of no greater than 20 ppm, in one embodiment at an initial treatment rate of no greater than 10 ppm, in one embodiment at an initial treatment rate of no greater than 5 ppm, wherein all polymer concentrations are stated with respect to the amount of active polymer, and wherein carbonate inhibition is measured using the test protocol described in Example 8. In certain non-stressed aqueous systems where large volumes of water are continuously treated to maintain low levels of deposited matter, the polymers may be used at levels as low as 0.5 ppm. The upper and lower limits of the level of polymer used will be dependent upon the particular aqueous system to be treated. Accurately monitoring the amount of polymer in the water system by measuring the fluorescent emission allows for use of the minimum amount of polymer. This has both a favorable economic and environmental impact.

One skilled in the art will recognize that the fluorescent water treatment polymers of the disclosed method can be used in formulations containing inert tracers. These tracers include but are not limited to, 2-naphthalene sulfonic acid, rhodamine, Fluorescein and 1,3,6,8-Pyrenetetrasulfonic acid, tetrasodium salt (PTSA). This allows for complete monitoring of the system as described in U.S. Pat. Nos. 5,171,450 and 6,280,635.

Polymers for Flocculation and Coagulation

Polymers for flocculation and coagulation comprise at least one water-soluble cationic ethylenically unsaturated monomer and/or at least one water-soluble non-ionic monomer, as described above.

As used herein, the term "cationic ethylenically unsaturated monomer" means an ethylenically unsaturated monomer which is capable of developing a positive charge in an aqueous solution or always has a positive charge because it is quaternized. In an embodiment of the present disclosure, the cationic ethylenically unsaturated monomer has at least one amine functionality.

As used herein, the term "amine salt" means that the nitrogen atom of the amine functionality is covalently bonded to from one to three organic groups and is associated with an anion.

As used herein with respect to water-soluble non-ionic or cationic monomers for flocculation or coagulation purposes, "water-soluble" means that the monomer has a water solubility of greater than 6 grams per 100 mls of water at 25° C.

The cationic ethylenically unsaturated monomers include, but are not limited to, N,N dialkylaminoalkyl(meth)acrylate, N-alkylaminoalkyl(meth)acrylate, N,N dialkylaminoalkyl (meth)acrylamide and N-alkylaminoalkyl(meth)acrylamide, where the alkyl groups are independently $C_{1-18}$ linear, branched or cyclic moieties. Aromatic amine containing monomers such as vinyl pyridine may also be used. Furthermore, acyclic monomers such as vinyl formamide, vinyl acetamide and the like which generate amine moieties on hydrolysis may also be used. Preferably the cationic ethylenically unsaturated monomer is selected from one or more of N,N-dimethylaminoethyl methacrylate, tert-butylaminoethylmethacrylate, N,N-dimethylaminopropyl methacrylamide, 3-(dimethylamino)propyl methacrylate, 2-(dimethylamino)propane-2-yl methacrylate, 3-(dimethylamino)-2,2-dimethylpropyl methacrylate, 2-(dimethylamino)-2-methylpropyl methacrylate and 4-(dimethylamino)butyl methacrylate and mixtures thereof. The most preferred cationic ethylenically unsaturated monomers are N,N-dimethylaminoethyl methacrylate, tert-butylaminoethylmethacrylate and N,N-dimethylaminopropyl methacrylamide.

Examples of cationic ethylenically unsaturated monomers that are quaternized include but are not limited to: dimethylaminoethyl (meth)acrylate methyl chloride quaternary salt, dimethylaminoethyl (meth)acrylate benzyl chloride quaternary salt, dimethylaminoethyl (meth)acrylate methyl sulfate quaternary salt, dimethylamino propyl (meth)acrylamide methyl chloride quaternary salt, dimethylamino propyl (meth)acrylamide methyl sulfate quaternary salt, diallyl dimethyl ammonium chloride, (meth)acrylamidopropyl trimethyl ammonium chloride and others.

Examples of water-soluble non-ionic monomers for this purpose include (meth)acrylamide, N,N dimethylacrylamide, acrylonitrile, hydroxy alkyl (meth)acrylates such as hydroxyethyl (meth)acrylate and hydroxypropyl (meth)acrylate, vinyl alcohol typically derived from the hydrolysis of already polymerized vinyl acetate groups, 1-vinyl-2-pyrrolidone, vinyl lactam, allyl glycidyl ether, (meth)allyl alcohol, and others. The preferred monomer is (meth)acrylamide. High molecular weight polyarylamide polymers are typically produced by inverse emulsion polymerization. The fluorescent monomers of this disclosure can be incorporated into these polymers by dissolving these monomers into the acrylamide aqueous phase of the polymerization process.

When the polymers are used for coagulation or flocculation in a water treatment system, the method comprises the steps of:

(a) dosing the water system with the water treatment polymer; and (b) monitoring the fluorescent signal emitted from the water treatment system.

Polymers for Cleaning Applications

Polymers for cleaning applications are formed from at least one non-quaternized fluorescent naphthalimide derivative monomer, as herein described. In one embodiment, the disclosure relates to a method for determining whether a given location has been cleaned comprising the steps of:

(a) applying the polymer to the location;

(b) cleaning the location at least once; and (c) attempting to detect the presence of the fluorescent naphthalimide derivative remaining at the location after said cleaning, which, presence, if detected, indicates that additional cleaning is needed.

Ideally, if fluorescent naphthalimide derivative is detected as remaining at the location after cleaning, the location should be cleaned again as necessary until residual fluorescent naphthalimide derivative can no longer be detected, which failure to detect residual fluorescent naphthalimide derivative indicates the location is completely clean.

In one embodiment, the polymer is provided as a part of a film-forming composition that quickly dries on the surface to be cleaned, is transparent, and is easily removed, but not by incidental contact. The film deposited on the surface fluoresces under ultraviolet light due to the presence of the fluorescent naphthalimide derivative and can be easily visualized by inspection with a hand-held UV light emitting light source, such as a UV flashlight.

Suitable compositions and their preparation and use are described in US 2016/0002525, the entire contents of which are incorporated herein by reference. Typically, the composition will contain a solvent and a thickener. A ready-to-use formulation will in one embodiment contain from about 1 to about 30 wt. % of a fluorescent polymer; from about 60 to about 99 wt. % of a solvent; and from about 0.05 to about 1 wt. % of a thickener. Preferably, the ready to use composition comprises from about 4 to about 25 wt. % of a fluorescent polymer; from about 50 to about 95 wt. % of a solvent; and from about 0.1 to about 0.4 wt. % of a thickener. More preferably, the ready to use composition comprises from about 8 to about 16% of a fluorescent polymer; from about 67 to about 91 wt. % of a solvent; from about 0.1 to about 0.4 wt. % of the thickener; from about 0.1 to about 0.7 wt. % of a preservative; and an optional pH adjusting agent. The composition can also be formulated as a concentrate, in which case, the weight ratio of the fluorescent polymer to surfactant, fluorescent polymer to thickener, or other relative proportions of ingredients will remain the same as in the ready-to-use composition, but the composition will contain a lesser amount of solvent.

In one embodiment, the solvent is preferably selected from water, methanol, ethanol, n-propanol, isopropanol, n-butanol, 2-butanol, isobutanol, n-pentanol, amyl alcohol, 4-methyl-2-pentanol, 2-phenylethanol, n-hexanol, 2-ethylhexanol, benzyl alcohol, ethylene glycol, ethylene glycol phenyl ether, ethylene glycol mono-n-butyl ether acetate, propylene glycol, propylene glycol mono and dialkyl ethers, propylene glycol phenyl ether, propylene glycol diacetate, dipropylene glycol, dipropylene glycol mono and dialkyl ethers, tripropylene glycol mono and dialkyl ethers, 1,3-propanediol, 2-methyl-1,2-butanediol, 3-methyl-1,2-butanediol, glycerol, methyl formate, ethyl formate, n-propyl formate, isopropyl formate, n-butyl formate, methyl acetate, n-propyl acetate, isopropyl acetate, isobutyl acetate, methyl lactate, ethyl lactate, propyl lactate, dimethylformamide, n-propyl propionate, n-butyl propionate, n-pentyl propionate, amyl acetate, methyl ethyl ketone, methyl isobutyl ketone, diisobutyl ketone, ethylamine, ethanolamine, diethanolamine, formic acid, acetic acid, propanoic acid, butanoic acid, acetone, acetonitrile, acetaldehyde, dimethyl sulfoxide, tetrahydrofuran, or a mixture thereof.

In one especially preferred embodiment, the solvent comprises water. The water can be from any source, including deionized water, tap water, softened water, and combinations thereof. The amount of water in the composition ranges from about 40 to about 99 wt. %, preferably from about 60 to about 95 wt. %, and more preferably from about 70 to about 90 wt. %.

In one embodiment, the thickener is preferably selected from xanthan gum, guar gum, modified guar, a polysaccharide, pullulan, an alginate, a modified starch, hydroxypropyl cellulose, hydroxypropyl methyl cellulose, carboxymethyl cellulose, hydroxyethyl cellulose, hydrophobically modified hydroxyethyl cellulose, hydrophobically modified hydroxypropyl cellulose, a polyacrylate, a vinyl acetate/alcohol copolymer, casein, a urethane copolymer, dimethicone PEG-8 polyacrylate, poly (DL-lactic-co-glycolic acid), a polyethylene glycol, a polypropylene glycol, pectin, or a combination thereof.

The composition can also include surfactants, preservatives, pH adjusting agents, and combinations thereof.

Polymer Mixtures

One skilled in the art will recognize that the polymers of this invention can be used with polymers containing other fluorescent monomers. This is especially useful if two different polymers need to be detected. For example, if one of the polymers is used for phosphate scale and the other is used for carbonate scale, these two polymers can be detected if the fluorescent monomers are different and adsorb and emit at different wavelengths from each other. The polymers of this invention can be used in conjunction with polymers that incorporate of the fluorescent monomers such as (meth) allyl oxy pyranine and other pyranine derivatives as described in U.S. Non-Provisional patent application Ser. No. 16/635,828, the entire contents of which is hereby incorporated herein by reference. The polymers of this invention can be used in conjunction with polymers that incorporate coumarin, fluorescein, rhodamine, or Nile blue derivative monomers as described in U.S. Provisional Patent Application No. 63/116,428, the entire contents of which is hereby incorporated herein by reference.

Monomer Synthesis

The monomer synthesis is a multi-step process using 4-chloro-1,8,-naphthalic anhydride as the starting material. In the first step the anhydride is converted to an amide; this step may e carried out in a non-aqueous solvent such as toluene. The amide may then be substituted with other groups as may be desired in subsequent reaction steps, which can take place in alcohol-based solvent systems such as methanol or propanol. To minimize the presence of undesired intermediates as impurities in the final product, molar excesses of selected reactants can be used, and the progress of the reactions monitored to ensure that the reaction goes substantially to completion. Slow addition of reactants can also promote more complete conversion to the desired end product.

MONOMER EXAMPLE 1

Synthesis of N-(3-dimethylaminopropyl)-4-methoxy-1,8-naphthalimide, methallyl chloride quaternary salt. In Structure (I): $R_4$ and $R_{41}$ are independently selected from H, methoxy, or are both methoxy, $R_1$ and $R_2$ are both $CH_3$ ($C_1$ alkyl), $R_3$ is methallyl, A is propyl ($C_3$ alkyl), B is nitrogen and X is chloride. The monomer has a minimal residual N-(3-dimethylaminopropyl)-4-methoxy-1,8-naphthalimide (corresponding to Structure (III)). In Structure (III): $R_4$ and $R_{41}$ are independently selected from H, methoxy, or are both methoxy, $R_1$ and $R_2$ are both $CH_3$ ($C_1$ alkyl), A is propyl ($C_3$ alkyl) and B is nitrogen.

Step 1: Synthesis of N-(3-dimethylaminopropyl)-4-chloro-1,8-naphthalimide

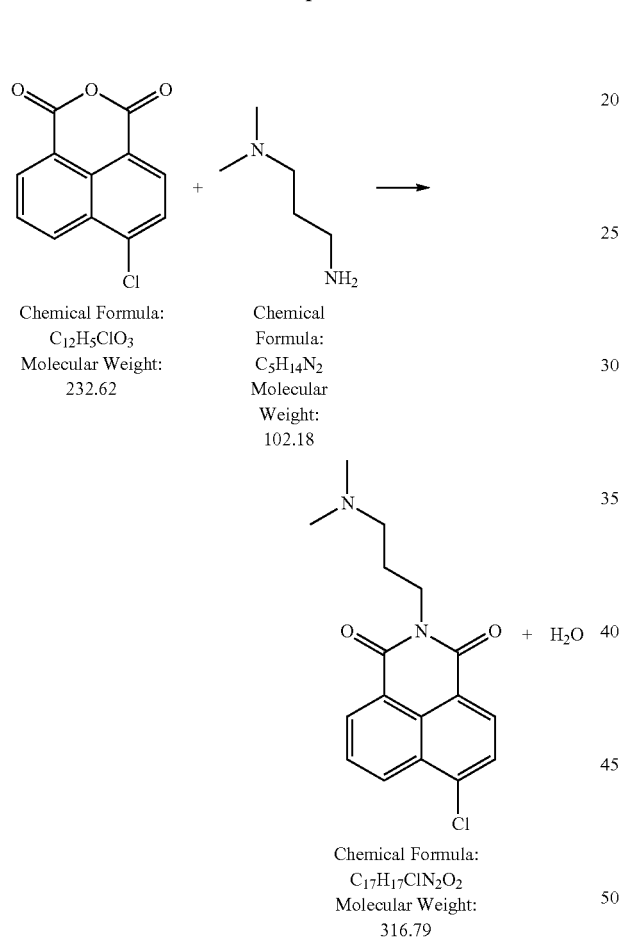

A flask equipped with an addition funnel nitrogen inlet/outlet, thermocouple, magnetic stirrer, and heating mantle, 48.9 g of 4-chloro-1,8-naphthalic anhydride (0.2102 mol) (>94% purity obtained from Alfa Aesar) and 700 mL of toluene was added. LC analysis indicated that it had 3 area % of 4,5-dichloro-1,8-naphthalic anhydride fraction. Next, 22.6 g of N-dimethylaminopropylamine (DMAPA) (0.2212 mol) was placed in the addition funnel and was slowly added to the flask over 15 minutes at room temperature. An exotherm from 22° C. to 32° C. was observed during the addition.

The addition funnel was replaced with a Dean-Stark distillation head. The reaction mixture was then heated to 45° C. for 30 minutes, and the temperature was gradually raised to 60° C. for 45 minutes, 70° C. for 69 minutes, 90° C. for 140 minutes, 110° C. for 135 minutes, and 115° C. for 85 minutes. The reaction mixture was checked with thin layer chromatography (TLC) at different points during the reaction and stopped when the anhydride was no longer present. A total of 1.6 grams of water was distilled off.

The solvent was stripped by rotary evaporation, and after vacuum treatment of the resulting wet solid gave 65.6 g of a yellow dry powder (0.2070 mol, 99% yield). $^1$H-NMR spectrum of the product confirmed the target structure.

Step 2: Synthesis of N-(3-dimethylaminopropyl)-4-methoxy-1,8-naphthalimide

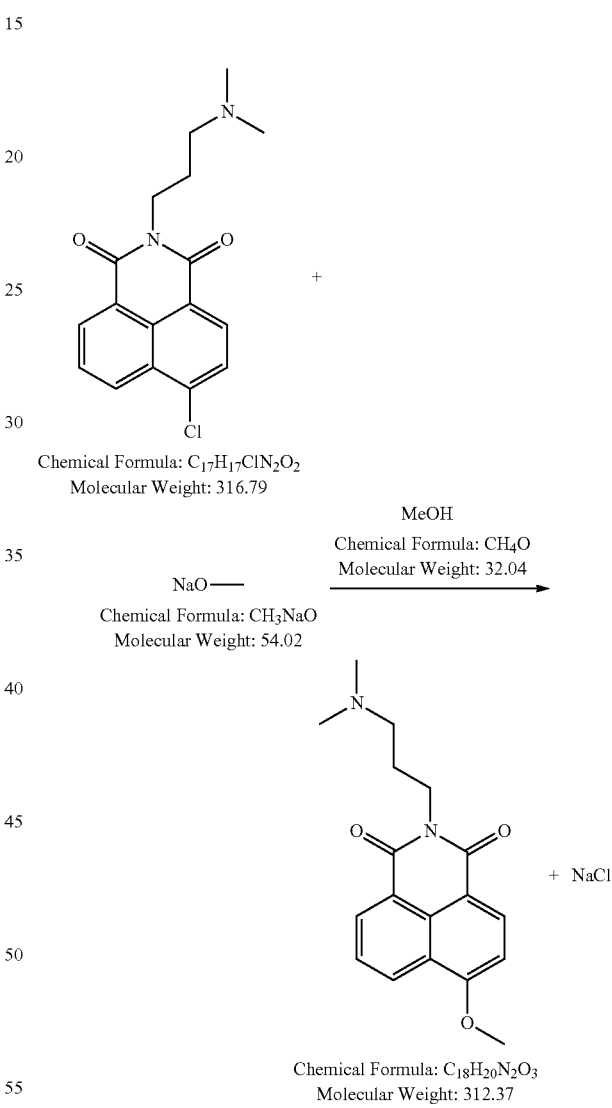

30.76 g of N-(3-dimethylaminopropyl)-4-chloro-1,8-naphthalimide (0.0971 mol) from Step 1 and 275 g of methanol were placed in a flask equipped with a dropping funnel, nitrogen inlet/outlet, magnetic stirrer, thermocouple and heating mantle. The mixture was heated to 50° C. and became a homogeneous solution. 28 mL of 5.4 M sodium methoxide in methanol solution (0.1512 mol) was placed in the dropping funnel. The sodium methoxide solution was slowly added to the flask in 45 minutes. The reaction temperature was raised to 65° C. The reaction was kept stirred at this temperature for 10 hours, TLC analysis was performed several times during this time to monitor the reaction progress. An additional 8 mL of sodium methoxide solution (0.0432 mol) was added because the reaction appeared to be incomplete based on the TLC analysis. In total 0.1944 moles of sodium methoxide were used, to provide a molar excess of 2:1.

The reaction mixture was cooled down and 5.2 g of acetic acid (0.0872 mol) was added to neutralize the remaining sodium methoxide. A slurry was obtained after stripping the solvent from the reaction mixture using a rotary evaporator. 200 mL of ethyl acetate was added to this slurry and the resulting mixture was vacuum filtered to remove insoluble salts. Ethyl acetate was evaporated from the filtrate to obtain a yellow solid. The final product was obtained by recrystallization of the yellow solid from either heptane/ethyl acetate solution or heptane solution. Three recrystallization crops were obtained: 1st crop 15.32 grams from heptane/ethyl acetate, 2nd crop 8.92 grams from heptane, 3rd crop 2.8 grams from heptane; total 27.9 grams, 0.0893 mol, 92% yield. $^1$H-NMR spectrum confirmed the target structure.

Step 2: Synthesis of N-(3-dimethylaminopropyl)-4-methoxy-1,8-naphthalilmide, Methallyl Chloride Quaternary Salt

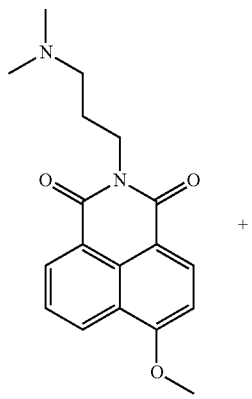

Chemical Formula: C$_{18}$H$_{20}$N$_2$O$_3$
Molecular Weight: 312.37

+

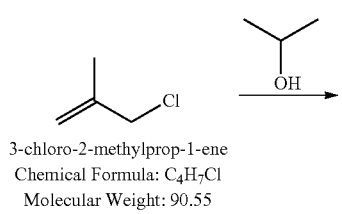

3-chloro-2-methylprop-1-ene
Chemical Formula: C$_4$H$_7$Cl
Molecular Weight: 90.55

-continued

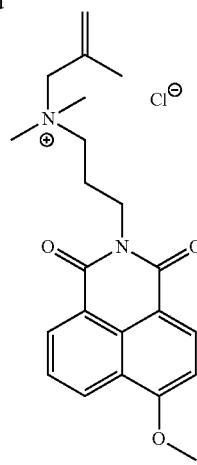

Chemical Formula: C$_{22}$H$_{27}$ClN$_2$O$_3$
Molecular Weight: 402.92

26.88 g of N-(3-dimethylaminopropyl)-4-methoxy-1,8-naphthalimide (0.0861 mol) from Step 2, 1.24 g of sodium bicarbonate (0.0148 mol) and 150 g of isopropanol were placed in a flask equipped with a magnetic stirrer, thermocouple, nitrogen inlet/outlet, and dropping funnel. The mixture was heated to 55° C. The mixture became homogeneous at this temperature.

12.49 g of methallyl chloride (0.1349 mol) was placed in the dropping funnel and added to the reaction at 55° C. over 30 minutes. The temperature of the reaction was then raised to 65° C. and stirred for 3 hours at this temperature. An aliquot was taken and the solvent was stripped. The HCl titration of this sample indicated 0.3 meq/g free amine (3.2 meq/g for the starting amine). This calculates to 9.3% of the starting amine being unreacted.

The reaction was stirred for another 2 hours at 65° C., then the HCl titration indicated 0.27 meq/g. 5.55 g of methallyl chloride (0.0613 mol) was added to the reaction mixture, and the mixture was stirred for another 2.5 hours at 65° C. The HCl titration indicated 0.11 meq/g free amine. This calculates to 3.4% of the starting amine being unreacted. This illustrates how the amine of Structure (III) can be minimized by continuously monitoring the reaction for the amine and adding additional reactants if necessary.

After cooling down, the sodium bicarbonate was filtered off, and the solvent was stripped to reduce the volume of the resultant solution to about one third of the original volume. This solution was left at room temperature to recrystallize the product overnight. The crystallized material was collected by vacuum filtration, and the collected yellow solid was dried under vacuum. An orange/yellow solid, 29.7 grams (86% recovery yield) was obtained. $^1$H-NMR analysis indicated that the obtained material conformed with the target structure.

The sample was analyzed by HPLC/UV 300 nm/ELSD/MS after dissolution in methanol at about 8 mg/ml, and was found to include N-(3-dimethylaminopropyl)-4-methoxy-1,8-naphthalimide, methallyl chloride quaternary salt (87.1% by area), N-(3-dimethylaminopropyl)-1,8-naphthalimide, methallyl chloride quaternary salt (4.3% by area), N-(3-dimethylaminopropyl)-4-methoxy-1,8-naphthalimide (corresponding to Structure (III)) (1.41% by area), N-(3-dimethylaminopropyl)-chloro-1,8-naphthalilmide, methallyl chloride quaternary salt (corresponding to Structure (IV)) (1.5% by area), and N-(3-dimethylaminopropyl)-4,5-dimethoxy-1,8-naphthalilmide, methallyl chloride quaternary salt (3.01% by area), the latter corresponding to Structure (I) where $R_1$ or $R_2$ is methyl, $R_3$ is (meth)allyl, A is propyl, B is nitrogen, X is Cl$^-$ counter ion and $R_4$ and $R_{41}$ are both methoxy. This is produced from the 4,5-dichloro-1,8-naphthalic anhydride fraction in the starting 4-chloro-1,8-naphthalic anhydride material. The fraction where $R_4$ and $R_{41}$ are both methoxy has a stronger fluorescence signal the end of main product where $R_4$ and $R_{41}$ are H or methoxy. Therefore, a higher fraction of this moiety is desirable. Hence, a higher fraction of 4,5-dichloro-1,8-naphthalic anhydride fraction in the starting 4-chloro-1,8-naphthalic anhydride material is preferable.

HPLC Conditions

| Column | Agilent Porashell C8 4 mm × 50 mm |
|---|---|
| Time 0 | 100% 25 mm ammonium formate pH 3.0 in 20% acetonitrile/0% methanol |
| Time 10 | 30% 25 mm AF pH 3.0 in 20% acetonitrile/70% methanol |
| Flow Rate | 1.0 ml/min |

Positive Ion Detection for Mass Spec

MONOMER EXAMPLE 2

Synthesis of N-(3-dimethylaminopropyl)-4-(meth) allyloxy-1,8-naphthalimide, 2-hydroxy Propyl Quat In Structure (I): $R_4$ is (meth)allyloxy, $R_{41}$ is H, B is N, A is propyl, $R_1$ and $R_2$ are methyl, $R_3$ is 2 hydroxy propyl and X is hydroxide counter ion

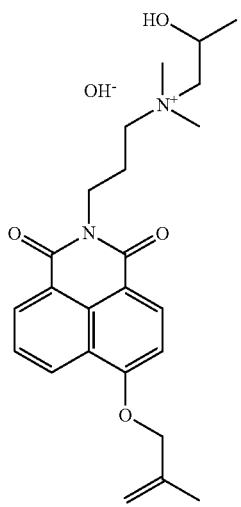

Step 1: Synthesis of N-(3-dimethylaminopropyl)-4-chloro-1,8-naphthalimide

See Step 1 of Monomer Example 1

Step 2: Synthesis of N-(3-dimethylaminopropyl)-4-(meth)allyloxy-1,8-naphthalimide Potassium hydroxide (7.83 g, 0.1400 mol) and (meth)allyl alcohol (388.8 g, 5.40 mol) are placed in a flask equipped with a nitrogen inlet/outlet, thermocouple, heating mantle, and mechanical stirrer. The mixture is stirred at 50° C. to dissolve potassium hydroxide. After potassium hydroxide is completely dissolved, N-(3-dimethylaminopropyl)-4-chloro-1,8-naphthalimide (65.6 g, 0.194 mol) is added to the solution as a powder in one shot. The reaction was heated at 55° C. and monitored by TLC analysis. After 3 hours at temperature, TLC analysis indicated incomplete reaction. Additional potassium hydroxide (3.38 g, 0.0602 mol) is added and the reaction is heated further to 60° C. Additional sampling called for four more additions of potassium hydroxide (Total KOH added=27.58 g, 0.4915 mol) and the reaction is at 55-60° C. for a total of 22 hours. After cooling down to room temperature, the product is precipitated out from solution. The solid product is collected by vacuum filtration and the flask was washed with isopropanol. The solids are collected and washed with water to remove potassium chloride salts that is formed. The mixture was once again filtered and the resulting solids are dried with vacuum, yielding a powder product.

Step 3: Synthesis of Quat Derivative

N-(3-dimethylaminopropyl)-4-(meth)allyloxy-1,8-naphthalimide, 2-hydroxy Propyl Quat A 100 ml round bottom flask is charged with 3.38 g of the powdered N-(3-dimethylaminopropyl)-4-(meth)allyloxy-1,8-naphthalimide (9.6 mmol) from Step 2 above, 40 g of water and 1.16 g of propylene oxide (20 mmol) is then added. The mixture is heated to 60° C. for 4 hours to give a water-soluble clear product.

MONOMER EXAMPLE 3

4-methoxy-N-(3-dimethylaminopropyl)-1,8-naphthalimide, 1 or 2-hydroxy-3-allyloxy propyl, quaternary salt. In Structure (I): $R_4$ and $R_{41}$ are independently selected from H, methoxy, or are both methoxy, $R_1$ and $R_2$ are both $CH_3$ ($C_1$ alkyl), $R_3$ is 2-hydroxy-3-(meth)allyloxypropyl or 1-hydroxy-3-(meth)allyloxypropyl, A is propyl ($C_3$ alkyl), B is nitrogen and X is hydroxide. The monomer has a minimal residual N-(3-dimethylaminopropyl)-4-methoxy-1,8-naphthalimide (corresponding to Structure (III)) using a 100% excess allyl glycidyl ether. In Structure (III): $R_4$ and $R_{41}$ are independently selected from H, hydroxy, or are both hydroxy, $R_1$ and $R_2$ are both $CH_3$ ($C_1$ alkyl), A is propyl ($C_3$ alkyl) and B is nitrogen.

Step 3: Synthesis of N-(3-dimethylaminopropyl)-4-chloro-1,8-naphthalimide

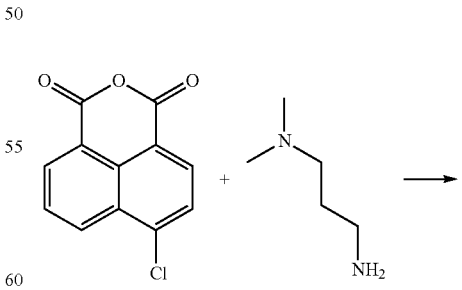

Chemical Formula: $C_{12}H_5ClO_3$
Molecular Weight: 232.62

Chemical Formula: $C_5H_{14}N_2$
Molecular Weight: 102.18

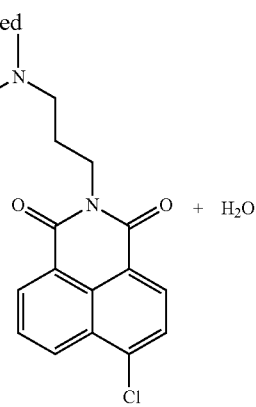

Chemical Formula:
C₁₇H₁₇ClN₂O₂
Molecular Weight:
316.79

A flask equipped with an addition funnel nitrogen inlet/outlet, thermocouple, magnetic stirrer, and heating mantle, 48.9 g of 4-chloro-1,8-naphthalic anhydride (0.2102 mol) (>94% purity obtained from Alfa Aesar) and 700 mL of toluene was added. The 4-chloro-1,8-naphthalic anhydride was found to have approximately 3 area % of 4,5-chloro-1,8-naphthalic anhydride by LC. The 4,5-chloro-1,8-naphthalic anhydride will produce a monomer structure where $R_4$ and $R_{41}$ are both methoxy which has a stronger fluorescence signal then a monomer where $R_4$ and $R_{41}$ are independently selected from H and methoxy. Therefore, it is advantageous to have a higher fraction of 4,5-chloro-1,8-naphthalic anhydride in the starting 4-chloro-1,8-naphthalic anhydride material. Next, 22.6 g of N-dimethylaminopropylamine (DMAPA) (0.2212 mol) was placed in the addition funnel and was slowly added to the flask over 15 minutes at room temperature. An exotherm from 22° C. to 32° C. was observed during the addition.

The addition funnel was replaced with a Dean-Stark distillation head. The reaction mixture was then heated to 45° C. for 30 minutes, and the temperature was gradually raised to 60° C. for 45 minutes, 70° C. for 69 minutes, 90° C. for 140 minutes, 110° C. for 135 minutes, and 115° C. for 85 minutes. The reaction mixture was checked with thin layer chromatography (TLC) at different points during the reaction and stopped when the anhydride was no longer present. A total of 1.6 grams of water was distilled off.

The solvent was stripped by rotary evaporation, and after vacuum treatment of the resulting wet solid gave 65.6 g of a yellow dry powder (0.2070 mol, 99% yield). ¹H-NMR spectrum of the product confirmed the target structure.

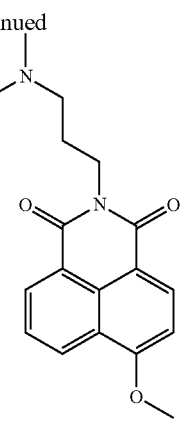

Step 2: N-(3-dimethylaminopropyl)-4-chloro-1,8-naphthalimide 30.21 grams (0.0954 mol) (from Step 1 above) and methanol (250 grams) were placed in a flask equipped with a dropping funnel, nitrogen inlet/outlet, magnetic stirrer, thermocouple and heating mantle. The mixture was heated to 65° C. and became a homogeneous solution. 5.4 M Sodium methoxide in methanol solution 36 mL (0.1944 mol) was placed in the dropping funnel. The sodium methoxide solution was slowly added to the flask over 45 minutes. The reaction was stirred at this temperature for 2 hours, TLC analysis was performed several times during this time to see the reaction progress. Additional 6 mL of sodium methoxide solution (0.0324 mol) was added based on the TLC analysis. The reaction was heated for another 4 hours. TLC analysis showed virtually no starting material.

After cooling down the reaction mixture, acetic acid (7.53 grams, 0.1255 mol) was added to neutralize. The solvent was evaporated to afford thick slurry. Ethyl acetate about 100 mL was added to this slurry and the resulting mixture was vacuum filtered to remove insoluble salts, and the salts were washed with 50 mL of ethyl acetate. The combined filtrate was concentrated by rotary evaporation to half of the original volume. Heptane 100 mL was added for recrystallization. 22.62 grams of the product was obtained from the recrystallization (76% recovery yield).

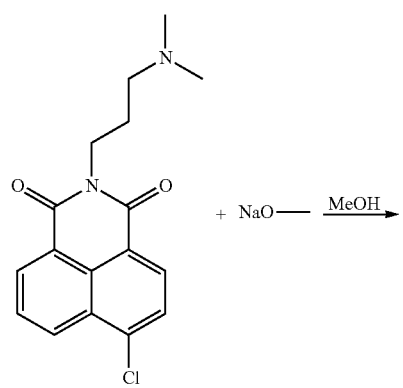

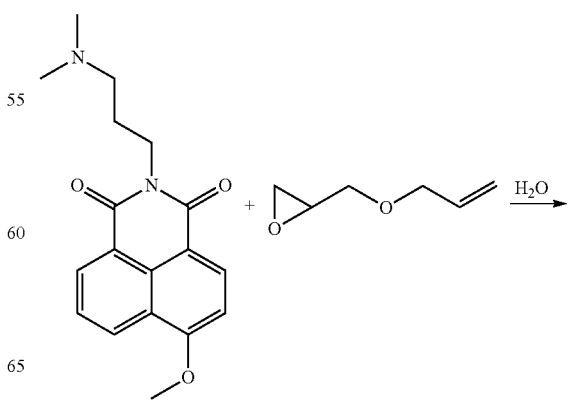

-continued

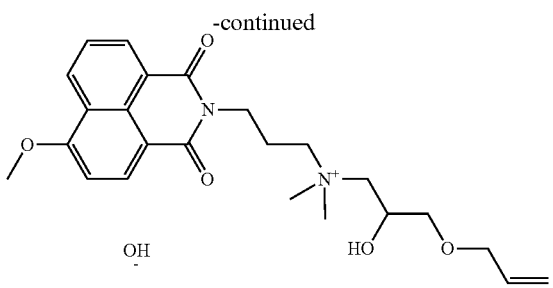

Step 3: N-(3-dimethylaminopropyl)-4-methoxy-1,8-naphthalimide (from Step 2 above, 9.98 grams, 0.03683 mol) and DI water (101.5 grams) were placed in a flask equipped with a thermocouple, heating mantle, nitrogen inlet/outlet, and magnetic stir bar. The mixture was then heated to 60° C., the mixture became a yellow suspension. Allyl glycidyl ether (AGE, Acros A0384473, >99% purity COA stated 99.9% purity, 7.21 grams, 0.0632 mol) was placed in a syringe and slowly added to the flask over 50 minutes. The reaction mixture turned red and became homogeneous, and heating was stopped 2 hours after the completion of AGE addition.

LC data indicates that the desired monomer was 70.6 area % and starting N-(3-dimethylaminopropyl)-4-methoxy-1,8-naphthalimide was 3.7 area %. It is important to analyze the reaction by LC or TLC or any other convenient means, towards the end of the reaction to make sure that the free amine content is low. If it is not, keep adding AGE till the free amine content is below a desired level. The molar amount of amine based on the total moles of monomer is them determined by $^{13}$C NMR. The LC or TLC methods are approximate and the NMR method used below can accurately measure the mol % and while longer to perform is the preferred method to determine the final composition. However, one skilled in the art will realize that the LC or TLC methods can be calibrated by the NMR method and be used to ensure that a minimum amount of Structure (III) remains in the final product especially on a commercial scale.

Figure 2:
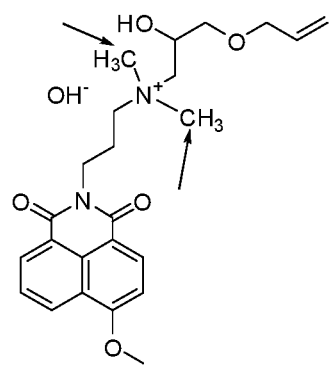
FIG. 2 depicts the chemical structure of 4-methoxy-N-(3-dimethylaminopropyl)-1,8-naphthalimide, 2-hydroxy-3-allyloxy propyl, quaternary ammonium hydroxide.
Figure 3:
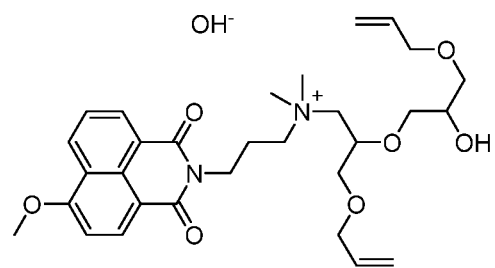
FIG. 3 depicts the chemical structure of 4-methoxy-N-(3-dimethylaminopropyl)-1,8-naphthalimide, 3-(allyloxy)-2-(3-(allyloxy)-2-hydroxypropoxy)-propyl, quaternary ammonium hydroxide.
Figure 4:
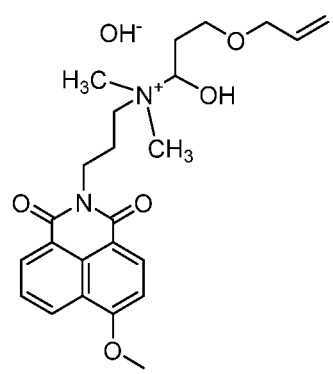
FIG. 4 depicts the chemical structure of 4-methoxy-N-(3-dimethylaminopropyl)-1,8-naphthalimide, 1-hydroxy-3-allyloxy propyl, quaternary ammonium hydroxide.

The mol % of N-(3-dimethylaminopropyl)-4-methoxy-1,8-naphthalimide of Structure (III) (FIG. 1), based on the total mol % of polymerizable quaternary moieties was below the limit of detection by $^{13}$C NMR which is 1.2 mol % (see NMR method below). Therefore, the mol % of N-(3-dimethylaminopropyl)-4-methoxy-1,8-naphthalimide of Structure (III), based on the total mol % of polymerizable quaternary moieties of Structure (I) was less than 1.2 mol %. The total moles of polymerizable quaternary moieties of Structure (I) are the sum of the moles of all forms of the monomer that have a quaternary charge and can be polymerized or incorporated into the polymer by other means such as chain transfer. These polymerizable quaternary moieties or monomers include moieties that have one polymerizable double bond (FIGS. 2 and 4), moieties that have 2 polymerizable double bonds (FIG. 3) or have a secondary alcohol which can be incorporated into the polymer as a chain transfer agent.

NMR Method Details:

The samples were prepared as aqueous solutions using 1 mL of the sample with 150 μL D$_2$O added and were analyzed by $^{13}$C NMR.

The $^{13}$C NMR spectra were acquired on a Varian 400 MHz NMR spectrometer using a 45° pulse, a 5 s relaxation delay, and 12,500 scans. The spectra were acquired with inverse gated decoupling to eliminate the NOE (nuclear Overhauser effect) and obtain quantitative spectra. The parameters used are shown in the table below.

The integral of the two methyl groups of the quaternary moieties (see methyl groups illustrated by arrows in FIG. 2) represented by the peaks between 52.5 and 51.0 ppm, was set to 200 and the NMe$_2$ carbons of the amine (see methyl groups illustrated by arrows in FIG. 1), represented by the peak around 44 ppm, were used to calculate the mol % of the amine of Structure (III) relative to the total mol % of polymerizable quaternary moieties of Structure (I).

| $^{13}$C NMR Experimental Parameters | | | |
|---|---|---|---|
| Spectrometer frequency | 100.532 MHz | Transmitter offset (tof) | 1530.7 Hz |
| Pulse sequence | s2pul | Spectral width (sw) | 25000.0 Hz |
| Acquisition time (at) | 1.311 sec | Data points (np) | 65536 |
| Transmitter power (tpwr) | 62 db | Pulse width (pw) | 3.15 μsec |
| Pulse delay (d1) | 5.00 sec | Temperature (temp) | 30° C. |
| Line broadening (lb) | 3.0 Hz | Number of scan (nt) | 12500 |

Results

The limit of detection was determined by spiking the Monomer Example 3 with 10, 5, 2, 1 and 0.5 weight % amine of Step II of Monomer Example 3.

Figure 5:
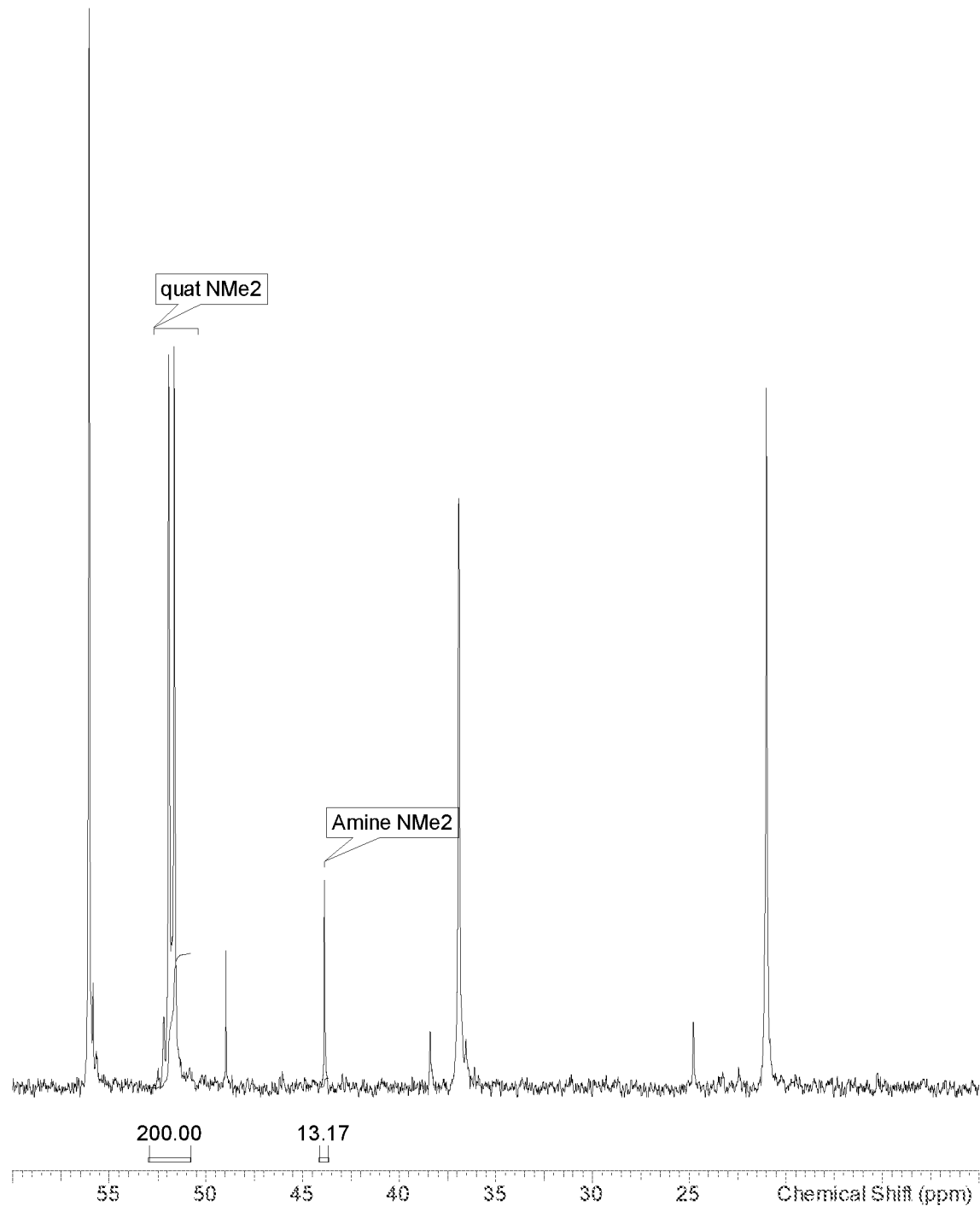
FIG. 5 depicts a portion of the $^{13}$C NMR spectrum of Monomer Example 3 sample, spiked with 5 weight % amine.

The $^{13}$C NMR spectrum of the sample spiked with 5 weight % amine (see FIG. 5) reveals that the NMe$_2$ carbons of the amine appear around 44 ppm.

Figure 6:
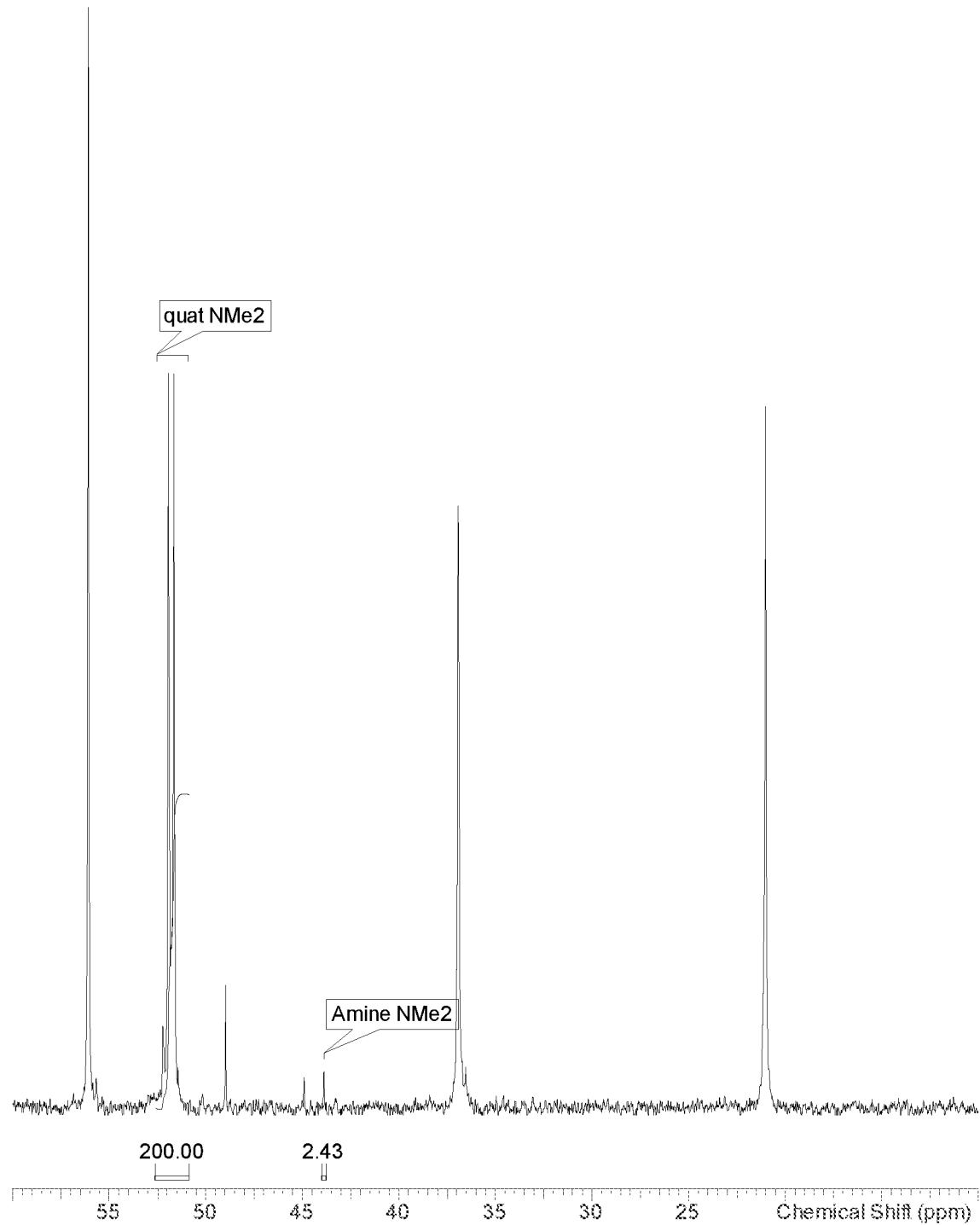
FIG. 6 depicts another portion of of the $^{13}$C NMR spectrum of Monomer Example 3 sample, spiked with 1 weight % amine
Figure 7:
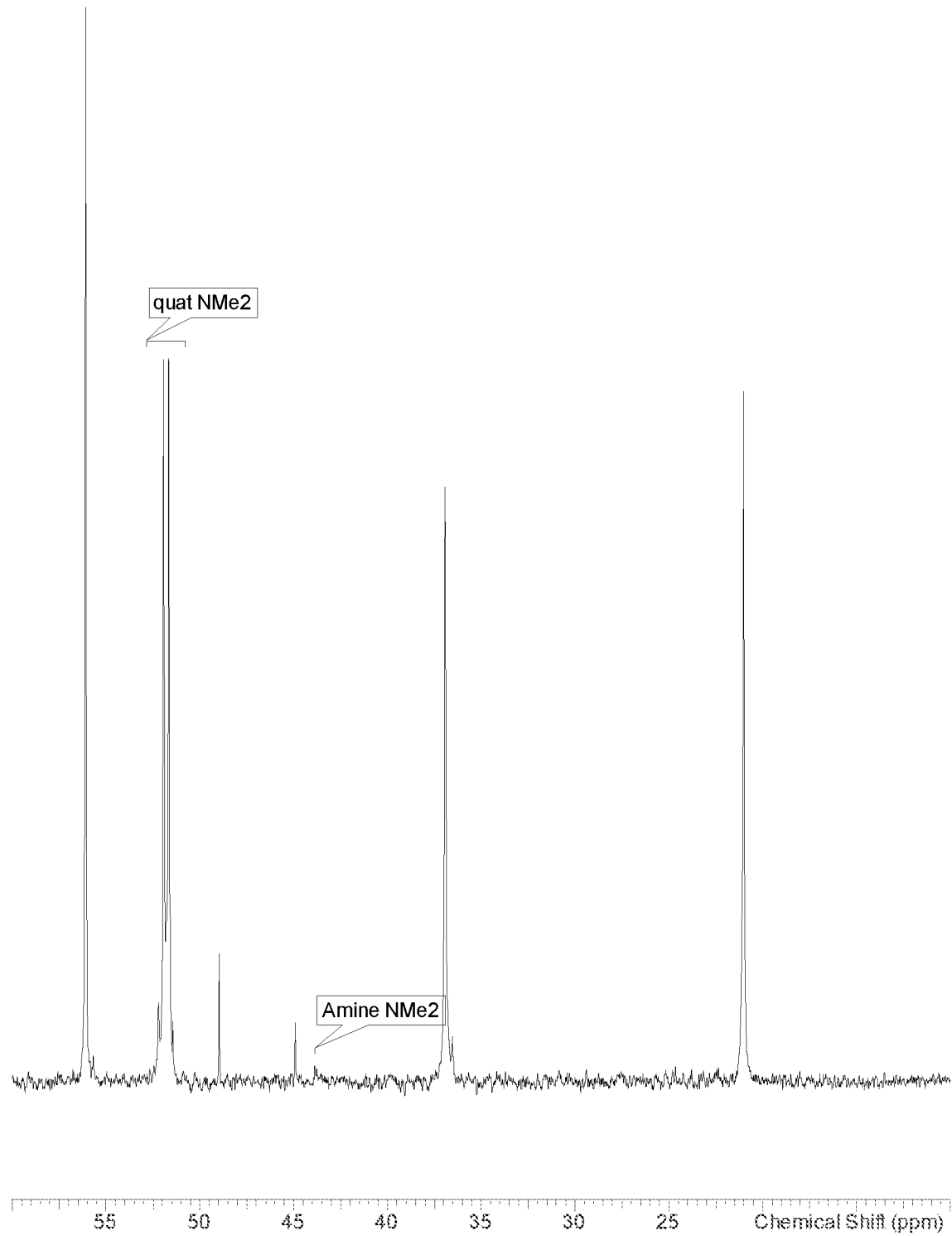
FIG. 7 depicts another portion of the $^{13}$C NMR spectrum of Monomer Example 3 sample, spiked with 0.5 weight % amine.

The amine peak is barely detectable in the $^{13}$C NMR spectrum of the 1 weight sample (see FIG. 6) and is in the noise in the $^{13}$C NMR spectrum of the 0.5 weight sample (see FIG. 7).

The mol % of N-(3-dimethylaminopropyl)-4-methoxy-1,8-naphthalimide amine relative to total mol % of polymerizable quaternary moieties of Structure (I) in the 1 weight spiked sample was calculated from the spectrum to be 1.2 mol %, making this the limit of detection.

Figure 8:
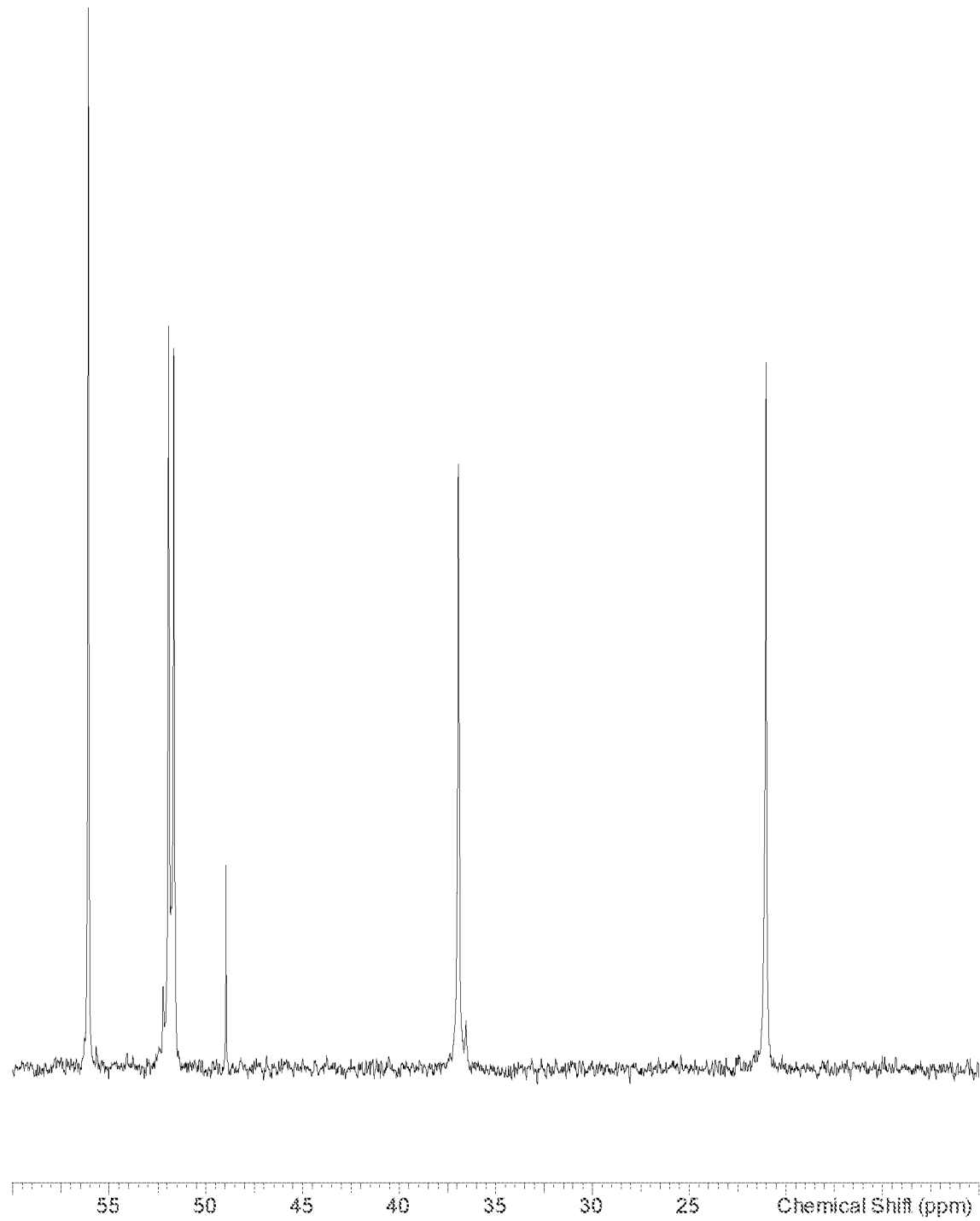
FIG. 8 depicts another portion of the $^{13}$C NMR spectrum of Monomer Example 3.

The $^{13}$C NMR spectrum of the sample of Monomer Example 3 shows no peak for the amine (see FIG. 8). Therefore, the mol % of N-(3-dimethylaminopropyl)-4-methoxy-1,8-naphthalimide amine of Structure (III) based on a total of mol % of polymerizable quaternary moieties of Structure (I) in Monomer Example 3 is well below 1.2 mol %.

MONOMER EXAMPLE 3A (COMPARATIVE)

Example 6 in U.S. Pat. No. 6,645,428 discloses a method to make 4-methoxy-N-(3-dimethylaminopropyl)-1,8-naphthalimide, 2-hydroxy-3-allyloxy propyl, quaternary salt monomer. We repeated Example 6 of this publication except we did not strip the solvent at the end of Step 2:

Step 1: A 500 ml reactor equipped with heating mantle, temperature controller, condenser and stirrer was charged with 40.1 g of glacial acetic acid, 10.5 g of 3-dimethylaminopropyl amine and 23.3 g of 4-chloro-1,8-naphthalic anhydride. All of the solids dissolved to give an amber colored solution. The reaction was heated to 122° C. and held at that temperature for 3 hours. The reaction mixture was cooled and diluted with 200 g water and 60.9 g of 50% sodium hydroxide. The resulting slurry was for filtered and the solids were dried under vacuum for 2 hours. Approximately 34.3 g of solid product was obtained.

Step 2: A 250 ml reactor equipped with, heating mantle, temperature controller, condenser and stirrer was charged 9.98 g of N-(3-dimethylaminopropyl)-4-chloro-1,8-naphthalimide (from Step 1 above), 13.6 g of 25% sodium methoxide and 40.6 g of methanol. The mixture was heated to 67° C. for 5 hours. The reaction was orange in color and cloudy. The reaction product was cooled down to room temperature and 3.1 g of concentrated HCl in 135.5 g of water was added. The reaction was now an orange/red colored clear liquid.

Step 3: The reaction product was stirred and 3.7 g of allyl glycidyl ether was added. The reaction product was heated to 60° C. and held at that temperature for 3 hours. 0.1 g or 4-methoxyphenol (polymerization inhibitor) was then added.

The reaction product above was analyzed LC: the desired product 4-methoxy-N-(3-dimethylaminopropyl)-1,8-naphthalimide, 2-hydroxy-3-allyloxy propyl, quaternary salt was 61.5 area percent. The starting amine 4-methoxy-N-(3-dimethylaminopropyl)-1,8-naphthalimide was (corresponding to Structure (III)) (16.9% by area).

The ratio of the desired product to the undesired starting material is approximately 3:1. The inventors on U.S. Pat. No. 6,645,428 did not realize the negative impact of the materials of Structure (III), but they would not have exemplified an example where almost 25% of the product is undesired material. It would not be obvious to minimize the materials of Structure (III) because it is a surprise that the absorption and emission wavelengths of N-(3-dimethylaminopropyl)-1,8-naphthalimide is the same as the desired product. More surprisingly the signal of N-(3-dimethylaminopropyl)-1,8-naphthalimide is stronger than that of the monomer 3a. Since, N-(3-dimethylaminopropyl)-4-methoxy-1,8-naphthalimide cannot be polymerized, using the monomer of Example 3a in polymers creates a 20-40% error in the signal at the starting point in the process (see fluorescent Table 6 in Polymer Example 22. As the water is reused and cycles of concentration increase, the error increases from 20% to 100% and more. In practical use the polymer needs to be detected to within a 10% error. Thus, the practical utility of the monomer produced according to Example 6 is minimal at best and unusable at worst. Furthermore, the polymers made with this monomer composition will not maintain free chlorine in the application which is absolutely critical for biocidal performance.

Example 6 of U.S. Pat. No. 6,645,428 uses 4 mol % excess allyl glycidyl ether and Monomer Example 3 (detailed above) shows that a nearly 100 mol % access is needed to minimize the starting N-(3-dimethylaminopropyl)-4-methoxy-1,8-naphthalimide. This would not have been obvious to one skilled in the art.

MONOMER EXAMPLE 3B (COMPARATIVE)

We repeated Example 6 of U.S. Pat. No. 6,645,428 and this time utilized stripping:

Step 1: A 500 ml reactor equipped with heating mantle, temperature controller, condenser and stirrer was charged with 21 ml of glacial acetic acid, 10.5 g of 3-dimethylaminopropyl amine and 23.3 g of 4-chloro-1,8-naphthalic anhydride. The reaction was heated to 122° C. and held at that temperature for 3 hours. The reaction mixture was cooled and diluted with 200 g water and 60.9 g of 50% sodium hydroxide. The resulting slurry was for filtered and the solids were dried under vacuum for 2 hours.

Step 2: A 250 ml reactor equipped with, heating mantle, temperature controller, condenser and stirrer was charged 9.98 g of N-(3-dimethylaminopropyl)-4-chloro-1,8-naphthalimide (from Step 1 above), 13.6 g of 25% sodium methoxide and 40.6 g of methanol. The mixture was heated to 67° C. for 5 hours. While the reaction was cooling down to room temperature the excess sodium methoxide was neutralized with 12 M hydrochloric acid to pH 10.5. U.S. Pat. No. 6,645,428 is silent as to the extent of stripping. We initially attempted to strip the solvent completely but the residue was sticky and could not be removed from the stripping flask used in the rotary evaporator. Therefore, we concluded that the inventors on U.S. Pat. No. 6,645,428 did not strip the solvent to this extent. Accordingly, we then attempted to strip the solvent to the point just before the residue became too sticky to remove it from the stripping flask. In this second attempt, a thick molasses like orange residue was obtained, consistent with the description in U.S. Pat. No. 6,645,428, but the residue could still be removed from the flask. The solids of this thick molasses like orange residue was measured and found to be 70% with the rest being methanol. We calculated that if Step 2 went to completion, these solids contained 29.5 grams of N-(3-dimethylaminopropyl)-4-methoxy-1,8-naphthalimide and 11.6 grams of sodium chloride. Therefore, the N-(3-dimethylaminopropyl)-4-methoxy-1,8-naphthalimide was 71.8% of the solid content or 50 weight % of the thick molasses like orange residue.

Step 3: A 100 ml round bottom flask was charged with 6.0 g of thick molasses like orange residue from Step 2 above which is 3.0 g N-(3-dimethylaminopropyl)-4-methoxy-1,8-naphthalimide (9.6 mmol), 37 g of deionized water and 1.15 g of allyl glycidyl ether (10 mmol) was added. The reaction product was heated to 60° C. and held at that temperature for 2.5 hours and then cooled to room temperature.

Figure 9:
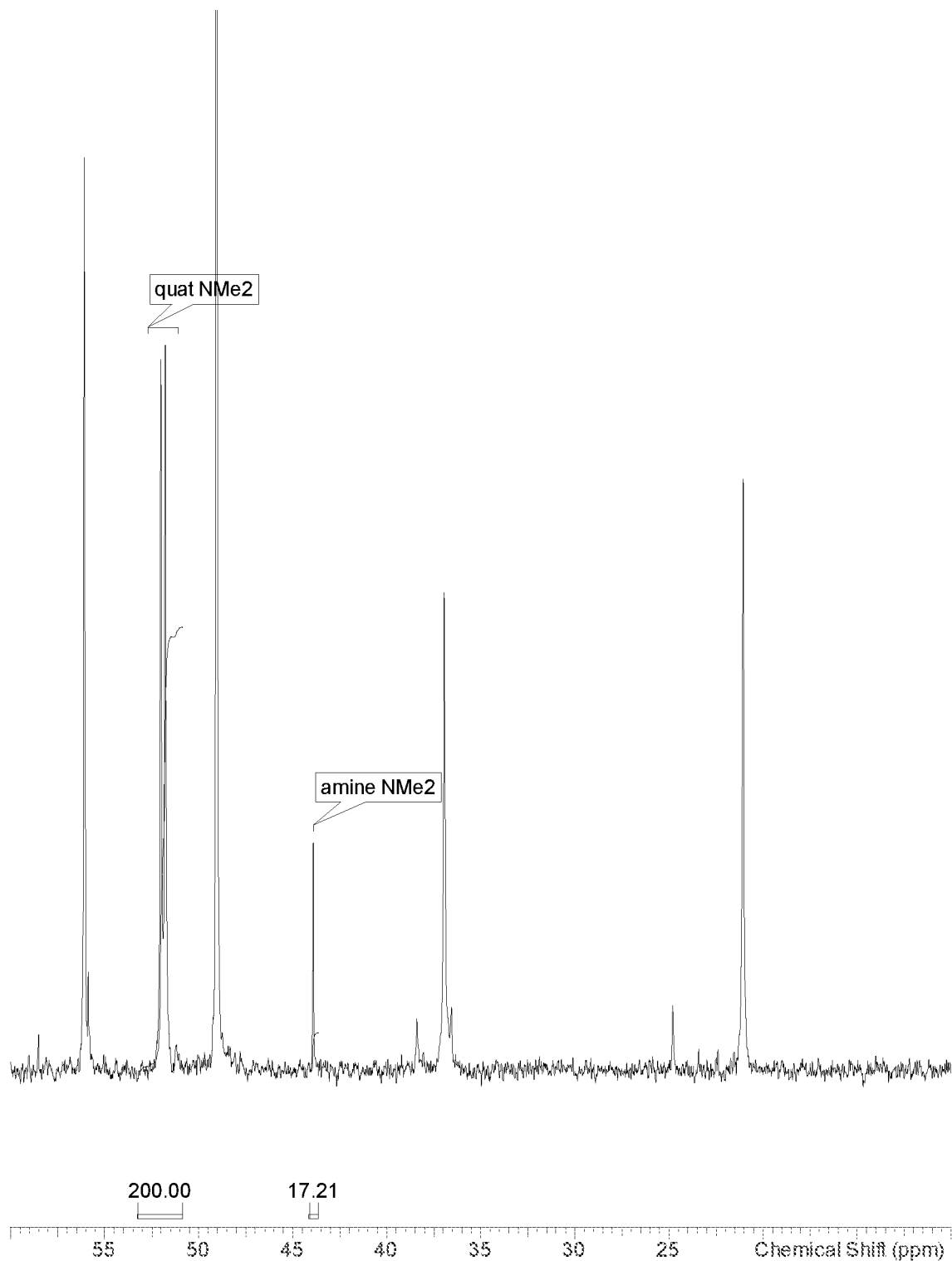
FIG. 9. depicts a portion of the $^{13}$C NMR spectrum of Monomer Example 3b.

The mol % of N-(3-dimethylaminopropyl)-4-methoxy-1,8-naphthalimide, based on the total mol % of polymerizable quaternary moieties of Structure (I) as measured by $^{13}C$ NMR procedure detailed in Monomer Example 3 was 8.6 mol % (see FIG. 9).

The ratio of the desired product to the undesired starting material is extremely high. The inventors did not realize the negative impact of the materials of Structure (III), or they would not have exemplified an example where almost 10% of the product is undesired material. It would not have been obvious to minimize the materials of Structure (III) because it is a surprise that the absorption and emission wavelengths of N-(3-dimethylaminopropyl)-1,8-naphthalimide is the same as the desired product. More surprisingly the signal of N-(3-dimethylaminopropyl)-1,8-naphthalimide is stronger than that of the monomer 3b. Since, N-(3-dimethylaminopropyl)-4-methoxy-1,8-naphthalimide cannot be polymerized, using the monomer of Example 3b in polymers creates a 10% error in the signal at the starting point in the process. As the water is reused and cycles of concentration increase, the error increases from 10% to 50% and more. In practical use the polymer needs to be detected to within a 10% error, preferably less than a 5% error, more preferably less than a 1.5% error and most preferably not present at all at the starting point in the process, since the error is multiplied with each cycle of concentration. Since water is getting scarce it is common to have 3-7 cycles of concentration and even higher in certain areas. Thus, the practical utility of the monomer produced according to Example 6 of U.S. Pat. No. 6,645,428 is minimal at best and unusable at worst. Furthermore, the polymers made with this monomer composition will not maintain free chlorine in the application which is absolutely critical for biocidal performance.

Example 6 of U.S. Pat. No. 6,645,428 uses 4 mol % excess allyl glycidyl ether and the Monomer Example 3 (detailed above) shows that a nearly 100 mol % excess or more is needed to minimize the starting N-(3-dimethylaminopropyl)-4-methoxy-1,8-naphthalimide. This would not have been obvious to one skilled in the art. While this is the preferred way to minimize the starting N-(3-dimethylaminopropyl)-4-methoxy-1,8-naphthalimide according to the present disclosure, persons skilled in the art will realize there are other ways to do so.

MONOMER EXAMPLE 4

4-methoxy-N-(3-dimethylaminopropyl)-1,8-naphthalimide, 1 or 2-hydroxy-3-allyloxy propyl, quaternary salt. In Structure (I): $R_4$ and $R_{41}$ are independently selected from H, methoxy, or are both methoxy, $R_1$ and $R_2$ are both $CH_3$ ($C_1$ alkyl), $R_3$ is 2-hydroxy-3-(meth)allyloxypropyl or 1-hydroxy-3-(meth)allyloxypropyl, A is propyl ($C_3$ alkyl), B is nitrogen and X is hydroxide and sulfate. The monomer has a minimal residual N-(3-dimethylaminopropyl)-4-methoxy-1,8-naphthalimide (corresponding to Structure (III)) using a 100% excess allyl glycidyl ether. In Structure (III): $R_4$ and $R_{41}$ are independently selected from H, methoxy, or are both methoxy, $R_1$ and $R_2$ are both $CH_3$ ($C_1$ alkyl), A is propyl ($C_3$ alkyl) and B is nitrogen.

Step 4: Synthesis of N-(3-dimethylaminopropyl)-4-bromo-1,8-naphthalimide

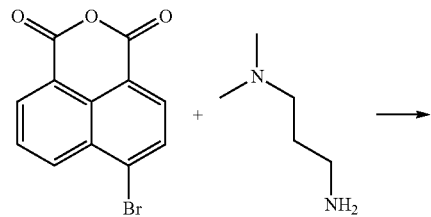

Chemical Formula:
$C_{12}H_5BrO_3$
Molecular Weight:
277.07

Chemical Formula:
$C_5H_{14}N_2$
Molecular Weight:
102.18

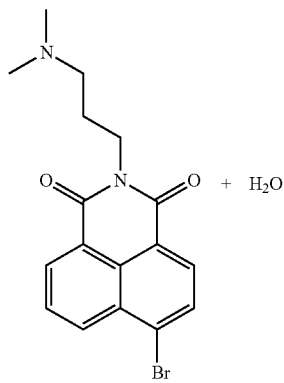

Chemical Formula:
$C_{17}H_{17}BrN_2O_2$
Molecular Weight:
361.24

4-Bromo-1,8-naphthalic anhydride (TCI, Lot #: RQYXL, 36.07 grams, 0.1302 mol) and toluene (Acros Lot #: 1878076, 300 grams) were placed in a flask equipped with a nitrogen inlet/outlet, Dean-Stark distillation head, condenser, thermocouple, and syringe pump inlet. The solution was heated to 55° C.

TCI catalog says the material is greater than 95% purity and this particular batch had a certificate of analysis that said, 98% purity.

4-Bromo-1,8-napthalic anhydride was purchased from TCI was analyzed before the synthesis. It appeared 99.3 area % purity based on in-house GC/MS analysis Table 1. The other impurities and the area % of these impurities are listed in the table below.

TABLE 1

| GC/MS analysis of by 4-bromo-1,8-naphthalic anhydride | |
|---|---|
| Component | area % as measured by GC/MS |
| 1,8-naphthalic anhydride | 0.27% |
| Tribromo naphthalene | 0.22% |
| Bromo-1,8-naphthalic anhydride | 99.3% |
| Dibromo-1,8-naphthalic anhydride | 0.08% |

GC Conditions:

| Column | Agilent DB-5 30M × 0.32 mm 0.5 um |
|---|---|
| Oven Program | 105° C. hold 2 minutes, 10° C./minute to 320° C. hold 5 minutes |
| Injector | 285° C. |
| Carrier Gas | Helium 40 cm/second |
| Split Flow | 60 ml/min |
| Injection | 1 ul |
| Sample | 12.4 mg/ml in Tetrahydrofuran |
| Detection | Total Ion Current, Agilent 5975C GC/MS |

3-(3-dimethylamino)-1-propylamine (DMAPA) (Acros Lot #: A0371713, 14.11 grams, 0.4463 mol) was placed in an Air-Tite plastic 30 mL syringe. The syringe was then set up on a Fisher single syringe pump. Feed rate was set to complete the addition of DMAPA in an hour. The addition was started at 55° C. The mixture was white slurry initially and this slurry became a yellow solution when the addition of DMAPA was complete at 70° C.

After the completion of the DMAPA addition, the reaction temperature was raised stepwise to 60, 65, 75, 80, 95, and 110° C. in 2 hours. The reaction mixture was heated 110° C. for two and a half hours. Water, 1.6 grams was distilled out.

After the heating, the product was isolated by solvent strip and vacuum drying. The final product weighed 48.0 grams (quantitative yield). $^1$H-NMR spectrum of the sample conformed the target structure and the product appeared high purity.

Step 2: Synthesis of N-(3-dimethylamino-propyl)-4-methoxy-1,8-naphthalimide

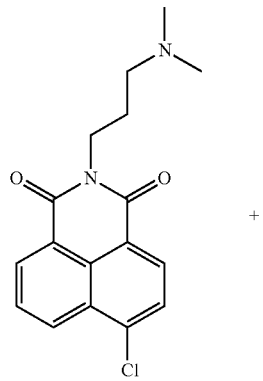

Chemical Formula: $C_{17}H_{17}BrN_2O_2$
Molecular Weight: 361.24

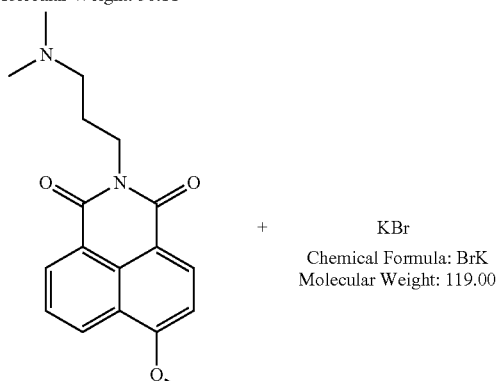

Methanol (400 mL) and potassium hydroxide (Mallinckrodt, Lot #: 6984KLHM, 14.28 g, 0.2545 mol) were placed in a flask equipped with a nitrogen inlet/outlet, magnetic stirrer, thermocouple and heating mantle. The mixture was heated to 60° C., the mixture became a homogeneous solution. To the solution was added N-(3-dimethylpropyl)-4-bromo-1,8-naphthalimide (from step 1, 47.53 grams, 0.0954 mol) in a small portion to avoid too much exotherm. The temperature of the reaction mixture rose to 64° C. during this addition. The mixture was a homogeneous solution.

The reaction mixture was stirred and heated to 65° C. for 5 hours. TLC (silica gel, 25 wt % triethylamine in ethyl acetate) was used to monitor the reaction progress. The starting material was not consumed (did not disappear completely on TLC plate). An aliquot was analyzed by $^1$H-NMR, and it was calculated about 6 mol % of the starting material remained. The solvent was evaporated to afford thick slurry. Ethyl acetate about 400 mL was added to this slurry and the resulting mixture was vacuum filtered to remove insoluble salts, and the salts was washed with 50 mL of ethyl acetate. The combined filtrate was concentrated by rotary evaporation to the half of the original volume, then insolubles (not the product) appeared. This insolubles are presumably salts, the water wash was performed to remove the insolubles.

Recrystallization of the final product was done with 200 mL of n-heptane and 250 mL of ethyl acetate in a refrigerator. 27.65 grams (0.08852 mol, 67.3% recovery yield) of the pure product was isolated after filtration and vacuum treatment, the purity of this product was 98.6% by LC-UV.

Purity of the Free Amine Precursor, N-(3-dimethylamino-propyl)-4-methoxy-1,8-naphthalimide After step 2, N-(3-dimethylamino-propyl)-4-methoxy-1,8-naphthalimide was analyzed by LC for its purity (RA-SUS20011001), Table 2. The result of the analysis and the corresponding molecular structures (based only on found formulae) are shown in Table 2.

TABLE 2

LC analysis of N-(3-dimethylamino-propyl)-4-methoxy-1,8-naphthalimide (KS2921-16-2, 300 nm)

| Component | Area % |
|---|---|
| N-(3-dimethylamino-propyl)-4,5-dimethoxy-1,8-naphthalimide | 0.05% |
| N-(3-dimethylamino-propyl)-1,8-naphthalimide | 0.15% |
| N-(3-dimethylamino-propyl)-4-methoxy-1,8-naphthalimide | 98.59% |
| N-(3-dimethylamino-propyl)-4-bromo-1,8-naphthalimide | 1.04% |
| N-(3-dimethylamino-propyl)-4-methoxy,5-bromo-1,8-naphthalimide | 0.17% |

Step 3: Preparation of a Solution of the Quaternary Ammonium Monomer from N-(3-dimethylamino-propyl)-4-methoxy-1,8-naphthalimide and Allyl Glycidyl Ether

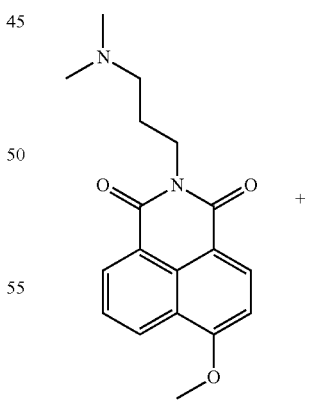

Chemical Formula: $C_{18}H_{20}N_2O_3$
Molecular Weight: 312.37

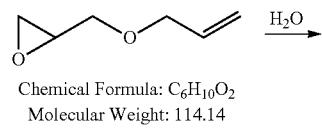

Chemical Formula: $C_6H_{10}O_2$
Molecular Weight: 114.14

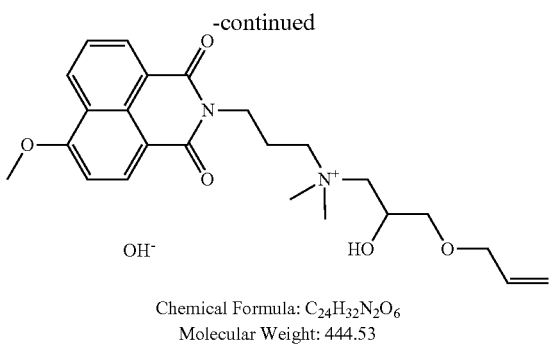

Chemical Formula: C$_{24}$H$_{32}$N$_2$O$_6$
Molecular Weight: 444.53

N-(3-dimethylaminopropyl)-4-methoxy-1,8-naphthalimide (from step 2, 10.41 grams, 0.033 mol) and DI water (97.73 grams) were placed in a flask equipped with a thermocouple, heating mantle, nitrogen inlet/outlet, and magnetic stir bar. The mixture was then heated to 60° C., the mixture became a yellow suspension. Allyl glycidyl ether (AGE, Acros A0384473, 7.28 grams, 0.0638 mol) was placed in a syringe. AGE was slowly added to the flask over 50 minutes, the reaction mixture turned red and became homogeneous. The heating was stopped in 2 hours after the completion of AGE addition. The resultant solution was analyzed for free amine content and it was 0.008 wt % by LC. It is important to analyze the reaction by LC or any other convenient means, towards the end of the reaction to make sure that the free amine content is low. If it is not, keep adding AGE till the free amine content is below a desired level. The molar amount of amine based on the total moles of monomer is them determined by $^{13}$C NMR.

The mol % of N-(3-dimethylaminopropyl)-4-methoxy-1,8-naphthalimide, based on the total mol % of quaternary monomer was below the limit of detection by $^{13}$C NMR which is 1.2 mol %. Therefore, the mol % of N-(3-dimethylaminopropyl)-4-methoxy-1,8-naphthalimide, based on the total mol % of quaternary monomer was less than 1.2 mol %.

The pH of this solution was 12. 100 g of the final reaction product solution was taken and the pH was suggested to 7 using 0.1N sulfuric acid to give a 4-methoxy-N-(3-dimethylaminopropyl)-1,8-naphthalimide, 1 or 2-hydroxy-3-allyloxy propyl, quaternary ammonium hydroxide/sulfate salt. 100 g of the final reaction product solution was taken and the pH was suggested to 3 using acrylic acid to give a 4-methoxy-N-(3-dimethylaminopropyl)-1,8-naphthalimide, 1 or 2-hydroxy-3-allyloxy propyl, quaternary ammonium acrylate salt.

MONOMER EXAMPLE 5

4-(tri(ethylene glycol) monomethyl ether)-N-(3-dimethylaminopropyl)-1,8-naphthalimide, 1 or 2-hydroxy-3-allyloxy Propyl, Quaternary Salt In Structure (I): R$_4$ and R$_{41}$ are independently selected from H or C$_1$alk-O—(CHR$_5$CH$_2$O—)$_n$, R$_5$ is H, n=1, R$_1$ and R$_2$ are both CH$_3$ (C$_1$ alkyl), R$_3$ is 2-hydroxy-3-(meth)allyloxypropyl or 1-hydroxy-3-(meth)allyloxypropyl, A is propyl (C$_3$ alkyl), B is nitrogen and X is hydroxide Step I: Synthesis of N-(3-dimethylaminopropyl)-4-chloro-1,8-naphthalimide 4-chloro-1,8-naphthalic anhydride (99.36 grams, 0.4271 mol) and toluene (600 grams) were placed in a flask equipped with a nitrogen inlet/outlet, Dean-Stark distillation head, condenser, thermocouple, and syringe pump inlet. The solution was heated to 55° C. 3-dimethylamino-1-propylamine (45.6 grams, 0.4463 mol) was placed in a 50 mL syringe. The syringe was then set up on a syringe pump. Feed rate was set to complete the addition in an hour. The addition was started at 55° C.

After the completion of the addition, the reaction temperature was raised stepwise to 60, 65, 75, 80, 95, and 105° C. in 2 hours. The reaction mixture was heated 105° C. for two and a half hours. Water, 6.0 grams was distilled out.

The product was isolated by vacuum drying. The final product weighed 134.16 grams (99% recovery yield). $^1$H-NMR analysis confirmed the target structure and the product appeared high purity.

Step II: 4-(tri(ethylene glycol) monomethyl ether)-N-(3-dimethylaminopropyl)-1,8-naphthalimide Sodium hydride (2.93 grams, 60 wt % dispersed in mineral oil, 0.0733 mol) was placed in a flask equipped with a nitrogen inlet/outlet, magnetic stirrer, thermocouple and heating mantle. The sodium hydride was washed with dry hexane twice to remove mineral oil. Triethyleneglycol monomethyl ether (TEGME, 76.15 grams, 0.4638 mol) was slowly added to the flask to prevent vigorous hydrogen evolution. During the addition of TEGME, the reaction mixture was under nitrogen and the temperature rose to 47° C. from room temperature. N-(3-dimethylaminopropyl)-4-chloro-1,8-naphthlimide (20.26 grams, 0.0640 mol) was added to the flask as solid. The flask was heated to 60° C. and the reaction mixture was stirred for 2 hours at this temperature. An aliquot was taken out from the reaction mixture and analyzed by TLC technique (eluent; 20% triethylamine in ethyl acetate). The TLC showed no starting material.

Acetic acid (0.58 grams, 0.0097 mol) was added to the reaction mixture, and about a half of the amount of TEGME was evaporated from the mixture at 72° C. under 0.3 Torr. Ethyl acetate was added to precipitate salts and the salts were filtered off. Ethyl acetate was evaporated from the filtrate using a rotary evaporator. Acetic acid about 20 mL was added to the resultant oily material to form a salt of the target amine, and 400 mL of diethyl ether was added to the salt. The salt (viscous oil) was separated from the diethyl ether layer by decantation. Another 200 mL of diethyl ether was added to the oil and decanted the diethyl ether again. Triethylamine about 30 mL was added to the oil and evaporated excess triethylamine, 27.7 grams of viscous oil was obtained. This oil was not very pure.

2 grams of this oil was purified by silica gel (60 grams) column chromatography using 10 wt % triethylamine solution in ethyl acetate. The resultant oil was purer but still contained 25 mol % of TEGME by $^1$H-NMR analysis.

The oil was dissolved in more than 600 mL of ethyl acetate and the solution was washed with water few times. After drying the organic layer, the solvent was stripped, and vacuum treated to obtain the final product of 14 grams (0.0315 mol, 50% yield, 79 area % purity by LC analysis)

HPLC conditions are listed:

| | |
|---|---|
| Column | Agilent Porashell C8 4 mm × 50 mm |
| Mobile Phase | A 50 mm AF ph 3.0, D Acetonitrile |
| | Time 0 90% A/10% D |
| | Time 10 50% A/50% D |
| | Time 10.1 90% A/10% D |

Step III: 4-(tri(ethylene glycol) monomethyl ether)-N-(3-dimethylaminopropyl)-1,8-naphthalimide, 1 or 2-hydroxy-3-allyloxy Propyl, Quaternary Salt 4-(tri(ethylene glycol) monomethyl ether)-N-(3-dimethylaminopropyl)-1,8-naphthalimide (16.37 grams, 0.03683 mol) and DI water (151.5 grams) were placed in a flask equipped with a thermocouple, heating mantle, nitrogen inlet/outlet, and magnetic stir bar. The mixture was then heated to 55° C., the mixture became a homogeneous yellow solution. Allyl glycidyl ether (AGE) (4.5 grams, 0.03943 mol) was placed in a syringe. AGE was slowly added to the flask over 30 minutes, the reaction mixture turned red. The heating was stopped in 20 minutes after the completion of AGE addition. An aliquot was taken for $^1$H-NMR. The aliquot was dried under vacuum and was run $^1$H-NMR in CDCl$_3$. The $^1$H-NMR spectrum from the CDCl$_3$ solution indicated that the ratio of the starting material and the target material was about 2 to 1.

Additional 3.0 grams of AGE was added to the reaction mixture, and the mixture was stirred for additional 4 hours at 55° C. $^1$H-NMR analysis was performed; there was no starting material. LC-MS/UV analysis of the same sample indicated the formation of the target quaternary with 62 area % (by UV) and trace amount of the starting amine.

Solid content was 12.83 wt % analyzed by a moisture analyzer at 180° C. The theoretical content is 12 wt %.

HPLC Condition 5 ul of sample was diluted with 1.0 ml of water. Sample was analyzed by LC/UV 300 nm/ELSD/MS with listed conditions.

| | |
|---|---|
| Column | Agilent Porashell C8 4 mm × 50 mm |
| Mobile Phase | A 50 mm AF ph 3.0, D Acetonitrile |
| | Time 0 90% A/10% D |
| | Time 10 50% A/50% D |
| | Time 10.1 90% A/10% D |
| | Stop Time 14 minutes |
| Injection | 1.0 ul |
| Flow Rate | 1 ml/min |
| Positive Ion | |

POLYMER EXAMPLES

Polymer Example 1

An initial charge of 190.1 g of deionized water was added to a 1-liter glass reactor with inlet ports for an agitator, water cooled condenser, thermocouple, and adapters for the addition of monomer and initiator solutions. The reactor contents were heated to 95° C. A mixed monomer solution which consisted of 298.4 g of acrylic acid (4.14 moles, 94.4 mol % of polymer), 4.18 g of N-(3-dimethylaminopropyl)-4-methoxy-1,8-naphthalimide, methallyl chloride quaternary salt (monomer of Monomer Example 1) (formula weight 403, 0.01038 moles, 0.24 mol % of polymer) was mixed and then fed to the reactor via measured slow-addition with stirring over a period of 4 hours. A second solution of 24.1 g of sodium hypophosphite monohydrate (0.23 moles, 5.25 mol % of polymer) dissolved in 72 g of deionized water was mixed and then fed to the reactor via measured slow-addition with stirring over a period of 4 hours. An initiator solution of 6.7 grams of sodium persulfate dissolved in 68.4 grams water was concurrently added, starting at the same time as the monomer solution, for a period of 4 hours and 15 minutes. The reaction product was then held at 95° C. for 60 minutes. The polymer solution was cooled and then neutralized with 40 g of 50% sodium hydroxide. The final polymer solution had a solids content of about 47.2 and a pH of 3.6.

Polymer Example 2

An initial charge of 86.9 g of maleic anhydride (0.89 moles, 24.95 mol % of polymer) mixed with 130.9 g of deionized water was added to a 1-liter glass reactor with inlet ports for an agitator, water cooled condenser, thermocouple, and adapters for the addition of monomer and initiator solutions. The mixture was heated to 65° C. The maleic anhydride was neutralized using 35.5 g of 50% sodium hydroxide while keeping the temperature above 65° C. 129.9 g of isopropyl alcohol was then added to the reactor. Next, 0.0810 g of ferrous ammonium sulfate hexahydrate was added to the reactor. The reactor contents were heated to 84° C. A mixed monomer solution which consisted of 164.6 g of acrylic acid (2.29 moles, 64.3 mol % of polymer), 16 g of methyl methacrylate (0.16 moles, 4.5 mol % of polymer), 97.3 g of 2-acrylamido-2-methyl propane sulfonic acid sodium salt, 50% solution (0.21 moles, 6 mol % of polymer), 3.59 g of N-(3-dimethylaminopropyl)-4-methoxy-1,8-naphthalimide, methallyl chloride quaternary salt (monomer of Monomer Example 1) (formula weight 403, 0.0089 moles, 0.25 mol % of polymer) dissolved in 17 g of 2-propanol, was mixed and then fed to the reactor via measured slow-addition with stirring over a period of 4 hours. An initiator solution of 10 grams of sodium persulfate and 33.8 g of 35% hydrogen peroxide was dissolved in 32.7 grams water was concurrently added, starting at the same time as the monomer solution, for a period of 4 hours. The reaction product was then held at 85° C. for 60 minutes. The Reactor was then set up for distillation. An azeotropic of 244.6 g of a mixture of water and isopropyl alcohol, was then distilled. 188.6 g of deionized water was dripping during the distillation. The final polymer solution had a solids content of 48.3% and a pH of 3.2.

Polymer Example 3

An initial charge of 229.4 g of maleic anhydride mixed with 157.1 g of deionized water and 0.0575 g of ferrous ammonium sulfate hexahydrate was added to a 1-liter glass reactor with inlet ports for an agitator, water cooled condenser, thermocouple, and adapters for the addition of monomer and initiator solutions. The mixture was heated to 85° C. 0.59 g of N-(3-dimethylaminopropyl)-4-methoxy-1,8-naphthalimide, methallyl chloride quaternary salt) (monomer of Monomer Example 1) (formula weight 403, was added to the reactor in one shot. An initiator solution of 26 g of 35% hydrogen peroxide was added over the first hour. The reaction product was then heated to 95° C. An initiator solution of 153.15 g of 35% hydrogen peroxide was added over the next 4.5 hours. 0.59 g of N-(3-dimethylaminopropyl)-4-methoxy-1,8-naphthalimide, methallyl chloride quaternary salt dissolved in 2.8 g of 2-propanol, was added to the reactor in one shot at the 1 hour, 2 hour and 3 hour mark.

After the hydrogen peroxide feed was completed, the reaction was held at 95° C. for 45 minutes. The N-(3-dimethylaminopropyl)-4-methoxy-1,8-naphthalimide, methallyl chloride quaternary salt was 0.25 mol % of the total polymer with the rest being maleic acid. The final polymer solution had a solids content of 48.3% and a pH of 3.2. The residual maleic acid was found to be 9300 ppm. 229.4 g of maleic anhydride becomes 271.5 g of maleic acid when reacted with water. Therefore, the amount of total maleic acid in solution is 47.8 weight percent. Therefore, the maleic acid conversion is 98%. Since maleic acid is very unreactive, a maleic acid conversion of greater than 95% is considered to be acceptable.

Polymer Example 4

An initial charge of 113.4 g of maleic anhydride (1.16 moles, 49.9 mol % of polymer) mixed with 241.3 g of deionized water was added to a 1-liter glass reactor with inlet ports for an agitator, water cooled condenser, thermocouple, and adapters for the addition of monomer and initiator solutions. The maleic anhydride was neutralized using 92.4 g of 50% sodium hydroxide. Next, 0.0528 g of ferrous ammonium sulfate hexahydrate was added to the reactor. The reactor contents were heated to 95° C. A mixed monomer solution which consisted of 83.2 g of acrylic acid (1.155 moles, 49.8 mol % of polymer), 2.33 g of N-(3-dimethylaminopropyl)-4-methoxy-1,8-naphthalimide, methallyl chloride quaternary salt (monomer of Monomer Example 1) (formula weight 403, 0.0058 moles, 0.25 mol % of polymer) dissolved in 11 g of 2-propanol, was mixed and then fed to the reactor via measured slow-addition with stirring over a period of 4 hours. An initiator solution of 7.5 grams of sodium persulfate and 106 g of 35% hydrogen peroxide was dissolved in 30 grams water was concurrently added, starting at the same time as the monomer solution, for a period of 4 hours. The reaction product was then held at 95° C. for 60 minutes. The final polymer solution had a solids content of 34.4% and a pH of 4.3. The residual maleic was found to be 23 ppm and the conversion was greater than 99.9%, which is excellent.

Polymer Example 5

An initial charge of 130.5 g of deionized water was added to a 1-liter glass reactor with inlet ports for an agitator, water cooled condenser, thermocouple, and adapters for the addition of monomer and initiator solutions. The reactor contents were heated to 60° C. and sparged with nitrogen. A mixed monomer solution which consisted of 88.12 g of acrylic acid (1.22 moles, 49.7 mol % of polymer), 175.2 g of 50% acrylamide solution (1.23 moles, 50.24 mol % of polymer), N-(3-dimethylaminopropyl)-4-methoxy-1,8-naphthalimide, methallyl chloride quaternary salt (monomer of Monomer Example 1) (formula weight 399, 0.00258 moles, 0.105 mol % of polymer) dissolved in 4.95 g of 2-propanol, was mixed and then fed to the reactor via measured slow-addition with stirring over a period of 2 hours. An initiator solution of 2.56 grams of ammonium persulfate dissolved in 30 grams water was concurrently added, starting at the same time as the monomer solution, for a period of 2 hours. A solution of 20.7 g of 41% sodium bisulfite dissolved in 15 g of water was concurrently added, starting as the same time as the monomer solution, for a period of 2 hours. The reaction product was then held at 60° C. for 60 minutes. The polymer solution was cooled and then neutralized with 31 g of 50% sodium hydroxide. The final polymer solution had a solids content of about 41% and a pH of 4.5.

Example 6

Fluorescent Signals

The polymer samples from Polymer Examples 1-4 each were diluted in water to 10 ppm and the pH was adjusted to 9, and the fluorescent signal was determined by excitation of the sample at the excitation wavelengths and measurement at the emission wavelengths as stated in Table 1 using a Shimadzu RF-6000 model spectro fluorimeter.

TABLE 1

Fluorescence intensity of various polymers

| Polymer | Polymer description | Excitation wavelength λ (nm) | Emission wavelength λ (nm) | Fluorescence intensity |
|---|---|---|---|---|
| Example 1 | Acrylic acid/phosphino/fluorescent monomer 94.4/5.25/0.24 | 377 | 458 | 11476 |
| Example 2 | Acrylic acid/maleic acid/AMPS/methylmethacrylate/fluorescent monomer 64.3/24.95/5.98/4.5/0.25 | 376 | 459 | 10568 |
| Example 3 | Polymaleic acid with 0.25% fluorescent monomer | 377 | 462 | 4890 |
| Example 4 | Acrylic acid/maleic acid/fluorescent monomer 49.84/49.9/0.25 | 377 | 460 | 6066 |

Fluorescent monomer in Table 1 is N-(3-dimethylaminopropyl)-4-methoxy-1,8-naphthalilmide, methallyl chloride quaternary salt.

The data in Table 1 indicate the polymers of this disclosure have good fluorescent signals.

Example 7

Carbonate Inhibition

Various polymers were evaluated for their ability to prevent the precipitation of calcium carbonate in typical cooling water conditions, a property commonly referred to as the threshold inhibition. Solutions were prepared in which the weight ratio of calcium concentration to alkalinity was 1.000:1.448 to simulate typical conditions in industrial water systems used for cooling. Generally, water wherein the alkalinity is proportionately less will be able to reach higher levels of calcium, and water containing a proportionally greater amount of alkalinity will reach lower levels of calcium. Since cycle of concentration is a general term, one cycle was chosen, in this case, to be that level at which calcium concentrations equaled 100.0 mg/L Ca as $CaCO_3$ (40.0 mg/L as Ca). The complete water conditions at one cycle of concentration (i.e., make-up water conditions) were as follows:

Simulated Make-Up Water Conditions:
  100.00 mg/L Ca as $CaCO_3$ (40.0 mg/L as Ca) (one cycle of concentration)
  49.20 mg/L Mg as $CaCO_3$ (12.0 mg/L as Mg)
  2.88 mg/L Li as $CaCO_3$ (0.4 mg/L as Li)
  144.80 M Alkalinity (144.0 mg/L as $HCO_3$)
  13.40 P Alkalinity (16.0 mg/L as $CO_3$)

Materials:
  One incubator/shaker, containing a 125 mL flask platform
  Screw-cap Erlenmeyer Flasks (125 mL)
  Deionized Water
  Analytical balance
  Electronic pipette(s) capable of dispensing between 0.0 mL and 2.5 mL
  250 Cycle Hardness Solution*
  10,000 mg/L treatment solutions, prepared using known active solids of the desired treatment*
  10% and 50% solutions of NaOH
  250 Cycle Alkalinity Solution*
  0.2 µm syringe filters or 0.2 µm filter membranes
  Volumetric Flasks (100 mL)
  Concentrated Nitric Acid
  * See solution preparations in next section.

Solution Preparations:
All chemicals used were reagent grade and weighed on an analytical balance to ±0.0005 g of the indicated value. All solutions were made within thirty days of testing. The hardness and alkalinity solutions were prepared in a one liter volumetric flask using DI water. The following amounts of chemical were used to prepare these solutions—

250 Cycle Hardness Solution:
  10,000 mg/L Ca ⇒ 36.6838 g $CaCl_2 \cdot 2H_2O$
  3,000 mg/L Mg ⇒ 25.0836 g $MgCl_2 \cdot 6H_2O$
  100 mg/L Li ⇒ 0.6127 g LiCl 250 Cycle Alkalinity Solution:
  36,000 mg/L $HCO_3$ ⇒ 48.9863 g $NaHCO_3$
  4,000 mg/L $CO_3$ ⇒ 7.0659 g $Na_2CO_3$ 10,000 mg/L Treatment Solutions:
Using percentage of active product in the supplied treatment, 250 mL of a 10,000 mg/L active treatment solution was made up for every treatment tested. The pH of the solutions was adjusted to between 8.70 and 8.90 using 50% and 10% NaOH solutions by adding the weighed polymer into a specimen cup or beaker and filling with DI water to approximately 90 mL. The pH of this solution was then adjusted to approximately 8.70 by first adding the 50% NaOH solution until the pH reached 8.00, and then by using the 10% NaOH until the pH equaled 8.70. The solution was then poured into a 250 mL volumetric flask. The specimen cup or beaker was rinsed with DI water and this water was added to the flask until the final 250 mL was reached. The amount of treatment product to be weighed was calculated as follows:

$$\text{Grams of treatment needed} = \frac{(10{,}000 \text{ mg/L})(0.25 \text{ L})}{(\text{decimal \% of active treatment})(1000 \text{ mg})}$$

Test Setup Procedure:
The incubator shaker was turned on and set for a temperature of 50° C. to preheat. Screw cap flasks were set out in groups of three to allow for triplicate testing of each treatment, allowing for testing of different treatments. The one remaining flask was used as an untreated blank. 96.6 grams of DI water was weighed into each flask.

Using a 2.5 mL electric pipette, 1.20 mL of hardness solution was added to each flask to simulate four cycles of make-up water.

Using a 250 µL electronic pipette, 200 µL of desired treatment solution was added to each flask to achieve a 20 ppm active treatment dosage. A new tip on the electric pipette was used for each treatment solution so cross contamination did not occur.

Using a 2.5 mL electric pipette, 1.20 mL of alkalinity solution was added to each flask to simulate four cycles of make-up water having an LSI value of 2.79. The addition of alkalinity was done while swirling the flask, so as not to generate premature scale formation from high alkalinity concentration pooling at the addition site.

One "blank" solution was prepared in the exact same manner as the above treated solutions, except DI water was added in place of the treatment solution.

All flasks uncapped were placed onto the shaker platform and the door closed. The shaker was run at 250 rpm and 50° C. for 17 hours.

A "total" solution was prepared in the exact same manner as the above treated solutions were prepared, except that DI water was used in place of both the treatment solution and alkalinity solution. This solution was capped and left overnight outside the shaker.

Test Analysis Procedure:
Once 17 hours had passed, the flasks were removed from the shaker and allowed to cool for one hour. Each flask solution was filtered through a 0.2 µm filter membrane. 250 µl of nitric acid was added to 10 ml of each filtrate, and each filtrate was analyzed directly for lithium, calcium, and magnesium concentrations by an Inductively Coupled Plasma (ICP) Optical Emission System. The "total" solution was analyzed in the same manner.

Calculations of Results:
Once the lithium, calcium, and magnesium concentrations were known in all shaker samples and in the "total" solution, the percent inhibition was calculated for each treatment. The lithium was used as a tracer of evaporation in each flask (typically about ten percent of the original volume). The lithium concentration found in the "total" solution was assumed to be the starting concentration in all flasks. The concentrations of lithium in the shaker samples were each divided by the lithium concentration found in the "total" sample. These results provided the multiplying factor for increases in concentration, due to evaporation. The calcium and magnesium concentrations found in the "total" solution were also assumed to be the starting concentrations in all flasks. By multiplying these concentrations by each calculated evaporation factor for each shaker sample, the final intended calcium and magnesium concentration for each shaker sample was determined. By subtracting the calcium and magnesium concentrations of the "blank" from both the actual and intended concentrations of calcium and magnesium, then dividing the resulting actual concentration by the resulting intended concentration and multiplying by 100, the percent inhibition for each treated sample was calculated. The triplicate treatments were averaged to provide more accurate results.

TABLE 2

Percent carbonate inhibition per dosage level of polymer

| Polymer | Polymer description | Dosage 3 ppm | Dosage 5 ppm | Dosage 10 ppm | Dosage 20 ppm | Dosage 50 ppm | Dosage 100 ppm |
|---|---|---|---|---|---|---|---|
| Example 1 | AA/phosphino/FM 94.4/5.25/0.24 | 95 | 95 | 94 | 93 | | |
| Example 2 | AA/MA/AMPS/MMA/FM 64.3/24.95/5.98/4.5/.25 | | 93 | | | | |
| Example 3 | MA/FM 99.75/.25 | | | 92 | 93 | | |
| Example 4 | AA/MA/FM 49.84/49.9/0.25 | | | | 90 | | |

AA = acrylic acid;
FM = the fluorescent monomer N-(3-dimethylaminopropyl)-4-methoxy-1,8-naphthalilmide, methallyl chloride quaternary salt;
MA = maleic acid;
AMPS = 2-acrylamido-2-methyl propane sulfonic acid sodium salt;
MMA = methyl methacrylate;

In the test above, anything above 80% inhibition is considered acceptable. These data in Table 2 indicate that the carbonate inhibition performance using the method disclosed herein with Polymer Examples 1-4 are excellent.

Polymer Example 8

An initial charge of 108.6 g of deionized water was added to a 1-liter glass reactor with inlet ports for an agitator, water cooled condenser, thermocouple, and adapters for the addition of monomer and initiator solutions. The reactor contents were heated to 95° C. 27 g of 50% sodium hydroxide and 0.0616 g of ferrous ammonium sulfate hexahydrate was added. A mixed monomer solution which consisted of 170.52 g of acrylic acid (2.37 moles, 95.2 mol % of polymer), 26.7 g of 10% aqueous solution of N-(3-dimethylaminopropyl)-4-methoxy-1,8-naphthalimide, methallyl chloride quaternary salt (monomer of Monomer Example 1) with (formula weight 427, 0.00625 moles, 0.25 mol % of polymer) was mixed and then was added to the reactor via measured slow-addition with stirring over a period of 4 hours. A solution of 13.8 g of sodium hypophosphite monohydrate (0.119 moles, 4.78 mol % of polymer) dissolved in 41.2 g of water was concurrently fed into the reactor over 4 hours starting at the same time as the monomer solution. An initiator solution of 3.8 grams of sodium persulfate dissolved in 39 grams water was concurrently added, starting at the same time as the monomer solution, for a period of 4 hours and 15 minutes. The reaction product was then held at 95° C. for 60 minutes. The polymer solution was cooled and was then neutralized with 23 g of 50% sodium hydroxide. The final polymer solution had a solids content of about 45%, and a pH of 4.0.

Polymer Example 9

An initial charge of 153.3 g of deionized water and 152.6 of isopropyl alcohol was added to a 1-liter glass reactor with inlet ports for an agitator, water cooled condenser, thermocouple, and adapters for the addition of monomer and initiator solutions. Next, 0.095 g of ferrous ammonium sulfate hexahydrate was added to the reactor. The reactor contents were heated to 84° C. A mixed monomer solution which consisted of 193.3 g of acrylic acid (2.68 moles, 93.2 mol % of polymer) and 18.8 g of methyl methacrylate (0.188 moles, 6.5 mol % of polymer) and 1.45 g of N-(3-dimethylaminopropyl)-4-methoxy-1,8-naphthalimide, methallyl chloride quaternary salt (monomer of Monomer Example 1) (formula weight 403, 0.00359 moles, 0.125 mol % of polymer) dissolved in 6.9 g of 2-propanol, was mixed and then fed to the reactor via measured slow-addition with stirring over a period of 4 hours. An initiator solution of 11.75 grams of sodium persulfate and 39.3 g of 35% hydrogen peroxide was dissolved in 38.3 grams water was concurrently added, starting at the same time as the monomer solution, for a period of 4 hours. The reaction product was then held at 85° C. for 60 minutes. The reactor was then set up for distillation. An azeotropic of 242 g of a mixture of water and isopropyl alcohol was then distilled. 41.6 g of 50% sodium hydroxide dissolved in 221.4 g of deionized water was dripping during the distillation. The final polymer solution had a solids content of 38.6% and a pH of 4.0.

Polymer Example 10

An initial charge of 130 g of deionized water and 130.2 g of isopropyl alcohol was added to a 1-liter glass reactor with inlet ports for an agitator, water cooled condenser, thermocouple, and adapters for the addition of monomer and initiator solutions. Next, 0.081 g of ferrous ammonium sulfate hexahydrate was added to the reactor. The reactor contents were heated to 84° C. A mixed monomer solution which consisted of 168.4 g of acrylic acid (2.29 moles, 91.4 mol % of polymer) and 97.4 g of 2-acrylamido-2-methyl propane sulfonic acid sodium salt, 50% solution (0.21 moles, 8.5 mol % of polymer) and 1.25 g of N-(3-dimethylaminopropyl)-4-methoxy-1,8-naphthalimide, methallyl chloride quaternary salt (monomer of Monomer Example 1) (formula weight 403, 0.0031 moles, 0.125 mol % of polymer) dissolved in 6 g of 2-propanol, was mixed and then fed to the reactor via measured slow-addition with stirring over a period of 4 hours. An initiator solution of 10.01 grams of sodium persulfate and 33.4 g of 35% hydrogen peroxide was dissolved in 38.3 grams water was concurrently added, starting at the same time as the monomer solution, for a period of 4 hours. The reaction product was then held at 85° C. for 60 minutes. The reactor was then set up for distillation. An azeotropic of 222 g of a mixture of water and isopropyl alcohol was then distilled. 35.5 g of 50% sodium hydroxide dissolved in 200 g of deionized water was dripping during the distillation. The final polymer solution had a solids content of 39.6% and a pH of 4.1.

Polymer Example 11: (Comparative)

In this comparative example following the procedure outlined in Example 1 of CN 1939945 the polymer includes phosphino moieties and the amount of maleic monomer is greater than 85 mol %. A 500 ml reactor fitted with an overhead stirrer, thermocouple and controller, heating mantle and inlet ports for slow feeding monomer and initiator was charged with 81 g of water, 142.5 g of maleic anhydride (0.485 moles, 89.2 mol % of polymer), 7.5 g of sodium hypophosphite monohydrate (0.0235 moles, 4.34 mol % of polymer), 0.125 g of Vanadium (V) oxide and, 0.104 g of the of N-(3-dimethylaminopropyl)-4-methoxy-1, 8-naphthalimide, methallyl chloride quaternary salt (monomer of Monomer Example 1) (0.000258 moles, 0.047 mol % of polymer). The reaction mixture was heated to 80° C. A monomer solution of 7.5 g of acrylic acid (0.0347 moles, 6.5 mol % of polymer), dissolved in 11.8 g of water was added over 2 hours. Concurrently, 70.7 g of 35% hydrogen peroxide was added over 2 hours. The reaction exothermed and was held at 100-105° C. during the addition of the feeds. After the feeds were complete, the reaction was held at that temperature for one hour. The unreacted maleic acid was measured by LC. The conversion was found to be less than 40%. On cooling to room temperature, the reaction mixture precipitated out solids which were unreacted maleic acid. A vial of product contained a reddish-brown solution atop a white precipitate that filled up the bottom approximately 20% of the vial volume. This comparative example clearly shows that the combination of high maleic acid with phopsphino moieties in the polymer and quaternized naphthalimide fluorescent monomer suppresses the polymerization of maleic acid, leaving unreacted maleic acid in the polymerization product which rendered the resultant reaction mixture unusable. The residual maleic acid was measured by HPLC as follows:

Instrument: HPLC
Sample Prep: 75 mg of sample dispersed in 5 mL of 42 mM phosphoric acid, then a 1/100 dilution in 42 mM phosphoric acid
Calibration: standard prepared in 42 mM phosphoric acid
Mobile Phase: 42 mM phosphoric acid
Flow Rate: 600 µL/min
Column: Phenomenex Rezex ROA-Organic Acid H+ 300 mm×7.8 mm
Detector: UV detector monitoring at 205 nm The residual maleic acid was found to be 35.5 weight percent of the solution. 142.5 g of maleic anhydride becomes 168.7 g of maleic acid in the total weight percent of maleic acid 52.4%. Therefore, the maleic acid conversion is approximately 32.2%.

Polymer Example 12: (Comparative)

In this comparative example the polymer includes phosphino moieties and the amount of maleic monomer is greater than 70 mol %. A reactor fitted with an overhead stirrer, thermocouple and controller, heating mantle and inlet ports for slow feeding monomer and initiator was charged with 120 g of water, 84.99 g of maleic anhydride (0.866 moles, 74.92 mol % of polymer), 56.35 g of 50% sodium hydroxide solution, 0.0264 g of ferrous ammonium sulfate hexahydrate. The reaction mixture was heated to 85° C. A monomer solution of 16.63 g of acrylic acid (0.23 moles, 19.96 mol % of polymer), 0.60 g of N-(3-dimethylaminopropyl)-4-methoxy-1,8-naphthalimide, methallyl chloride quaternary salt (monomer of Monomer Example 1) (0.00148 moles, 0.13 mol % of polymer) dissolved in 2.73 g of isopropyl alcohol, 6.12 g of sodium hypophosphite monohydrate (0.058 moles, 4.99 mol % of polymer) mixed with 20 g of water was added over 4 hours. Concurrently, 60 g of 35% hydrogen peroxide, 3.7 g of sodium persulfate dissolved in 15 g of water was added over 4 hours. The reaction was held at 85° C. during the addition of the feeds. After the feeds were complete, the reaction was held at that temperature for one hour. Next, 0.15 g of tertiary butyl hydroperoxide, dissolved in 1.25 g of water was added in a shot in the reaction held for 5 minutes. After that, solution of 0.15 g of erythorbic acid, dissolved in 1.25 g of water was added over 30 minutes. The reaction was held at 85° C. for 30 minutes. A sample was then taken and the unreacted maleic acid was measured by HPLC as described in example 11 above. The residual maleic acid was found to be 8.2 weight percent. The maleic acid conversion was calculated to be 69.9 percent. On cooling to room temperature, the reaction mixture precipitated out solids which were unreacted maleic acid. A vial of product contained a cloudy yellow solution atop a white precipitate that filled up the bottom approximately 35% of the vial volume.

The example clearly shows that the combination of high maleic acid (75 mol %) with phosphino moieties and quaternized naphthalimide fluorescent monomer suppresses the polymerization of maleic acid, rendering the resultant reaction mixture unusable Polymer Example 13

A reactor fitted with an overhead stirrer, thermocouple and controller, heating mantle and inlet ports for slow feeding monomer and initiator was charged with 86 g of water, 45.32 g of maleic anhydride (0.46 moles, 50 mol % of polymer), 36.96 g of 50% sodium hydroxide solution, 0.0211 g of ferrous ammonium sulfate hexahydrate. The reaction mixture was heated to 95° C. A monomer solution of 30 g of acrylic acid (0.42 moles, 45 mol % of polymer), 0.50 g of N-(3-dimethylaminopropyl)-4-methoxy-1,8-naphthalilmide, methallyl chloride quaternary salt (monomer of Monomer example 1) (0.0012 moles, 0.13 mol % of polymer) dissolved in 2.4 g of isopropyl alcohol, 4.89 g of sodium hypophosphite monohydrate (0.05 moles, 5 mol % of polymer) mixed with 6 g of water was added over 4 hours. Concurrently, 42 g of 35% hydrogen peroxide, 3 g of sodium persulfate dissolved in 12 g of water was added over 4 hours. The reaction was held at 95° C. during the addition of the feeds. After the feeds were complete, the reaction was held at that temperature for one hour. On cooling to room temperature, the reaction mixture was a clear solution and did not have any precipitated solids. The residual maleic acid was found to be 40 ppm by the HPLC procedure described in Example 11. The maleic acid conversion was calculated to be greater than 99.9%. The maleic acid conversion was calculated to be 99.7%. The polymer was diluted to 10 ppm active in the pH was adjusted to 9. The fluorescence intensity was 2912 at excitation and emission wavelengths of 377 and 460 respectively.

Polymer Example 14

A reactor fitted with an overhead stirrer, thermocouple and controller, heating mantle and inlet ports for slow feeding monomer and initiator was charged with 112 g of water, 63.43 g of maleic anhydride (0.65 moles, 60 mol % of polymer), 51.75 g of 50% sodium hydroxide solution, 0.0246 g of ferrous ammonium sulfate hexahydrate. The reaction mixture was heated to 95° C. A monomer solution of 27.19 g of acrylic acid (0.38 moles, 35 mol % of polymer), 0.56 g of N-(3-dimethylaminopropyl)-4-methoxy-1,8-naphthalimide, methallyl chloride quaternary salt (monomer of Monomer example 1) (0.0014 moles, 0.13 mol % of polymer) dissolved in 2.4 g of isopropyl alcohol, 5.71 g of sodium hypophosphite monohydrate (0.05 moles, 5 mol % of polymer) mixed with 7 g of water was added over 4 hours. Concurrently, 49 g of 35% hydrogen peroxide, 3.5 g of sodium persulfate dissolved in 14 g of water was added over 4 hours. The reaction was held at 95° C. during the addition of the feeds. After the feeds were complete, the reaction was held at that temperature for one hour. On cooling to room temperature, the reaction mixture was a clear solution and did not have any precipitated solids. The residual maleic acid was found to be 550 ppm by the HPLC procedure described in Example 11. The maleic acid conversion was calculated to be 99.7%. The polymer was diluted to 10 ppm active in the pH was adjusted to 9. The fluorescence intensity was 3438 at excitation and emission wavelengths of 375 and 460 respectively.

Polymer Example 15

A reactor fitted with an overhead stirrer, thermocouple and controller, heating mantle and inlet ports for slow feeding monomer and initiator was charged with 112 g of water, 74 g of maleic anhydride (0.75 moles, 70 mol % of polymer), 60.38 g of 50% sodium hydroxide solution, 0.0246 g of ferrous ammonium sulfate hexahydrate. The reaction mixture was heated to 95° C. A monomer solution of 19.42 g of acrylic acid (0.27 moles, 25 mol % of polymer), 0.56 g of N-(3-dimethylaminopropyl)-4-methoxy-1,8-naphthalimide, methallyl chloride quaternary salt (monomer of Monomer example 1) (0.0014 moles, 0.13 mol % of polymer) dissolved in 2.4 g of isopropyl alcohol, 5.71 g of sodium hypophosphite monohydrate (0.05 moles, 5 mol % of polymer) mixed with 7 g of water was added over 4 hours. Concurrently, 49 g of 35% hydrogen peroxide, 3.5 g of sodium persulfate dissolved in 14 g of water was added over 4 hours. The reaction was held at 95° C. during the addition of the feeds. After the feeds were complete, the reaction was held at that temperature for one hour. On cooling to room temperature, the reaction mixture was a clear solution and did not have any precipitated solids. The residual maleic acid was found to be 2800 ppm by the HPLC procedure described in Example 11. The maleic acid conversion was calculated to be 98.9%. The polymer was diluted to 10 ppm active in the pH was adjusted to 9. The fluorescence intensity was 3585 at excitation and emission wavelengths of 376 and 461 respectively.

Example 16

Maleic Acid Conversion

The residual maleic acid for samples, with and without the phosphino group is presented in Table 3. The polymerization reaction products obtained with phosphino moieties were present are illustrated in FIG. 1.

TABLE 3

Comparison of maleic acid conversion in the presence and absence of phosphino moieties.

| Polymer | Polymer description | Mol % phosphino moiety | Residual maleic acid (weight percent) | Conversion of maleic acid |
|---|---|---|---|---|
| Example 3 | MA/FM 99.75/0.25 | 0 | 0.93 | 98 |
| Example 4 | AA/MA/FM 49.84/49.9/0.25 | 0 | 0.0023 | 99.9 |
| Example 11 (comparative) | AA/MA/phosphino/FM 6.39/89.2/4.34/0.047 | 4.34 | 35.5 | 32.2 |
| Example 12 (comparative) | AA/MA/phosphino/FM 19.96/74.92/4.99/0.13 | 4.99 | 8.2 | 69.9 |
| Example 13 | AA/MA/phosphino/FM 45.0/50.0/5.0/0.13 | 5.0 | 0.004 | 99.9 |
| Example 14 | AA/MA/phosphino/FM 35.0/60.0/5.0/0.13 | 5.0 | 0.0550 | 99.7 |
| Example 15 | AA/MA/phosphino/FM 25.0/70.0/5./0.13 | 5.0 | 0.28 | 98.9 |

Examples 3 and 4 clearly show that polymers containing maleic acid without the phosphino group have good conversion. By comparison, comparative examples 11 and 12 show that the presence of the phosphino group greatly suppresses the maleic acid polymerization and renders the resulting polymer solution unusable when the maleic acid is 75 mol % or higher. Surprisingly Example 13, 14 and 15 show that when the maleic acid is not greater than 70 mol % and phosphino groups are present, the maleic acid polymerization is not suppressed and it gives useful polymers.

Polymer Example 17: (Comparative)

An initial charge of 190.1 g of deionized water was added to a 1-liter glass reactor with inlet ports for an agitator, water cooled condenser, thermocouple, and adapters for the addition of monomer and initiator solutions. The reactor contents were heated to 95° C. A mixed monomer solution which consisted of 298.4 g of acrylic acid (4.14 moles, 94.4 mol % of polymer), 4.12 g of N-(3-dimethylaminopropyl)-4-chloro-1,8-naphthalimide, methallyl chloride quaternary salt (formula weight 397, 0.01038 moles, 0.24 mol % of polymer) was mixed and then fed to the reactor via measured slow-addition with stirring over a period of 4 hours. A second solution of 24.1 g of sodium hypophosphite monohydrate (0.23 moles, 5.25 mol % of polymer) dissolved in 72 g of deionized water was mixed and then fed to the reactor via measured slow-addition with stirring over a period of 4 hours. An initiator solution of 6.7 grams of sodium persulfate dissolved in 68.4 grams water was concurrently added, starting at the same time as the monomer solution, for a period of 4 hours and 15 minutes. The reaction product was then held at 95° C. for 60 minutes. The polymer solution was cooled and then neutralized with 40 g of 50% sodium hydroxide. The final polymer solution had a solids content of about 48.5 and a pH of 3.6.

TABLE 4

Fluorescence intensity of various polymers

| Polymer | Polymer description | Excitation wavelength λ (nm) | Emission wavelength λ (nm) | Fluorescence intensity |
|---|---|---|---|---|
| Example 1 | Acrylic acid/phosphino/N-(3-dimethylaminopropyl)-4-methoxy-1,8-naphthalilmide, methallyl chloride quaternary salt 94.4/5.25/0.24 | 377 | 458 | 11476 |
| Example 17 | Acrylic acid/phosphino/N-(3-dimethylaminopropyl)-4-chloro-1,8-naphthalilmide, methallyl chloride quaternary salt 94.4/5.25/0.24 | 355 | 405 | 1191 |

These data in Table 4 indicate that the chloro derivative of Polymer Example 17 moves the maxima for the excitation and emission wavelengths to lower wavelengths. In addition, the intensity of the fluorescent signal is lower. The halogen derivative N-(3-dimethylaminopropyl)-4-chloro-1,8-naphthalimide, methallyl chloride quaternary salt is an impurity in the synthesis of the N-(3-dimethylaminopropyl)-4-methoxy-1,8-naphthalimide, methallyl chloride quaternary salt. One monitors the polymer at the maximum of absorption and emission of the N-(3-dimethylaminopropyl)-4-methoxy-1,8-naphthalimide, methallyl chloride quaternary salt. If the N-(3-dimethylaminopropyl)-4-methoxy-1,8-naphthalimide, methallyl chloride quaternary salt monomer contains a halogen monomer as an impurity, some polymer chains will have the quaternized naphthalimide monomer and others the halogen derivative. Most importantly, since there are 2 signals coming from the polymer, significant amounts of halogen/chloro impurity gives a lower signal and has different maxima for excitation and emission, which then leads to an inaccurate measurement of the amount of polymer in the water treatment system. Also, since the signals are shifted to lower wavelengths, the fluorescent signal of the halogen/chloro impurity may interfere with the signals of the azole components of the water treatment formulation which are routinely used as copper corrosion inhibitors. Therefore, these halogen impurities produced during the synthesis of the monomer need to be minimized or eliminated. In a preferred embodiment, the N-(3-dimethylaminopropyl)-4-methoxy-1,8-naphthalimide monomer contains less than 10 mol %, preferably less than 5 mol %, more preferably less than 2 mol %, or is even completely free of N-(3-dimethylaminopropyl)-4-chloro-1,8-naphthalimide.

Example 18

Fluorescent Measurements

The fluorescence signal for the polymer of Example 1 at 10 ppm and at pH 9 was measured. Also, the fluorescence intensity of the intermediate N-(3-dimethylaminopropyl)-4-methoxy-1,8-naphthalilmide non-monomer intermediate used to synthesize the monomer used in Example 1 was measured at pH 9 and at 59 ppb. The 59 ppb was used because this is the amount of monomer that would have been present in 10 ppm of polymer.

TABLE 5

Fluorescence intensity of various polymers

| Polymer | Polymer description | Excitation wavelength λ (nm) | Emission wavelength λ (nm) | Fluorescence intensity |
|---|---|---|---|---|
| Example 1 | Acrylic acid/phosphino/N-(3-dimethylaminopropyl)-4-methoxy-1,8-naphthalilmide, methallyl chloride quaternary salt 94.4/5.25/0.24 | 377 | 458 | 11476 |
|  | N-(3-dimethylaminopropyl)-4-methoxy-1,8-naphthalilmide | 376 | 462 | 7788 |

These data indicate that the fluorescence intensity of the non-monomer intermediate of Structure (III) is surprisingly high and very close to that of the monomer. More importantly, the excitation and emission wavelengths are almost exactly the same for the monomer and the intermediate of Structure (III). Therefore, the in-line measurement would not be able to tell the difference between the monomer present in the polymer and the intermediate of Structure (III) present as an impurity. Therefore, it is important to minimize or eliminate the impurities of Structure (III).

Polymer Example 19

100 grams of xylene and 100 g of maleic anhydride is added to a 1-liter glass reactor with inlet ports for an agitator, water cooled condenser, thermocouple, and adapters for the addition of monomer and initiator solutions. The mixture is heated to reflux. An initiator solution of 10 g of tertiary butyl per-2-ethyl hexanoate and 50 g of xylene is added over 2 hours. 0.4 g of powdered N-(3-dimethylaminopropyl)-4-(meth)allyloxy-1,8-naphthalimide, 2-hydroxy propyl Quat is added to the reactor at the beginning of the initiator addition, at 30, 60 and 90 minutes. The reaction product is heated at reflux for 4 hours and then cooled to 90° C. 50 g of water is then added and the xylene is removed by introducing steam. A clear aqueous solution is obtained at the end of the reaction.

Polymer Example 20: (Comparative)

An initial charge of 140 g of deionized water and 34.7 g of isopropyl alcohol was added to a 1-liter glass reactor with inlet ports for an agitator, water cooled condenser, thermocouple, and adapters for the addition of monomer and initiator solutions. The reactor contents were heated to 84° C. A mixed monomer solution which consisted of 120.8 g of acrylic acid and 161.3 g of 2-acrylamido-2-methyl propane sulfonic acid sodium salt, 50% solution and 14.1 g of Monomer 3a solution (6% 4-methoxy-N-(3-dimethylaminopropyl)-1,8-naphthalimide, 2-hydroxy-3-allyloxy propyl, quaternary salt), was mixed and then fed to the reactor via measured slow-addition with stirring over a period of 3 hours. An initiator solution of 2.86 grams of sodium persulfate was dissolved in 47.8 grams water was concurrently added, starting at the same time as the monomer solution, for a period of 4 hours. The reaction product was then held at 85° C. for 60 minutes. The reactor was then set up for distillation. An azeotropic of 62.6 g of a mixture of water and isopropyl alcohol was then distilled. 57.7 g of 50% sodium hydroxide dissolved in 115.6 g of deionized water was dripping during the distillation. The final polymer solution had a solids content of 37.5% and a pH of 4.8.

Polymer Example 21

An initial charge of 185.4 g of deionized water and 45.9 g of isopropyl alcohol was added to a 1-liter glass reactor with inlet ports for an agitator, water cooled condenser, thermocouple, and adapters for the addition of monomer and initiator solutions. The reactor contents were heated to 84° C. A mixed monomer solution which consisted of 159.9 g of acrylic acid and 213.6 g of 2-acrylamido-2-methyl propane sulfonic acid sodium salt, 50% solution and 11.7 g solution of monomer 3 (10.3% of 4-methoxy-N-(3-dimethylaminopropyl)-1,8-naphthalimide, 1 or 2-hydroxy-3-allyloxy propyl, quaternary salt with minimal residual N-(3-dimethylaminopropyl)-4-methoxy-1,8-naphthalimide), was mixed and then fed to the reactor via measured slow-addition with stirring over a period of 3 hours. An initiator solution of 3.8 grams of sodium persulfate was dissolved in 45 grams water was concurrently added, starting at the same time as the monomer solution, for a period of 3.5 hours. The reaction product was then held at 85° C. for 60 minutes. The reactor was then set up for distillation. An azeotropic of 82.8 g of a mixture of water and isopropyl alcohol was then distilled. 162 g of deionized water was dripping during the distillation. The final polymer solution had a solids content of 37.7% and a pH of 1.9.

Polymer Example 22

The fluorescent signal for the starting N-(3-dimethylaminopropyl)-4-methoxy-1,8-naphthalilmide, the monomers from Monomer Example 3 and 3a (comparative) and the polymers of Polymer Example 20 (comparative) and Polymer Example 21 were measured at 10 ppm polymer and 45 ppb of N-(3-dimethylaminopropyl)-4-methoxy-1,8-naphthalilmide and monomers at pH 7.

TABLE 6

| | Fluorescence data | | | |
|---|---|---|---|---|
| sample | Description | Excitation wavelength λ (nm) | Emission wavelength λ (nm) | Fluorescence intensity |
| | N-(3-dimethylaminopropyl)-4-methoxy-1,8-naphthalilmide starting material | 376 | 460 | 9850 |
| Monomer Example 3a (comparative) | 4-methoxy-N-(3-dimethylaminopropyl)-1,8-naphthalimide, 2-hydroxy-3-allyloxy propyl, quaternary salt with ~20% N-(3-dimethylaminopropyl)-4-methoxy-1,8-naphthalilmide starting material | 376 | 460 | 8312 |
| Monomer Example 3 | 4-methoxy-N-(3-dimethylaminopropyl)-1,8-naphthalimide, 2-hydroxy-3-allyloxy propyl, quaternary salt with minimal N-(3-dimethylaminopropyl)-4-methoxy-1,8-naphthalilmide starting material | 376 | 460 | 6774 |

TABLE 6-continued

| | Fluorescence data | | | |
|---|---|---|---|---|
| sample | Description | Excitation wavelength λ (nm) | Emission wavelength λ (nm) | Fluorescence intensity |
| Polymer Example 20 (comparative) | Acrylic acid-AMPS with Monomer Example 3a | 376 | 460 | 6252 |
| Polymer Example 21 | Acrylic acid-AMPS with Monomer Example 3 | 376 | 460 | 5134 |

These fluorescence data indicate that the maximum wavelengths for absorption and emission were all the same, namely 376 and 460 respectively. More importantly, the N-(3-dimethylaminopropyl)-4-methoxy-1,8-naphthalilmide starting material has a signal that is stronger than that of the Monomer Example 3a which has approximately 20% unreacted starting N-(3-dimethylaminopropyl)-4-methoxy-1,8-naphthalilmide amine. Thus, the polymer Example 20 will have a significant fraction of unreacted N-(3-dimethylaminopropyl)-4-methoxy-1,8-naphthalilmide amine that is not incorporated into the polymer. The signal of this polymer will have a starting error of approximately 20% and this error will increase as the cycles of concentration in the end use increases. Since the polymer needs to be detected to an accuracy of less than 5-10% error to be useful, the monomer and polymers of the comparative examples are not.

In another set of experiments the fluorescence signal for polymers of Example 20 (comparative) and 21 was measured in the presence of 1 ppm chlorine and at pH 7.

TABLE 7

| | Fluorescence data | | | | |
|---|---|---|---|---|---|
| sample | Time | pH | Excitation wavelength λ (nm) | Emission wavelength λ (nm) | Fluorescence intensity |
| Polymer Example 20 (comparative) | 0 hours | 7.17 | 376 | 460 | 6038 |
| Polymer Example 20 (comparative) | 24 hours | 7.15 | 376 | 460 | 5159 |
| Polymer Example 21 | 0 hours | 7.01 | 376 | 460 | 4934 |
| Polymer Example 21 | 24 hours | 6.96 | 376 | 460 | 5298 |

These data indicate that the Polymer of example 20 (comparative) has an approximately 15% drop in fluorescent signal in the presence of 1 ppm chlorine. By comparison, the polymer of this disclosure Polymer Example 21 tends to maintain it signal, even in the presence of 1 ppm chlorine. As mentioned before, the polymer fluorescent signal needs to be accurate to within less than 10% to have practical viability. These data indicate that the monomer and polymers of this disclosure are superior to that of the prior art.

Polymer Example 23

A reactor containing 103.85 grams of DI water and 88.52 grams of Star DRI 42 (from Tate and Lyle) was heated to 188° F. 0.22 grams of maleic anhydride and 3.58 grams of hydrogen peroxide, 35% was added to the reactor at 140° F. A mixed monomer solution containing 28.8 grams of acrylic acid and 2.7949 grams of the solution from Monomer Example 3 was added to the reactor over a period of 2 hours. An initiator solution comprising of 3.7986 grams of sodium persulfate dissolved in 41.66 grams of deionized DI water was simultaneously added to the reactor over a period of 2 hours and 30 minutes. The reaction product was held at 188° F. for an additional 30 minutes. At the end of the cook, reactor was cooled down to 160° F. 2.24 grams of sodium bisulfite was added as a shot in the reaction mixture was held at that temperature for an additional 15 minutes. A solution of 15.32 grams of sodium hydroxide in 15.32 grams DI water was added to the reactor over 15 mins. The polymer solution was then mixed for 15 minutes and cooled down to room temperature. 0.49 grams of Proxel GXL was added to the reactor and mixed for 5 minutes. The final polymer was a yellow solution at 41.5% solids and pH of 4.58.

Polymer Example 24

A reactor containing 140.80 grams of deionized water and 15.26 grams of sodium chloride was heated to 132° F. A mixed monomer solution containing 65.5 grams of diallyl dimethylammonium chloride (65% solution in water), 8.78 grams of dimethyl aminoethyl methacrylate methyl chloride (75% solution in water) and 2.04 grams of the solution from Monomer Example 3 was added to the reactor over a period of 4 hours. An initiator solution comprising of 0.1519 grams of VA-044 (from Wako) dissolved in 37.48 grams of deionized DI water was simultaneously added to the reactor over a period of 4 hours. The reaction product was held at 132° F. for an additional 30 minutes. At the end of the cook, a solution of 0.1512 grams of VA-044 in 5.02 grams of DI water was added as a shot and solution was cooked for an hour at 180° F. The final polymer was a yellow solution at 24.9 solids and pH of 4.26.

Polymer Example 25

A reactor containing 148.75 grams of deionized water, and 57.73 grams of sodium sulfate was heated to 144° F. When the reactor reached 144° F., 0.11 grams of ethylenediaminetetraacetic acid was added to the reactor. A mixed monomer solution containing 52.8 grams of acrylamide, 59.9 grams of dimethyl aminoethyl methacrylate methyl chloride (75% solution in water), 5.6 grams of glycerine and 2.75 grams of the monomer solution from Monomer Example 3 was added to the reactor over a period of 3 hours. An initiator solution comprising of 0.4443 grams of V-50 (from Wako) dissolved in 44.29 grams of deionized deionized water was simultaneously added to the reactor over a period of 3 hours. The reaction product was held at 144° F. for an additional 2 hours. At the end of the cook, a solution of 0.0109 grams of V-50 in 1.03 grams of deionized water was added as a shot and solution was cooked for an hour at 144° F. The final polymer was a yellow solution at 27.0% solids and pH of 3.32.

Polymer Example 26

A reactor containing 98.97 grams of deionized water and 174.92 grams of diallyldimethylammonium chloride (65% solution in water) was heated to 155° F. while sparging with Nitrogen. A monomer mixture solution of 32.34 grams of acrylic acid, 9.97 grams of the monomer solution from Monomer Example 3 and 36.96 grams of hydroxypropyl acrylate was prepared. An initiator solution of 0.78 grams of ammonium persulfate dissolved in 32.45 grams of deionized water was also prepared. When the reactor had reached 155° F., 0.2615 grams of Versene 100 was added to the reactor. Next, 6.9 ml of the monomer solution was added as a shot and mixed for 5 minutes. 7.8 ml of the initiator solution was added as a shot at the end of 5 minutes. The reaction temperature was maintained below 170° F. When the temperature was stable at 155° F., the monomer and initiator solution was fed over 3 hours simultaneously. At the end of the feed, the reactor was held at 170 F for 2 hours. Next, the reaction temperature was raised to 185 F and held at that temperature for 1 hour. The reaction solution was cooled down to room temperature and a solution of 12.25 grams of sodium hydroxide and 271.12 grams of deionized water was added and mixed for 15 minutes. The final polymer was an opaque solution at 27.4% solids and pH of 3.72.

Polymer Example 27

A reactor containing 70.51 grams of deionized (DI) water and 64.42 grams of isopropyl alcohol was heated to 183° F. 3 grams of solution of 0.1736 grams Ferrous ammonium sulfate in 15 grams deionized water. A monomer solution containing 50.0 grams of acrylic acid, 50.5 grams of styrene, 2.5 grams of methacrylic acid and 0.4041 grams of the of the monomer solution from Monomer Example 3 was added to the reactor over a period of 3 hours and 30 minutes. An initiator solution comprising of 4.6 grams of sodium persulfate in 28.89 grams of DI water was simultaneously added to the reactor over a period of 4 hours. A solution containing 4.0 grams of 3-mercapto propionic acid in 21.25 grams of DI water was also added simultaneously over 3 hours 15 minutes. The reaction product was held at 188° F. for an additional 1 hour. At the end of the cook, 0.06 grams of Silicone S-100 was added to the reactor. The reactor was set up for distillation and 130.0 grams of an azeotropic distillate was distilled off. During the distillation, 62.60 grams of caustic solution in 95.15 grams of DI water was added. At the end of the distillation, reactor was cooled down to 90° F. The final polymer was an opaque amber solution at 35.3% solids and pH of 9.29.

Example 28: Fluorescence Signal Strength

The polymer samples from the indicated Examples were diluted in water to 10 ppm. The fluorescent signal was determined by excitation of the sample at the excitation wavelengths and measurement at the emission wavelengths as stated in Table 8.

TABLE 8

Fluorescence data for Polymer Examples

| Polymer Example number | Emission | Excitation | Intensity |
|---|---|---|---|
| 23 | 456 | 376 | 4572 |
| 24 | 460 | 374 | 3697 |
| 25 | 460 | 374 | 2099 |
| 26 | 459 | 376 | 5339 |
| 27 | 458 | 375 | 1971 |

Polymer Example 29

An initial charge of 162.6 g of maleic anhydride mixed with 544.5 g of deionized water was added to a 2-liter glass reactor with inlet ports for an agitator, water cooled condenser, thermocouple, and adapters for the addition of monomer and initiator solutions. The mixture was heated to 65° C. The maleic anhydride was neutralized using 66.4 g of 50% sodium hydroxide while keeping the temperature above 65° C. Next, 0.1514 g of ferrous ammonium sulfate hexahydrate was added to the reactor. The reactor contents were heated to 84° C. A mixed monomer solution which consisted of 307.9 g of acrylic acid, 29.8 g of methyl methacrylate, 181.9 g of 2-acrylamido-2-methyl propane sulfonic acid sodium salt, 50% solution, 92.5 g of N-(3-dimethylaminopropyl)-4-methoxy-1,8-naphthalimide, 2-hydroxy-3-(meth)allyloxypropyl quaternary salt (10.3% monomer solution of Monomer Example 3), was mixed and then fed to the reactor via measured slow-addition with stirring over a period of 4 hours. An initiator solution of 37.4 grams of sodium persulfate and 125.1 g of 35% hydrogen peroxide was dissolved in 93.9 grams water was concurrently added, starting at the same time as the monomer solution, for a period of 4 hours. The reaction product was then held at 85° C. for 60 minutes. 0.9 g of erythorbic acid is sold in 7 g of water was then added. The final polymer solution had a solids content of 39.3% and a pH of 4.0.

The residual N-(3-dimethylaminopropyl)-4-methoxy-1,8-naphthalimide, 2-hydroxy-3-(meth)allyloxypropyl quaternary salt was measured by LC (see method below) and was found to be below the detection limit which is 20 ppm or greater than 99.6% conversion.

If the N-(3-dimethylaminopropyl)-4-methoxy-1,8-naphthalimide, 2-hydroxy-3-(meth)allyloxypropyl quaternary salt was not low enough we could mix this monomer with 80% of the acrylic acid and of 2-acrylamido-2-methyl propane sulfonic acid sodium salt and add that mixture over 4 hours, add the rest of the 20% of the acrylic acid and of 2-acrylamido-2-methyl propane sulfonic acid sodium salt over the next hour and feed the initiator solution over 5 hours. This would have given the acrylic acid and of 2-acrylamido-2-methyl propane sulfonic acid sodium salt and add that mixture over 4 hours, add the rest of the 20% of the acrylic acid and of 2-acrylamido-2-methyl propane sulfonic acid sodium salt a chance to react with the fluorescent monomer. We would monitor the disappearance of the fluorescent monomer over the last hour. If it were consumed over say 30 minutes, we would shorten the 20% of the acrylic acid and of 2-acrylamido-2-methyl propane sulfonic acid sodium salt feed to 30 minutes. If it were not consumed over in an hour, we would lengthen the 20% of the acrylic acid and of 2-acrylamido-2-methyl propane sulfonic acid sodium salt feed to 90 minutes. Alternatively, if it were not consumed over in an hour, we would mix fluorescent monomer with 60% of the acrylic acid and of 2-acrylamido-2-methyl propane sulfonic acid sodium salt and add that mixture over 3 hours, add the rest of the 40% of the acrylic acid and of 2-acrylamido-2-methyl propane sulfonic acid sodium salt over the next 2 hours and feed the initiator solution over 5 hours.

The LC method:
Column: Zorbax SB-C8 StableBond 4.6 mm×250 mm 5-micron
Detector: Waters 2998 PDA detector; scanning 201-600 nm; quantitation at 364 nm
Flow Rate: 1 mL/min
Injection Volume: 25 µL
Mobile phase A: 25 mM sodium acetate in water
Mobile phase B: methanol
Gradient: 80% A for 5 min, linear change to 30% A at 5.5 min, hold 30% A for 18.5 min Diluent: 50% mobile phase A/50% mobile phase B
Samples: 600 mg of sample in 10 mL of diluent
Standard: Monomer 3 10% active was used for the spiked sample

The invention claimed is:

1. A quaternized fluorescent monomer comprising the structure:

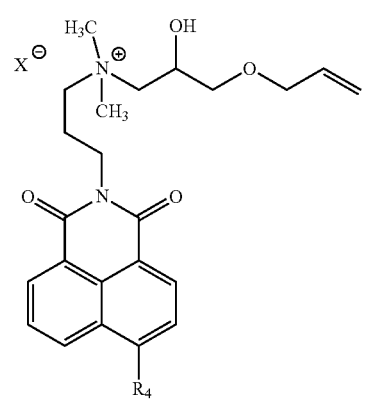

wherein $R_4$ is selected from H, hydroxy, alkoxy or $C_1$-$C_4$alk-O—($CHR_5CH_2O$—)n;

$R_5$ is selected from H and $C_1$-$C_4$-alkyl;

n is 1-10; and $X^-$ is an anionic counter ion;

and comprising less than 8 mol%, based on 100 mol% of total naphthalimide fluorescent monomer of the structure:

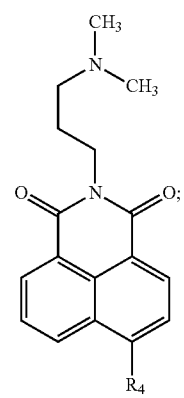

wherein $R_4$ is as defined above.

2. The quaternized fluorescent monomer of claim 1, which comprises the structure:

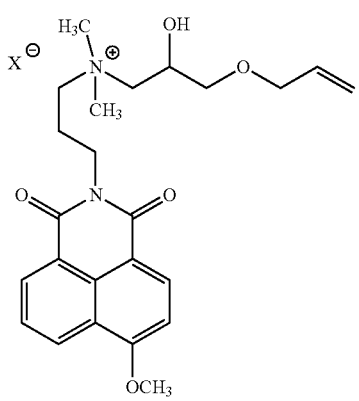

wherein X⁻ is an anionic counter ion;
and comprises less than 8 mol%, based on 100 mol% of total naphthalimide fluorescent monomer of the structure:

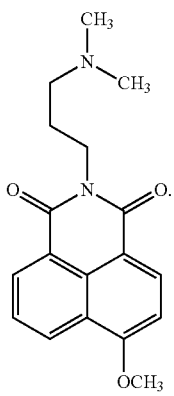

3. The quaternized fluorescent monomer of claim 2, wherein X⁻ is an anionic counterion selected from the group consisting of chloride, bromide, hydroxide, methosulphate, sulfate, sulfonate, carboxylate, phosphate, and phosphonate.

4. The quaternized fluorescent monomer of claim 1, wherein X⁻ is an anionic counterion selected from the group consisting of chloride, bromide, hydroxide, methosulphate, sulfate, sulfonate, carboxylate, phosphate, and phosphonate.

5. The quaternized fluorescent monomer of claim 1, which comprises (a) N-(3-dimethylaminopropyl)-4-methoxy-1,8-naphthalimide, 2-hydroxy-3-(meth)allyloxypropyl quaternary salt comprising less than 5 mol% of (b) N-(3-dimethylaminopropyl)-4-methoxy-1,8-naphthalimide, based on 100 mol% of (a).

6. A polymer prepared by polymerizing the quaternized fluorescent monomer of claim 5 with other monomers.

7. The quaternized fluorescent monomer of claim 1, which comprises (a) N-(3-dimethylaminopropyl)-4-methoxy-1,8-naphthalimide, 2-hydroxy-3-(meth)allyloxypropyl quaternary salt comprising less than 1.5 mol% of (b) N-(3-dimethylaminopropyl)-4-methoxy-1,8-naphthalimide, based on 100 mol% of (a).

8. A polymer prepared by polymerizing the quaternized fluorescent monomer of claim 7 with other monomers.

9. A polymer prepared by polymerizing the quaternized fluorescent monomer of claim 1 with other monomers.

10. The polymer according to claim 9, wherein the other monomers are selected from the group consisting of cationic, anionic, and/or nonionic monomers.

11. The polymer according to claim 10, wherein the quaternized fluorescent monomer is incorporated into the polymer to an extent equal to or greater than 90 mol%.

12. The polymer according to claim 10, wherein the quaternized fluorescent monomer is incorporated into the polymer to an extent equal to or greater than 95 mol%.

13. A water treatment polymer formed from polymerizing a polymerization mixture comprising:
(i) at least one water-soluble carboxylic acid monomer, or salt or anhydride thereof, present in an amount of 10-99.999 mol% based on 100 mol% of the polymer;
(ii) the quaternized fluorescent monomer of claim 1; and
wherein the polymer chains of the water treatment polymer formed comprise 0.001 mol% to less than or equal to 10 mol% of the quaternized fluorescent monomer of claim 1 as unreacted monomer unincorporated into the polymer chains thereby indicating that said quaternized fluorescent monomer of claim 1 has been incorporated into said water treatment polymer to an extent equal to or greater than 90 mol%.

14. The polymer of claim 13, wherein said quaternized fluorescent monomer is incorporated into the polymer to the extent of at least 95 mol%.

15. The polymer of claim 13, wherein the polymerization mixture comprises (a) N-(3-dimethylaminopropyl)-4-methoxy-1,8-naphthalimide, 2-hydroxy-3-(meth)allyloxypropyl quaternary salt comprising less than 5 mol% of (b) N-(3-dimethylaminopropyl)-4-methoxy-1,8-naphthalimide, based on 100 mol% of (a).

16. The polymer of claim 15, wherein (a) is incorporated into the polymer to the extent of at least 95 mol%.

17. The polymer of claim 13, wherein the polymerization mixture comprises (a) N-(3-dimethylaminopropyl)-4-methoxy-1,8-naphthalimide, 2-hydroxy-3-(meth)allyloxypropyl quaternary salt comprising less than 1.5 mol% of (b) N-(3-dimethylaminopropyl)-4-methoxy-1,8-naphthalimide, based on 100 mol% of (a).

18. The polymer of claim 17, wherein (a) is incorporated into the polymer to the extent of at least 98 mol%.

19. A process of preparing a water treatment polymer, the process comprising the following steps:
(a) polymerizing a polymerization mixture comprising:
(i) at least one water-soluble carboxylic acid monomer, or salt or anhydride thereof, present in an amount of 10-99.999 mol% based on 100 mol% of the polymer;
(ii) the quaternized fluorescent monomer of claim 1; and
(b) wherein the polymer chains of the water treatment polymer formed comprise 0.001 mol% to less than or equal to 10 mol% of the quaternized fluorescent monomer of claim 1 as unreacted monomer unincorporated into the polymer chains thereby indicating that said quaternized fluorescent monomer of claim 1 has been incorporated into said water treatment polymer to an extent equal to or greater than 90 mol%.

20. A method of controlling scale in a water system, the method comprising the steps of:
(a) dosing the water system with a water treatment polymer according to claim 13; and
(b) monitoring the fluorescent signal emitted from said water system.

21. A method for coagulation or flocculation in a water treatment system, the method comprising the steps of:
(a) dosing the water treatment system with the water treatment polymer according to claim 13; and
(b) monitoring the fluorescent signal emitted from the water treatment system.

22. A method for determining whether a given location has been cleaned comprising the steps of:
- (a) applying the water treatment polymer according to claim 13 to the location;
- (b) cleaning the location at least once; and
- (c) measuring fluorescence at the location after said cleaning, which, presence, if detected, indicates that additional cleaning is needed.

23. A method of controlling scale in a water system, the method comprising the steps of:
- (a) dosing the water system with a water treatment polymer according to claim 9; and
- (b) monitoring the fluorescent signal emitted from said water system.

24. A method for coagulation or flocculation in a water treatment system, the method comprising the steps of:
- (a) dosing the water treatment system with the water treatment polymer according to claim 9; and
- (b) monitoring the fluorescent signal emitted from the water treatment system.

25. A method for determining whether a given location has been cleaned comprising the steps of:
- (a) applying the water treatment polymer according to claim 9 to the location;
- (b) cleaning the location at least once; and
- (c) measuring fluorescence at the location after said cleaning, which, presence, if detected, indicates that additional cleaning is needed.

* * * * *